United States Patent
Boyle, Jr. et al.

(10) Patent No.: US 11,884,505 B2
(45) Date of Patent: Jan. 30, 2024

(54) DEVICES AND METHODS RELATED TO MEDICAL TUBES

(71) Applicant: ClearFlow, Inc., Irvine, CA (US)

(72) Inventors: Edward M. Boyle, Jr., Bend, OR (US); Paul Molloy, Anaheim, CA (US); Wayne A. Noda, Mission Viejo, CA (US); Kenneth J. Chesnin, Long Beach, CA (US); Al Diaz, Anaheim, CA (US); Daniel Hyman, Foothill Ranch, CA (US); Jon D. Jacobson, Irvine, CA (US)

(73) Assignee: ClearFlow, Inc., Irvine, CA (US)

( * ) Notice: Subject to any disclaimer, the term of this patent is extended or adjusted under 35 U.S.C. 154(b) by 468 days.

(21) Appl. No.: 16/485,967

(22) PCT Filed: Feb. 12, 2018

(86) PCT No.: PCT/US2018/017807
§ 371 (c)(1),
(2) Date: Aug. 14, 2019

(87) PCT Pub. No.: WO2018/152059
PCT Pub. Date: Aug. 23, 2018

(65) Prior Publication Data
US 2020/0054863 A1    Feb. 20, 2020

Related U.S. Application Data

(60) Provisional application No. 62/460,070, filed on Feb. 16, 2017.

(51) Int. Cl.
*A61M 25/09* (2006.01)
*B65H 75/36* (2006.01)
(Continued)

(52) U.S. Cl.
CPC ......... *B65H 75/364* (2013.01); *A61B 5/0022* (2013.01); *A61B 5/01* (2013.01);
(Continued)

(58) Field of Classification Search
CPC ........ A61M 1/83; A61M 1/86; A61M 1/0023; A61M 25/09041; A61M 27/00;
(Continued)

(56) References Cited

U.S. PATENT DOCUMENTS

| 4,160,451 A | 7/1979 | Chittenden |
| 7,951,243 B2 | 5/2011 | Boyle et al. |

(Continued)

FOREIGN PATENT DOCUMENTS

| CN | 202665587 U | 1/2013 |
| JP | 2004208961 | 7/2004 |
| JP | 2015-503395 | 2/2015 |

OTHER PUBLICATIONS

International Search Report & Written Opinion issued in corresponding International Patent Application No. PCT/US2018/017807 dated Apr. 26, 2018, 15 pages.
(Continued)

*Primary Examiner* — Michael R Bloch
(74) *Attorney, Agent, or Firm* — Pearne & Gordon LLP

(57) ABSTRACT

Apparatus and methods for clearing obstructions from a medical tube are disclosed. In an exemplary embodiment, a spool drive system is disclosed for actuating a guide wire within a medical tube. The spool drive system can be a hand held, disposable device having a spool housing with a spool therein for alternately advancing and withdrawing a guide wire through an inlet of the spool housing. A track can be spaced from and extend about a perimeter of the spool to direct the guide wire onto or off of the spool as the spool is
(Continued)

rotated. Other embodiments and devices for actuating the guide wire, and methods therefor, also are disclosed.

26 Claims, 41 Drawing Sheets

(51) Int. Cl.
*A61B 5/00* (2006.01)
*A61B 5/01* (2006.01)
*A61B 5/0205* (2006.01)
*A61B 5/024* (2006.01)
*A61B 5/08* (2006.01)
*A61B 5/11* (2006.01)
*A61M 27/00* (2006.01)
*A61B 5/349* (2021.01)
*A61M 1/00* (2006.01)

(52) U.S. Cl.
CPC .......... *A61B 5/024* (2013.01); *A61B 5/02055* (2013.01); *A61B 5/0816* (2013.01); *A61B 5/0823* (2013.01); *A61B 5/1113* (2013.01); *A61B 5/1118* (2013.01); *A61B 5/349* (2021.01); *A61B 5/4824* (2013.01); *A61M 1/75* (2021.05); *A61M 1/83* (2021.05); *A61M 1/86* (2021.05); *A61M 25/09041* (2013.01); *A61M 27/00* (2013.01); *A61M 2205/0216* (2013.01); *A61M 2205/18* (2013.01); *A61M 2205/3303* (2013.01); *A61M 2205/3324* (2013.01); *A61M 2205/3344* (2013.01); *A61M 2205/50* (2013.01); *A61M 2205/8206* (2013.01); *A61M 2210/101* (2013.01); *A61M 2230/201* (2013.01); *A61M 2230/207* (2013.01); *A61M 2230/208* (2013.01); *A61M 2230/63* (2013.01)

(58) Field of Classification Search
CPC ...... A61M 2205/0216; A61M 2205/18; A61M 2205/3303; A61M 2205/3324; A61M 2205/3344; A61M 2205/50; A61M 2205/8206; A61M 2210/101; A61M 2230/201; A61M 2230/207; A61M 2230/208; A61M 2230/63; A61B 5/0022; A61B 5/01; A61B 5/349; A61B 5/02055; A61B 5/024; A61B 5/0816; A61B 5/0823; A61B 5/1113; A61B 5/1118; A61B 5/4824
See application file for complete search history.

(56) References Cited

U.S. PATENT DOCUMENTS

| | | | |
|---|---|---|---|
| 10,265,442 | B2 | 4/2019 | Luxon et al. |
| 2012/0285485 | A1 | 11/2012 | Majeed |
| 2015/0202414 | A1 | 7/2015 | Hwang |
| 2015/0231313 | A1 | 8/2015 | O'Keefe et al. |
| 2015/0305819 | A1 | 10/2015 | Krause |
| 2016/0175563 | A1 | 6/2016 | Woehr et al. |
| 2017/0143880 | A1 | 5/2017 | Luxon et al. |
| 2019/0201596 | A1 | 7/2019 | Luxon et al. |

OTHER PUBLICATIONS

"Superior Chest Drainage With an Active Tube Clearance System: Evaluation of a Downsized Chest Tube," Yoko Arakawa, MD, Akira Shiose, MD, PhD, Tohru Takaseya, MD, PhD, Hideyuki Fumoto, MD, Hyun-Il Kim, MD, Edward M. Boyle, MD, A. Marc Gillinov, MD, and Kiyotaka Fukamachi, MD, PhD: Ann Thorac Surg 2011;91: pp. 580-583.
Office action issued in corresponding Indian Patent Application No. 201917033083 dated Jul. 7, 2021, 6 pages.
Office action issued in corresponding Chinese Patent Application No. 201880018193 dated Oct. 13, 2020, 23 pages.
English translation of Office action issued in corresponding Japanese Patent Application No. 2022-112775 dated Jun. 6, 2023, 16 pages.

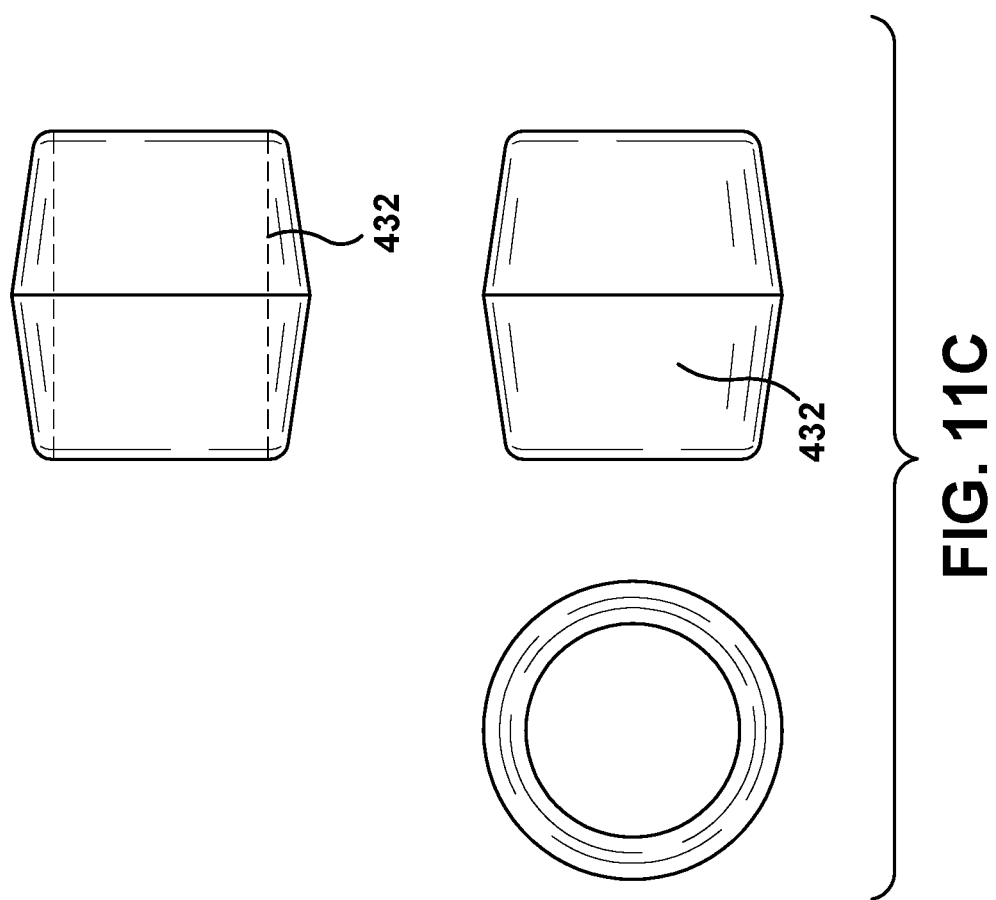

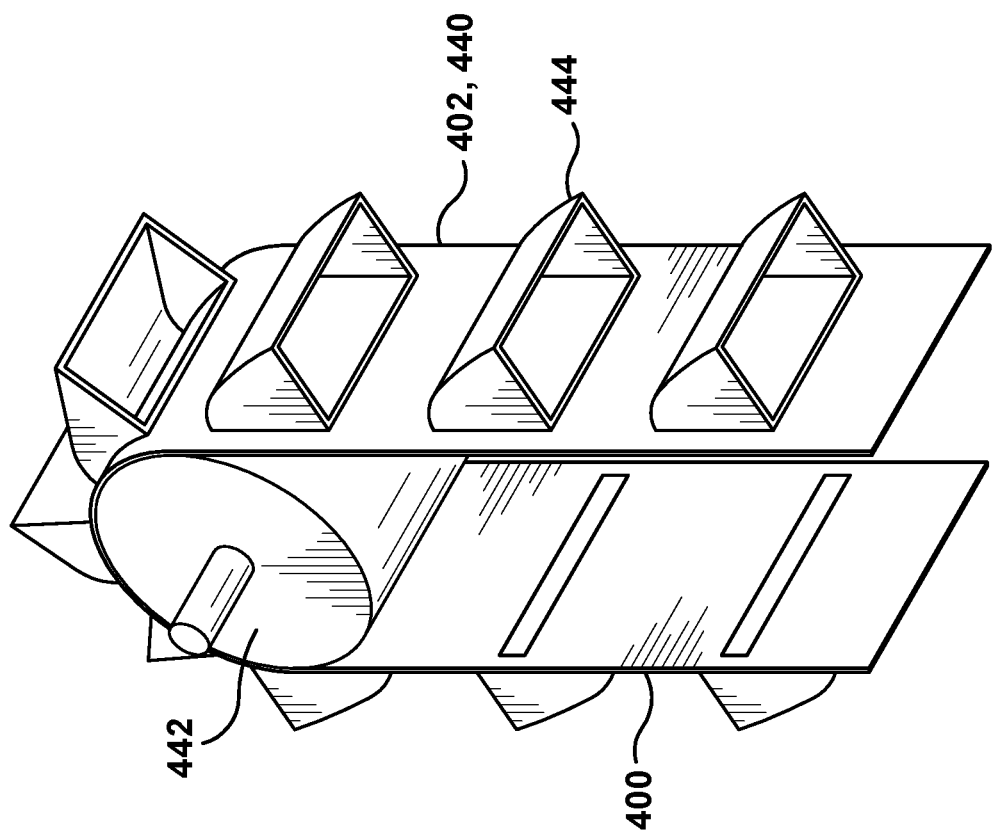

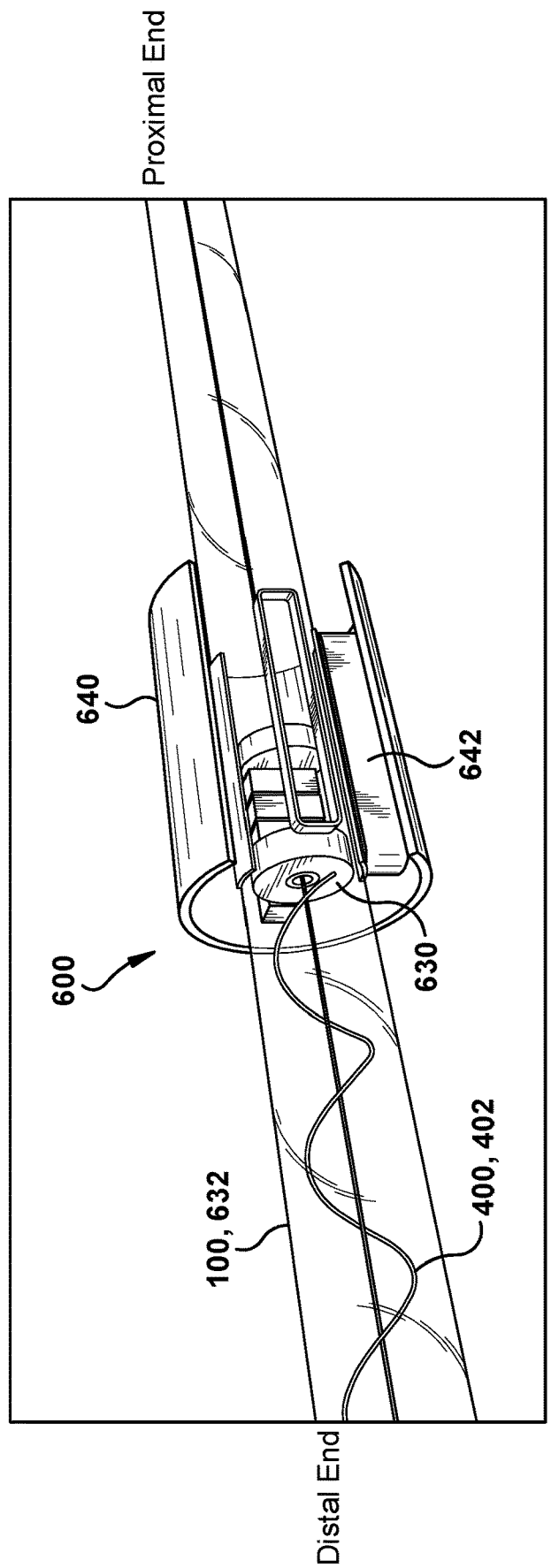

DEVICES AND METHODS RELATED TO MEDICAL TUBES

CROSS REFERENCE TO RELATED APPLICATIONS

This application claims priority to U.S. provisional patent application Ser. No. 62/460,070 filed Feb. 16, 2017, the contents of which are incorporated herein by reference.

BACKGROUND

Medical tubes can be used to deliver fluids or devices into a body and/or to drain bodily fluids, secretions, and debris from compartments and structures within the body. For example, medical tubes can be used to drain fluid from one's bladder, from the colon or other portions of the alimentary tract, or from the lungs or other organs in conjunction with various therapies. As another example, medical tubes can be used to drain blood and other fluids that typically accumulate within a body cavity, such as the mediastinal, pericardial, pleural or peritoneal spaces following surgery, infection or trauma. As yet another example, medical tubes can be used to deliver fluids to a body for nourishment within the alimentary tract or they can be used to provide access to the vasculature for removal or delivery of fluids, medications or devices. Typically, a medical tube is inserted into the patient so that its distal end is provided in or adjacent the space where it is desired to remove or deliver material while a proximal portion remains outside the patient's body, where it can be accessed and/or connected, for example, to a suction source.

Fluids passing through a medical tube (particularly when exposed to blood, platelets, pus or other thick substances) can form clots or other obstructions within the medical tube, which can partially or totally obstruct the pathway within the tube. Obstruction of the medical tube can impact its effectiveness to remove or deliver the fluid and other material for which it was originally placed, eventually rendering the medical tube partially or totally non-functional. In some cases, a non-functional tube can have serious or potentially life-threatening consequences. For example, if there is a blockage in a chest tube following cardiac or pulmonary surgery, the resulting accumulation of fluid (e.g., air) around the heart and lungs without adequate drainage can cause serious adverse events such as pericardial tamponade and pneumothorax.

BRIEF DESCRIPTION OF THE DRAWINGS

FIG. 11C shows a side view, top view and front view of another example bead that is part of the seventh example clearance wire assembly;

FIG. 12B shows a schematic perspective view of the eighth example clearance wire assembly with cup-shaped clearance members;

FIG. 18 shows a schematic, partially broken-away perspective view of a second example drive system for a clearance-wire assembly of the fluid system;

DETAILED DESCRIPTION OF PREFERRED EMBODIMENTS

Figure 1:
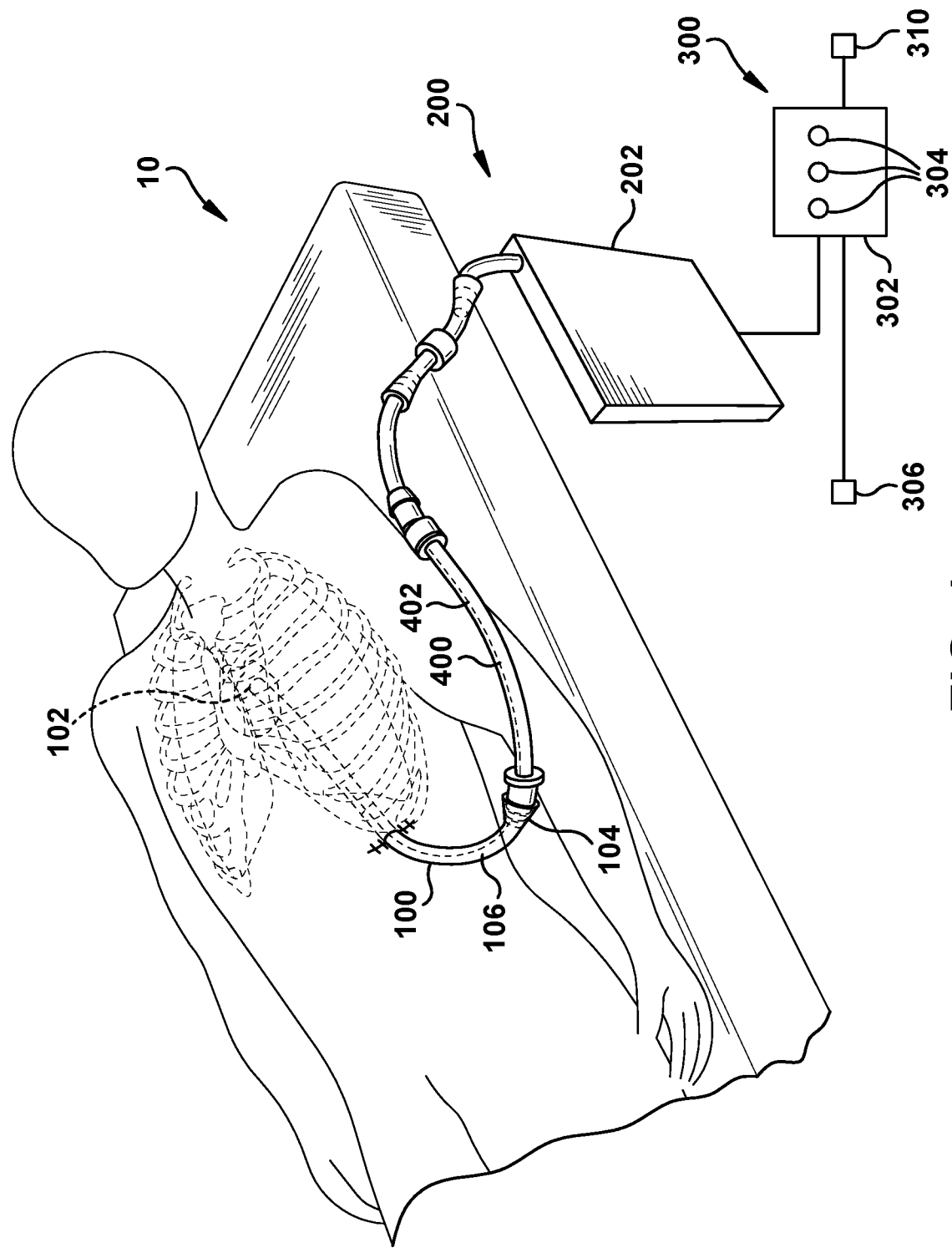
FIG. 1 shows a schematic perspective view of a fluid system having a medical tube implanted with a patient.

Certain terminology is used herein for convenience only and is not to be taken as a limitation on the present invention. Relative language used herein is best understood with reference to the drawings, in which like numerals are used to identify like or similar items. Further, in the drawings, certain features may be shown in schematic form.

It is to be noted that the terms "proximal" and "distal" as used herein when describing two features indicate a relative positioning that those two features will generally have along a fluid path that is tied to a patient, the distal feature being closer to the patient than the proximal feature along the fluid path. For example, for a medical tube that draws or delivers fluid to a patient, a distal end or portion of the medical tube will be closer to the patient than a proximal end or portion of the medical tube along the flow path of the fluid. As another example, in a fluid system wherein a medical tube fluidly connects a patient to a drain, the drain will be proximal to the medical tube since the drain is farther from the patient than the medical tube along the flow path of the system. Conversely, the medical tube will be distal to the drain since the medical tube is closer to the patient than the drain along the flow path of the system.

It is to be noted that the term "material" as used herein can refer to blood or other bodily fluids, medicine, food, debris, clot material (such as blood clot), air or any other fluid, solid, or semi-solid, including pus.

The term "coupled" as used herein when describing two or more features means that the features are fixedly or movably connected to each other. The features may be integral parts of the same component or the features may be separate components that are connected, either directly or indirectly, using structure or methods such as, for example, fasteners, adhesive, over-molding, hooks, threaded couplings, snap-fit connections, welding, soldering, tying, crimping, magnetic coupling, press-fit, barbed connections, etc. The term "fluidly coupled" as used herein when describing two or more features means that the features are coupled in a manner such that fluid communication is provided between the two features, either directly or through some intermediate structure. Such intermediate structure can be, for example, hoses, tubes, hose barbs, threaded connectors, compression fittings, etc.

Examples will now be described more fully hereinafter with reference to the accompanying drawings in which example embodiments are shown.

FIG. 1 shows a schematic representation of a fluid system 10 having a medical tube 100 that includes a distal end 102 positioned within the body of a patient and a proximal end 104 positioned outside of the patient's body. The medical tube 100 can correspond to the medical tube disclosed in U.S. Patent Application Publication No. 2015/0231361, the contents of which are attached as Exhibit A and incorporated by reference herein in their entirety.

The medical tube 100 is a tubular member that defines a passageway 106, which extends through the medical tube 100 from its distal end 102 to its proximal end 104 and provides fluid communication through the medical tube 100. Preferably, the medical tube 100 comprises a material having elastic properties, such as, for example, silicone or some other elastic polymer, such as one of the various thermoplastics. Using an elastic material can help facilitate a fluid-tight seal between the medical tube 100 and fluid fittings such as barbs since an elastic tube will tend to contract over fluid fittings when coupled thereto. Moreover, a flexible, elastic tube 100 can reduce discomfort for the patient compared to tubes of more rigid materials such as polypropylene or polyethylene. However, if desired these and other rigid materials may be used. Moreover, a flexible, elastic tube 100 can reduce discomfort and potential injury to the patient compared to tubes of more rigid materials such as polypropylene, polyethylene, polyimide, metal, etc. However, if desired these and other rigid materials may be used. Moreover, in some examples, the medical tube 100 can comprise a composite of two or more materials such as, for example, a thermoplastic and a metal. Preferably, the medical tube 100 is made from a clear (i.e., transparent or substantially transparent) material, so an operator can visualize any clot material or other debris therein, as well as its removal.

The medical tube 100 can be used to deliver material (e.g., medicine, nourishment, instrumentation, etc.) to the patient's body and/or remove material (e.g., blood, clots, other bodily fluids, etc.) from the patient's body through the passageway 106 of the medical tube 100. In the present example, the medical tube 100 is inserted into and used to drain fluid from the chest cavity of the patient, and so is referred to as a chest tube. However, it is to be appreciated that the medical tube 100 in other examples may be used as, for example, a catheter, a surgical drain tube to drain fluid from other orifices (besides the chest cavity), an endotracheal tube, a feeding tube, a gastric tube, a vascular access tube, a peritoneal tube, a tube to deliver material to or from the alimentary tract, etc.

In some examples, the fluid system 10 can include a drain assembly 200 that is configured to collect material (e.g., bodily fluids, debris, clots, etc.) from the patient's body and/or within the medical tube 100. The drain assembly 200 includes a receptacle 202 fluidly coupled to the proximal end 104 of the medical tube 100 that can receive and collect the drawn material. The receptacle 202 is preferably fluidly coupled to the medical tube 100 to form a closed path of fluid communication between the medical tube 100 and the receptacle 202. The phrase "closed path of fluid communication" as used herein when describing fluid communication between two features is meant to describe a fluid path between the two features wherein exposure to an exterior environment is restricted along the fluid path, thereby preserving a sterile field that may be present within the fluid path. For example, the fluid path between two features may be defined by a tube that is coupled at its two ends to the two features and has no openings along its length that are exposed, either directly or indirectly, to an exterior environment. In some examples, exposure to an exterior environment may be restricted along the fluid path using, for example, a valve or filter. Moreover, in some examples, the fluid path will maintain a pressure relative to an exterior environment.

The drain assembly 200 can be connected to a vacuum source to draw a vacuum on the medical tube 100, or it can be configured to generate a vacuum itself. This vacuum is applied to draw material out of the body cavity and/or medical tube 100 into the receptacle 202. The vacuum generated within the medical tube 100 can help sustain the normal physiologic negative pressure within the body. Moreover, the vacuum generated can be consistent or intermittent. Furthermore, the vacuum source, e.g. the drain assembly 200, can be operated either manually by an operator or automatically to generate the vacuum in response to one or more conditions.

Figure 2:
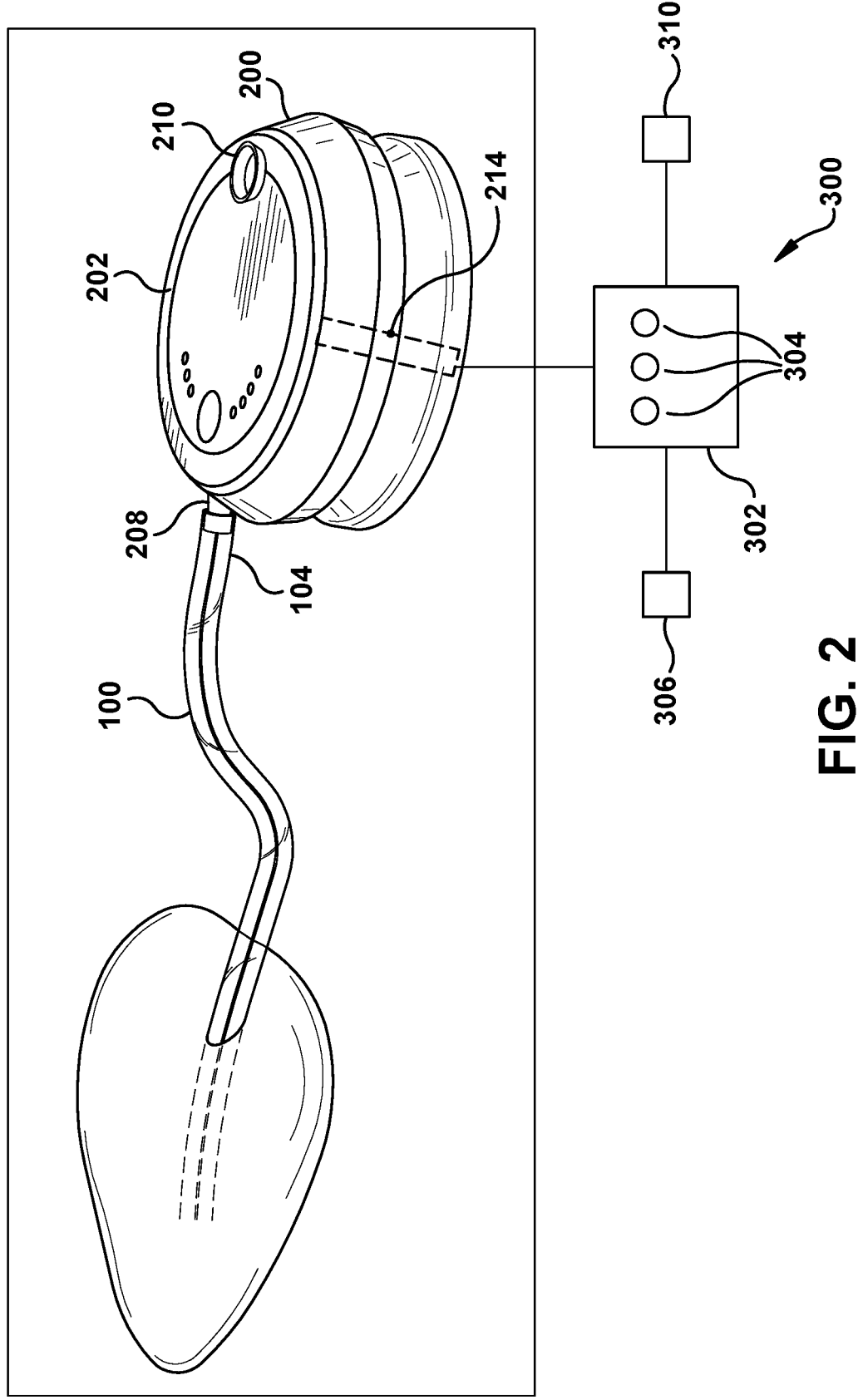
FIG. 2 shows a schematic perspective view of an example drain assembly for the fluid system.

Turning to FIG. 2, one example drain assembly 200 is illustrated having a receptacle 202 that includes an inlet 208 and an outlet 210, the inlet 208 being fluidly coupled to the proximal end 104 of the medical tube 100 to form a closed path of fluid communication between the inlet 208 and the medical tube 100. The inlet 208 may include a check valve that permits material (e.g., blood, clotting, etc.) to drain from the medical tube 100 into the receptacle 202 while inhibiting fluids (e.g., air) and other material from leaving the receptacle 202 through the inlet 208. Moreover, the outlet 210 may include a check valve within that permits material (e.g., air, blood, etc.) to escape the receptacle 202 through the outlet 210 while inhibiting fluids (e.g., air) and other material from entering the receptacle through the outlet 210. The receptacle 202 is collapsible to reduce the volume within the receptacle 202 and force fluid (e.g., air, blood) out of the receptacle 202 through the outlet 210. The receptacle 202 can then expand to increase its internal volume and thereby generate a vacuum that draws material from the medical tube 100 into the receptacle 202 through the inlet 208.

The drain assembly 200 in FIG. 2 further includes one or more actuators 214 operable to collapse and expand the receptacle 202. The actuator 214 in the illustrated example is a linear actuator that can advance and retract to expand and collapse the receptacle 202, respectively. However, the actuator 214 in other examples can include other means such as springs that are operable to collapse and expand the receptacle 202.

In some examples, the fluid system 10 includes a control system 300 that can be configured to automatically operate one or more aspects of the fluid system 10 such as, for example, the drain assembly 200 described above and/or any of the aspects described further below. The control system 300 includes a controller 302 and a control interface 304 (e.g., button(s), switch(es), touchscreen, etc.) that can permit a user to selectively control (e.g., program, operate, etc.) the control system 300. Moreover, the control system 300 can include one or more sensors 306 operatively connected to the controller 302 and configured to detect a particular parameter and send a signal to the controller 302 indicating the detected parameter. Each sensor 306 can be located within the medical tube 100 or some other portion of the fluid system 10. Moreover, the parameter detected by each sensor 306 can be, for example, an orientation (e.g., inclination) of the medical tube 100; a position of a clearance member or some other structure within the medical tube 100; a pressure level, pH level, glucose level, protein level, or redox state of material (e.g., bodily fluid) within the medical tube 100; a blockage within the medical tube 100; a kink in the medical tube 100; an amount of fibrin clot degradation byproducts, endotoxins, bacterial infection byproducts, reactive oxygen species, or hematocrit in the medical tube 100; a temperature, heart rate and rhythm, arrhythmia, respiratory rate, inflammation level, pain level, or oxygen saturation level of the patient; an orientation of the patient in bed; an activity level of the patient; coughing of the patient; the number of steps taken per day by the patient; a type of activity being performed by the patient (e.g., stair climbing); a location of the patient; the length of time a patient has been in a particular area (e.g., the OR, the ICU, the ward, rehab, home, etc.); drainage parameters (e.g., lack of air, minimal fluid per hour, etc.); or any combination thereof. In one embodiment, the one or more sensors 306 can include a GPS tracker such that the patient's location can be tracked (e.g., within an OR, an ICU, a stepdown unit, a rehab unit, a home, an ER, etc.).

The controller 302 of the control system 300 can be in operative communication with a network system to send data collected or generated by the controller 302 via the network to, for example, a system (e.g., a clinician's phone) used to monitor and collect data concerning the patient or the fluid system 100 connected to the patient. For example, the control system 300 can send data corresponding to one or more of the parameters detected by the sensors 306. As another example, the controller 302 can collect data from one or more of the sensors 306 and then execute an algorithm to generate an output based on the collected data that can then be sent over the network. For instance, in one example, the controller 302 can execute an algorithm that determines an expected recovery of a patient based on one or more of the parameters detected by the sensors 306. The expected recovery output may then be sent over the network to a monitoring system (e.g., a clinician's phone). The network can be any system wherein two or more devices are connected via wires or are connected wirelessly (e.g., via Bluetooth or Wi-Fi) such that data can be transferred from one device to another. For example, the network can be a cloud system that shares data (e.g., detected parameter(s)) between two or more devices over the internet.

In some examples, the controller 302 can be configured to activate one or more alarms 310 in response to the parameter(s) detected by the sensor(s) 306. Each alarm 310 can be a light, sound, electronic message (e.g., text or email), or any combination thereof. For instance, in one example, the controller 302 can activate a light that is green, yellow, or red based on the expected recovery of a patient. As another example, the controller 302 can activate an alarm to indicate when a patient may need to move (e.g., walk or get up). In another example, the controller 302 can activate an alarm 310 based on a status of the system (e.g., a pressure within the medical tube 100; a kink in the medical tube 100; an on/off mode of one or more actuators, motors, or other devices of the system; etc.)

As shown in FIG. 2, the controller 302 of the control system 300 can be operatively coupled to the actuator(s) 214 of the drain assembly 200 and configured to automatically operate the actuator(s) 214 in response to one or more of the parameter(s) detected by the sensor(s) 306. In particular, the controller 302 can be configured to automatically operate the actuators 214 to generate or terminate a vacuum within the medical tube 100 in response to the detected parameter(s). The vacuum generated can be consistent, intermittent, and/or variable in pressure.

Figure 3:
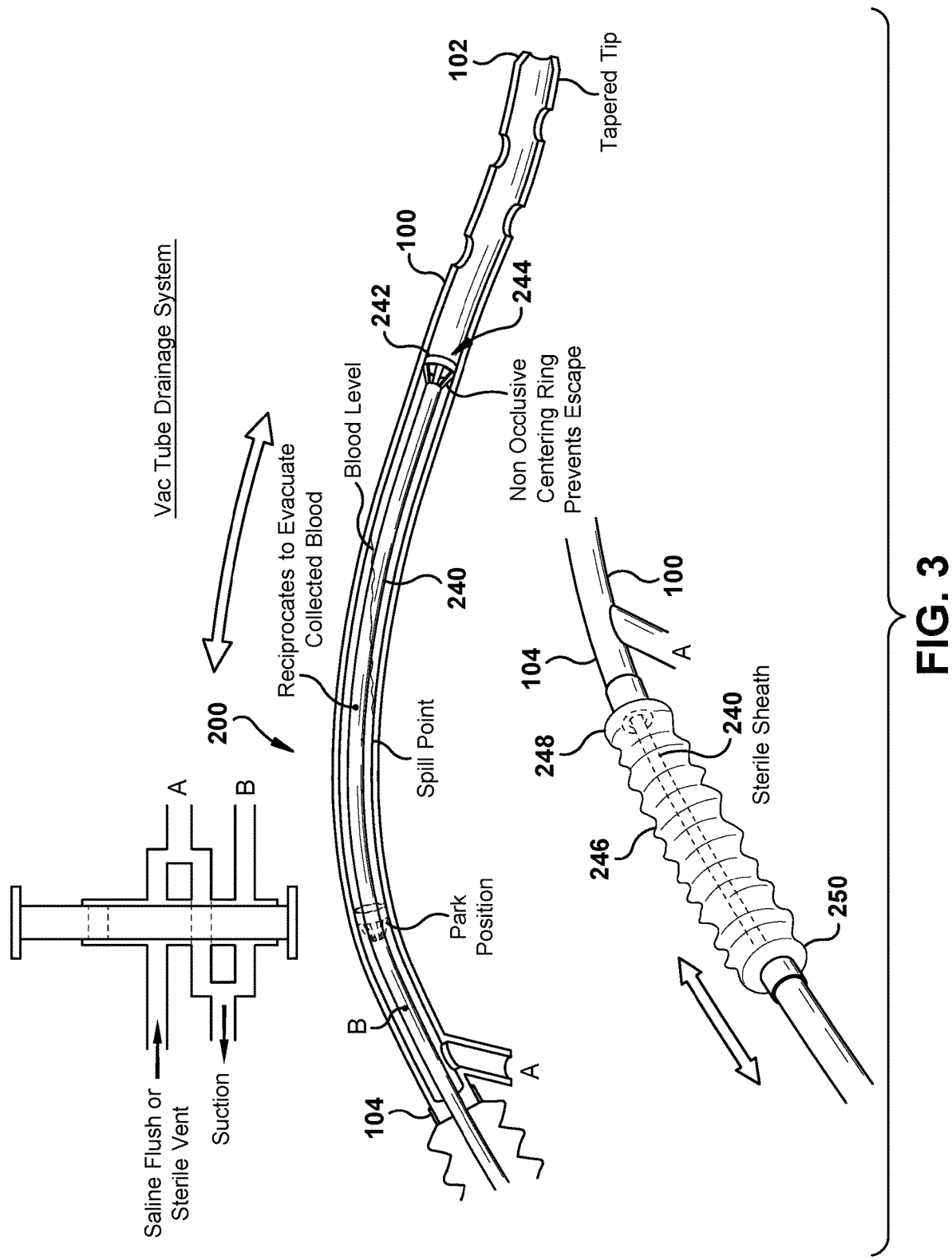
FIG. 3 shows a schematic cross-section and a schematic perspective view of an example vacuum tube for the fluid system.

Turning to FIG. 3, the drain assembly 200 in some examples can include a vacuum tube 240 that is at least partially inserted within the medical tube 100 through the latter's proximal end. A distal end 242 of the vacuum tube 240 can include an inlet 244 for receiving/drawing in material within the medical tube 100. Meanwhile, a proximal end of the vacuum tube 240 can be fluidly coupled to a vacuum source such as, for example, the collapsible receptacle 202 shown in FIG. 2 and described above. The vacuum tube 240 is movable within the medical tube 100 such that the inlet 244 of the vacuum tube 240 can be advanced toward the distal end 102 of the medical tube 100 and retracted toward the proximal end 104 of the medical tube 100 to adjust the position of the vacuum tube's inlet 244 along the passageway 106 of the medical tube 100. Adjusting the position of the inlet 244 can be advantageous, particularly if fluid or other materials to be drawn by the drain assembly 200 are confined to a particular region of the medical tube 100 (e.g., at U-shaped bend in the medical tube 100).

In order to adjust the position of the vacuum tube 240, the drain assembly 200 can include drain tube having or in the form of a collapsible sheath 246 having a distal end 248 and a proximal end 250. The distal end 248 of the sheath 246 can be fixed or fluidly connected to the proximal end 104 of the medical tube 100 and the vacuum tube 240 can extend through the sheath 246 into the medical tube 100. The vacuum tube 240 can be fixed relative to the proximal end 250 of the sheath 246 such that as the sheath 246 is contracted and the proximal end 250 moves toward the distal end 248 of the sheath 246, the vacuum tube 240 and its inlet 244 will advance through the medical tube 100 toward the distal end 102 of the medical tube 100. Conversely, as the sheath 246 expands and the proximal end 250 moves away from the distal end 248 of the sheath 246, the vacuum tube 240 and its inlet 244 will retract and be withdrawn from the distal end 102 of the medical tube 100.

The sheath 246 described above can be expanded and/or contracted either manually or automatically using a control system such as, for example, the control system 300 described above. In particular, the controller 302 of the control system 300 can be operatively coupled to an actuator (e.g., a linear actuator) that can be selectively operated to expand and/or contract the sheath 246 in response to the parameter(s) detected by the sensor(s) 306 of the control system 300.

As fluid or other material resides in or is transferred through the medical tube 100, some material (e.g., debris, clots, etc.) can accumulate within the medical tube 100, thereby obstructing the transfer of material and/or vacuum through the medical tube 100. The vacuum described above can sometimes be sufficient to draw this accumulated material through the medical tube 100 into the receptacle 202 unaided by additional intervention. However, in some instances it can be helpful to have additional intervention(s) that can disrupt (e.g., collect, dislodge, move, break apart, penetrate, etc.) the accumulated material to help clear the medical tube 100 of obstruction.

Figure 4:
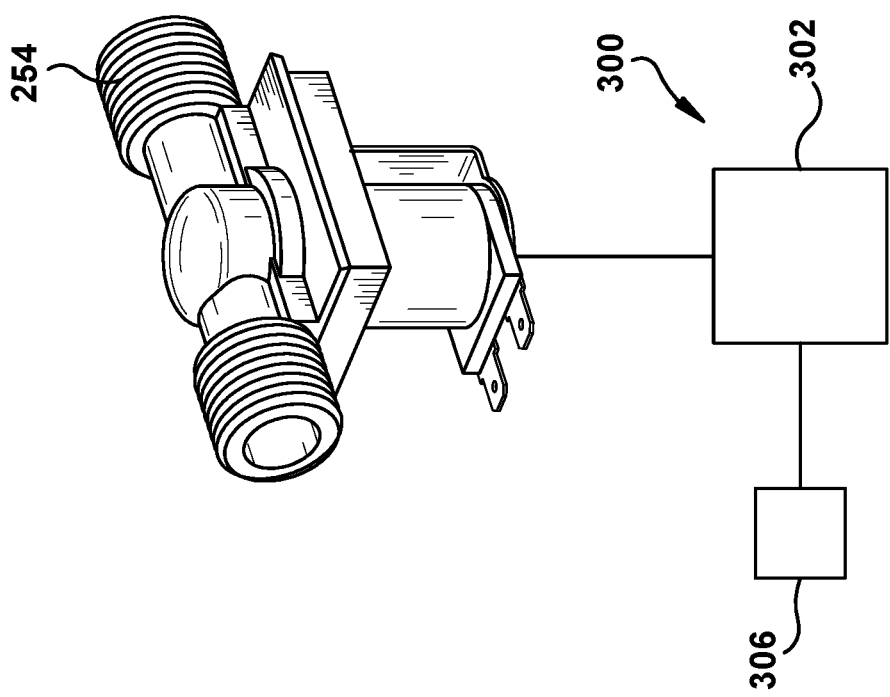
FIG. 4 shows a schematic perspective view of an example valve assembly for the fluid system.

For instance, turning to FIG. 4, the drain assembly 200 in some examples can include one or more valves 254 configured to pulsate the vacuum generated within the medical tube 100 in order to facilitate removal of material accumulated within the medical tube 100. Each valve 254 can be located, for example, within the medical tube 100, within the inlet 208 of the receptacle 202, or anywhere else along the fluid path of communication between the medical tube 100 and the vacuum source (e.g. receptacle 202). Each valve 254 can be selectively opened and closed, either manually or automatically, to open and close fluid communication between the medical tube 100 and the vacuum source to thereby pulsate the vacuum generated within the medical tube 100. For instance, in some examples, each valve 254 can be operatively coupled to the controller 302 of the control system 300 described above, which can automatically open and close the valve 254 to pulsate vacuum in response to one or more parameters (e.g., tube blockage) detected by the sensor(s) 306 of the control system 300. Pulsating the vacuum within the medical tube 100 can help generate turbulence within the medical tube 100, which can disrupt material accumulated within the passageway 106 of the medical tube 100 and thereby facilitate removal of the accumulated material.

Returning to FIG. 1, in some examples the fluid system 10 can include a clearance wire assembly 400 that can be actuated (e.g., translated, rotated, vibrated, oscillated, etc.) within the passageway 106 of the medical tube 100 to disrupt material accumulated within the passageway 106 and help clear the medical tube 100 of obstruction. The clearance wire assembly 400 includes an elongated guide wire 402 and in some examples, can include one or more clearance members coupled to the guide wire 402 that can facilitate disruption of material accumulated within the passageway 106. Preferably, the guide wire 402 comprises a material having sufficient flexibility such that it can negotiate bends in the medical tube 100 during translation (e.g., insertion) of the wire assembly 400 within the medical tube 100. In addition, the guide wire 402 preferably comprises a material having sufficient stiffness or rigidity such that the guide wire 402 and any clearance members coupled thereto can disrupt (e.g., move) the accumulated material without causing the wire 402 to kink or double back on itself. For instance, the guide wire 402 can comprise nickel-titanium alloys (e.g., nitinol), stainless steel, titanium, shape memory alloys, super alloys, cobalt-chromimum alloys (e.g., Elgiloy®), and/or other alloys. In some examples, the guide wire 402 can comprise one or more polymers, such as PEEK, polyimide, or other polymers. The guide wire 402 can comprise combinations/composites of two or more materials such as, for example, one or more alloys and one or more polymers. Moreover, any clearance member coupled thereto can comprise similar material(s) and in some examples, can be formed by the guide wire 402 itself.

With reference now to FIGS. 5-14, various embodiments of the clearance wire assembly 400 will now be described.

Figure 5:
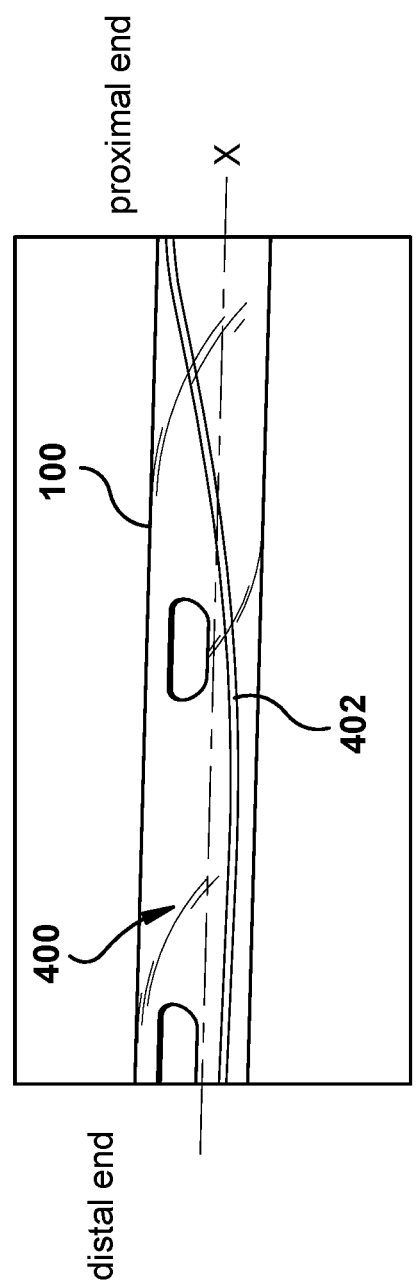
FIG. 5 shows a partial view of the medical tube with one example clearance wire assembly for the fluid system.

One embodiment of the clearance wire assembly 400 is illustrated in FIG. 5, wherein the guide wire 402 is in the form of a planar ribbon that extends longitudinally through the passageway 106, and is wound such that it spirals about an axis X of the medical tube 100. The clearance wire assembly 400 in this embodiment may not include an additional clearance member (the clearance wire itself may act as the clearance member) and can be moved within the passageway 106 by, for example, rotating the clearance wire assembly 400 about the axis X, advancing the clearance wire assembly 400 toward the distal end 102 of the medical tube 100, and/or retracting the clearance wire assembly 400 toward the proximal end 104 of the medical tube 100.

Figure 6:
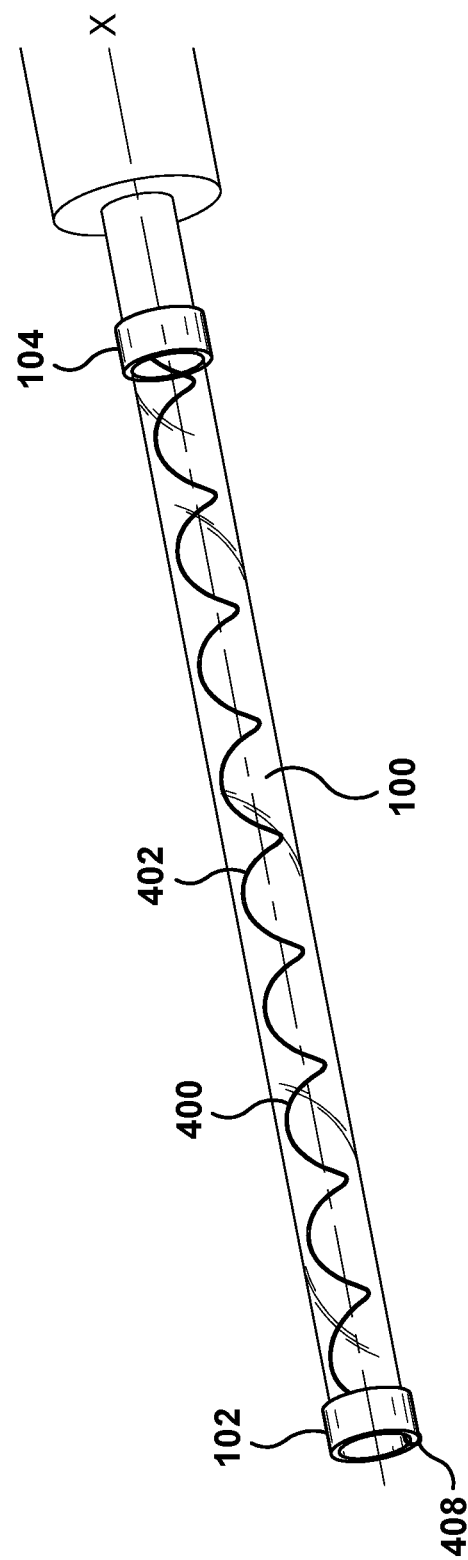
FIG. 6 shows a schematic perspective view of the medical tube with a second example clearance wire assembly.

Another embodiment of the clearance wire assembly 400 is illustrated in FIG. 6, wherein the guide wire 402 has a circular spiral conformation when viewed along axis X and spirals about the axis X of the medical tube 100. However, other cross-sections and configurations are possible in other examples. The clearance wire assembly 400 in this embodiment can include a hook 408 at its distal end that hooks onto the distal end 102 of the medical tube 100. A cap (not shown for clarity) may be provided that covers the distal end 102 of the medical tube 100 and the hook 408 to allow free movement of the hook 408 about the distal end 102 without interference from body structures or tissue. The proximal end of the clearance wire assembly, meanwhile, can be coupled to the proximal end 104 of the medical tube 100 or some other portion of the fluid system 10 that is proximal to the hook 408. The clearance wire assembly 400 can be actuated within the passageway 106 by, for example, rotating the clearance wire assembly 400 about the axis X continuously or intermittently, either in the same direction or in an oscillating manner. As the clearance wire assembly 400 rotates, the hook 408 will move about the perimeter of the medical tube's distal end 102 so that the distal end of the clearance wire assembly 400 does not bind and rather moves freely with the remainder of the clearance wire assembly 400. Rotation of the wire assembly 400 in this embodiment in FIG. 6 in the proper direction can produce an auger effect that will tend to convey accumulated debris within the passageway 106 proximally, toward the exit end of the medical tube 100.

Figure 7:
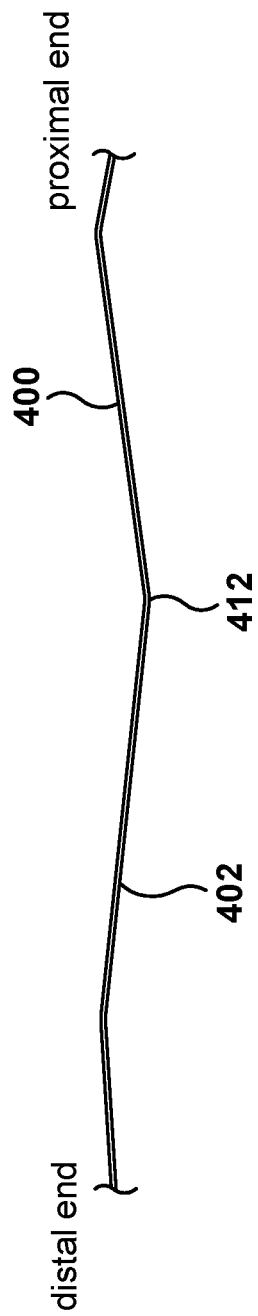
FIG. 7 shows a partial view of a third example clearance wire assembly.

Another embodiment of the clearance wire assembly 400 is illustrated in FIG. 7, wherein the guide wire 402 has a circular cross-section and has one or more bends 412 along its length. However, other cross-sections and configurations are possible in other examples. In some examples, a distal end of the clearance wire assembly 400 will reside within the distal end 102 of the medical tube 100 and/or some other portion of the medical tube 100 and will be free to move (e.g., rotate) within the medical tube 100. The proximal end of the clearance wire assembly 400 can then be rotated either continuously or intermittently in the same direction or in an oscillating manner. In other examples, the clearance wire assembly 400 can be fixed at its distal end to the distal end 102 of the medical tube 100 and/or some other portion of the medical tube 100. The clearance wire assembly 400 can then be actuated by, for example, rotating the proximal end of the clearance wire assembly 400 about the longitudinal axis of the medical tube 100 (e.g., the X axis in FIG. 6) in an oscillating manner, either continuously or intermittently. Since the distal end of the wire assembly 400 is fixed, the distal end will resist movement of the wire assembly 400 and bias the wire assembly 400 toward a natural, resting position. This bias of the wire assembly 400 can help generate a whipping action as the portion of the clearance wire assembly 400 inside the passageway 106 oscillates about the axis X that can facilitate disruption of material accumulated within the medical tube 100. In one embodiment, the wire has no set bends but has length that is longer than than required to connect to the fixed points at its distal and proximal ends such that the excess material partially coils the wire within the tube. When the proximal end is actuated, by rotation or other means, a whipping action results.

Figure 8:
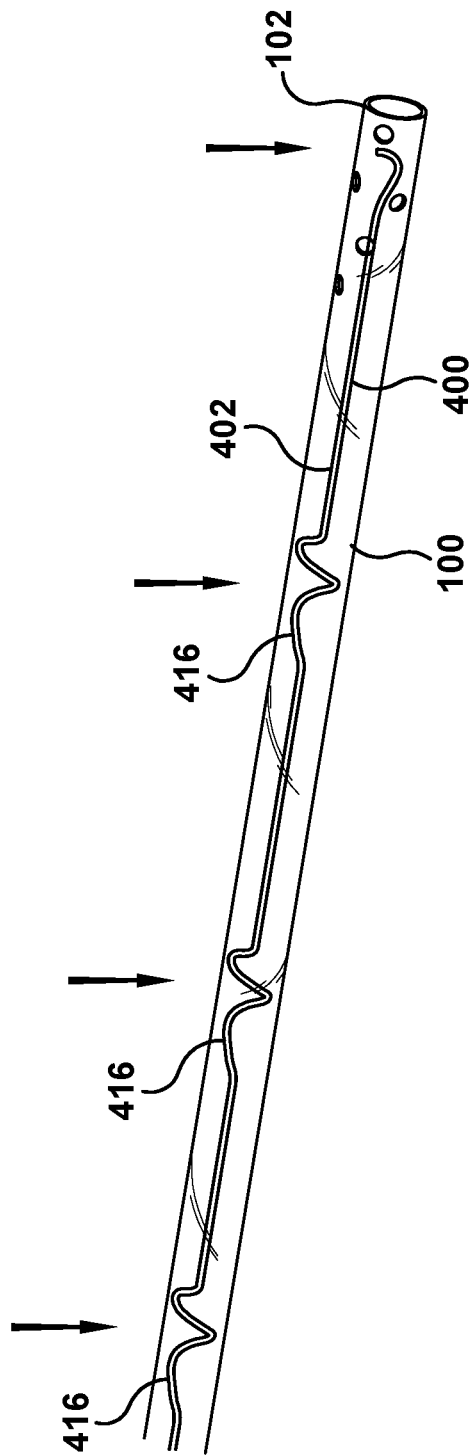
FIG. 8 shows a schematic perspective view of the medical tube with a fourth example clearance wire assembly.

Another embodiment of the clearance wire assembly 400 is illustrated in FIG. 8, wherein the guide wire 402 has a circular cross-section and the wire assembly 400 includes a plurality of clearance members 416 coupled to or forming part of the wire 402 such that the clearance members 416 are spaced along a length of the wire 402, preferably at a constant interval. In a preferred embodiment, each clearance member 416 is formed by bending a portion of the wire 402 into a spiral shape that preferably has a comparable or slightly smaller overall diameter than the inner diameter of the medical tube 100. As the clearance wire assembly 400 is advanced or retracted through the medical tube 100, each clearance member 416 can engage the inner surface of the medical tube 100 to help disrupt any material that may have accumulated on the inner surface. By having multiple clearance members 416 spaced along the wire 402, the clearance wire assembly 400 can engage multiple portions of the medical tube's inner surface while translating through the medical tube 100. Moreover, the wire 402 can be actuated less than the entire length of the medical tube 100 such that repeated actuation conveys material proximally through the entire length of the tube 100 via the plurality of clearance members 416.

It is to be appreciated that the clearance members 416 of the wire assembly 400 can have alternative configurations in other examples. For instance, the clearance members 416 may be irregularly spaced along the wire 402 and/or the clearance members 416 may be separate elements that are separately coupled to the wire 402. Moreover, the clearance members 416 may have alternative shapes and/or sizes in some examples.

Figure 9:
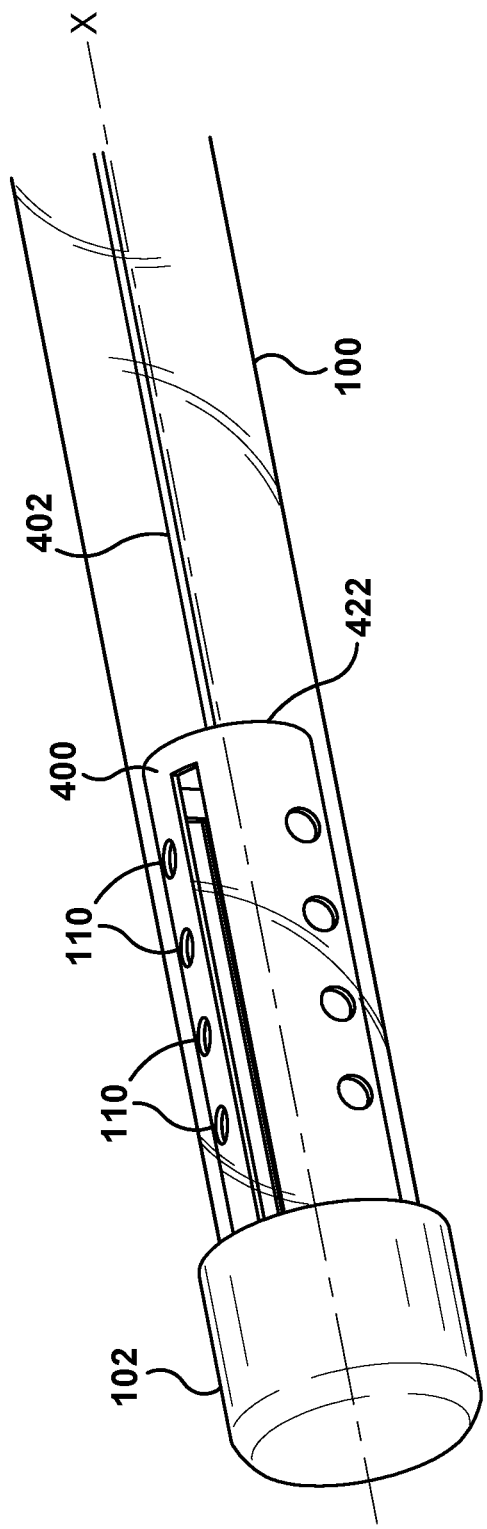
FIG. 9 shows a schematic perspective view of the medical tube with a fifth example clearance wire assembly.

Another embodiment of the clearance wire assembly 400 is illustrated in FIG. 9, wherein a cylindrical clearance member 422 is coupled to the guide wire 402. In this embodiment, the medical tube 100 can include one or more apertures 110 that extend through its side wall at a portion of the medical tube 100 that is located within the patient's body. The cylindrical clearance member 422 is aligned co-axially within the medical tube 110 and preferably has an outer diameter that is comparable to or slightly smaller than the inner diameter of the medical tube 100. In some examples, the clearance wire assembly 400 can be translated along the medical tube's axis X toward the distal end 102 of the medical tube 100 such that the clearance member 422 traverses the one or more apertures 110 and performs a guillotine action that can disrupt material accumulated in or adjacent the apertures 110 and temporarily block the transfer of material through the apertures 110. Guillotined material that has thus been separated from where it adhered to the medical tube 100 or its apertures 110 then can be suctioned out from the medical tube via its proximal end 104. The clearance wire assembly 400 can then be translated (either toward the distal end 102 or the proximal end 104 of the medical tube 100) until the clearance member 110 is at a position that does not obstruct the apertures 110, thereby permitting material to resume transfer through the apertures 110.

In addition or in alternative to translating the clearance member 422, in some examples the cylindrical clearance member 422 can be rotated about the medical tube's axis X while the clearance member 422 is located at the section of the medical tube 100 having the apertures 110. In such examples, the clearance member 422 can include an aperture (e.g., slot) 423 such that as the clearance member 422 is rotated, the aperture 423 of the clearance member 400 will periodically align with the medical tube apertures 110 and permit fluid to transfer through the apertures 110, 423.

Figure 10:
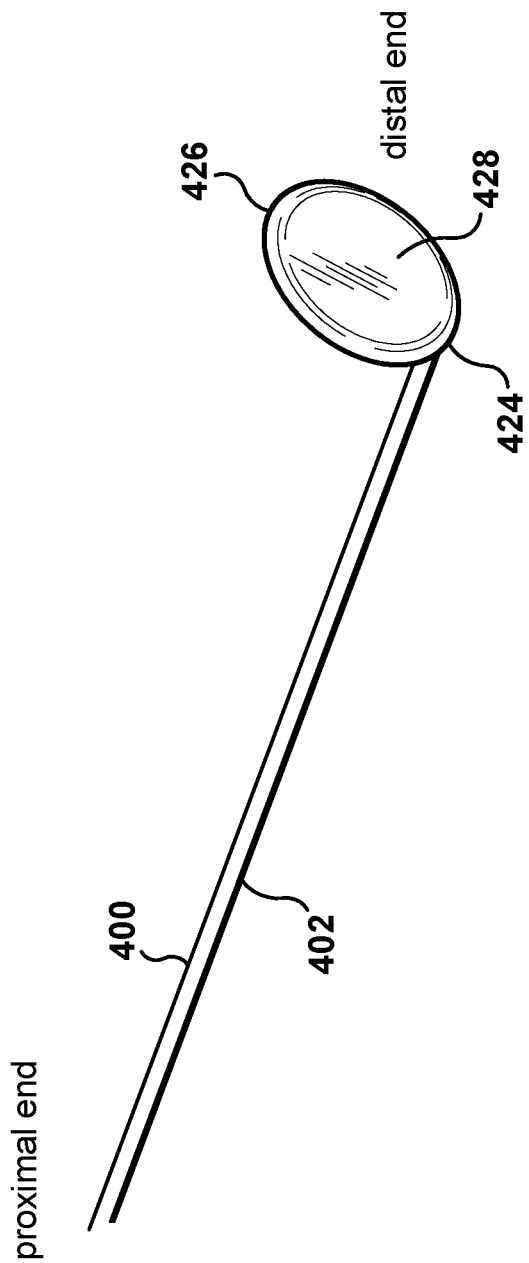
FIG. 10 shows a partial perspective view of a sixth example clearance wire assembly.

Another embodiment of the clearance wire assembly 400 is illustrated in FIG. 10, wherein the clearance member 424 is a generally circular disc coupled at the distal end 102 the guide wire 402, though the clearance member 424 may be coupled to other portions of the wire 402 in other examples. The circular clearance member 424 is aligned co-axially within the medical tube 100 (though it may be offset in some examples) and preferably has an outer diameter comparable to or slightly smaller than the inner diameter of the medical tube 100. Moreover, the circular clearance member 424 can have a solid or perforated center that inhibits or fully blocks the transfer of material through the circular clearance member 424. In some examples, the center may comprise a one-way valve that will permit material transfer therethrough during translation toward the distal end 102 of the tube 100 so as not to push material back into the body.

The circular clearance member 424 can be formed by looping a portion of the guide wire 402 to form a circular frame 426 of the clearance member 424. Filler material 428 can then be attached (e.g., adhered or welded) to the circular frame 426 to plug the center of the clearance member 424. In other examples, the circular clearance member 424 can be a disc that is separately formed from the guide wire 402 (e.g., via injection molding, casting, stamping, etc.) and then attached to the guide wire 402.

It is to be appreciated that the clearance member 424 can have alternative configurations in other examples. For instance, the clearance member 424 may have a substantially smaller diameter and/or may be a separate element that is separately coupled to the wire 402. Moreover, the clearance member 424 may have a non-circular shape in some examples such as, for example, a square shape or some other polygonal shape.

Figure 11A:
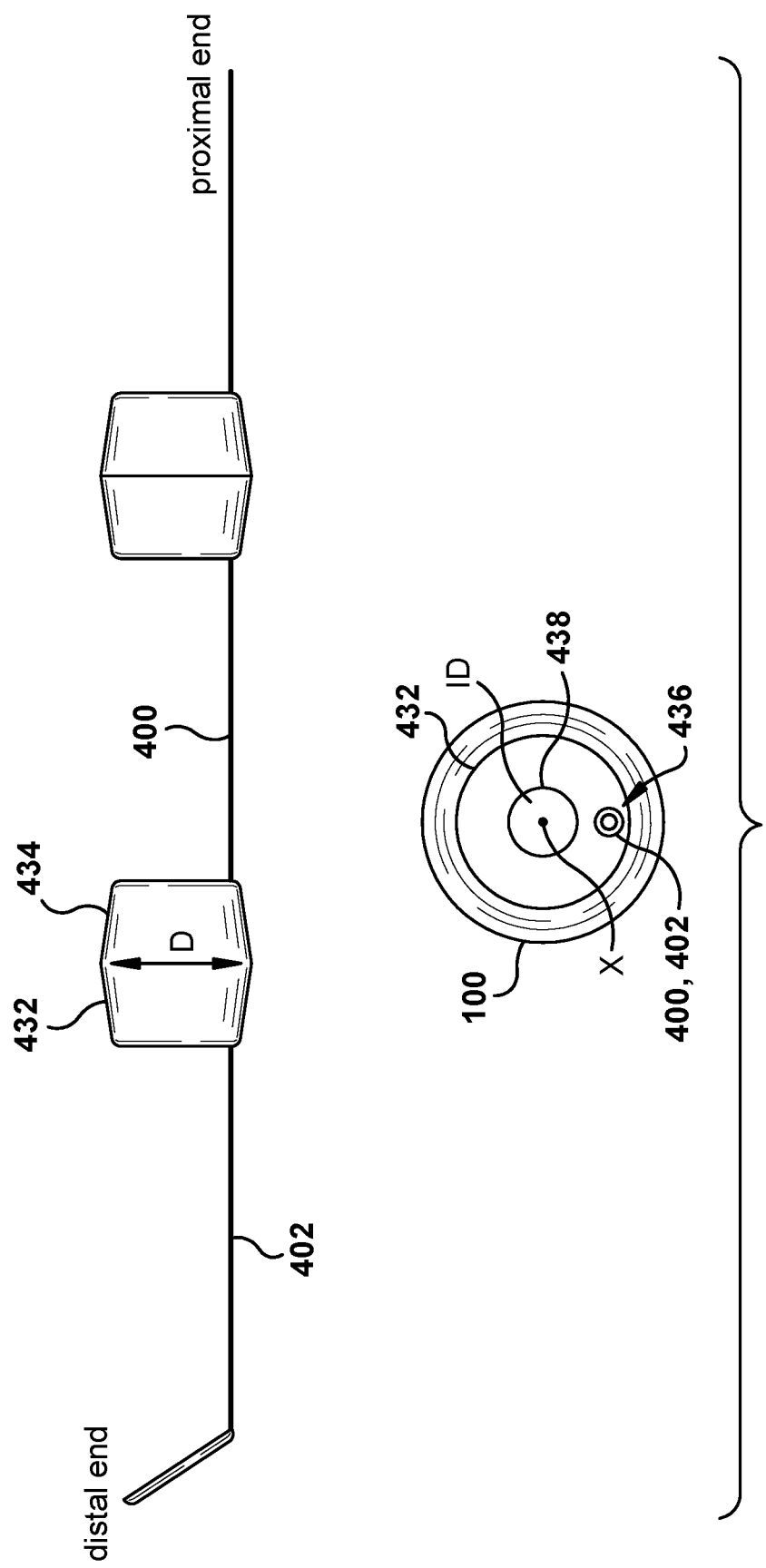
FIG. 11A shows a schematic side view and a schematic cross section of the medical tube with a seventh example clearance wire assembly.
Figure 11B:
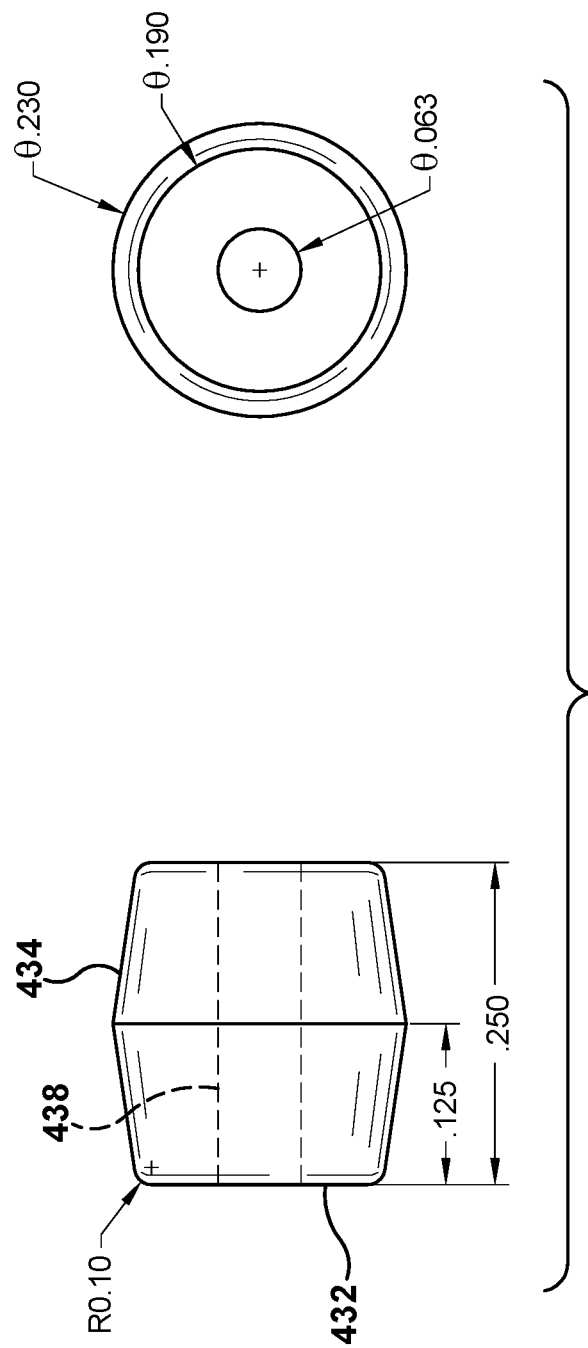
FIG. 11B shows a side view and a front view of an example bead that is part of the seventh example clearance wire assembly.

Another embodiment of the clearance wire assembly 400 is illustrated in FIGS. 11A & 11B, wherein a clearance member 432 in the form of a bead is coupled to the guide wire 402. The bead 432 includes an outer surface 434 that is circular in cross-section and has a diameter than varies along the length of the bead 432. In particular, the diameter is greatest at a center of the bead 432 and is smallest at the proximal and distal ends of the bead 432. Preferably, the diameter of the bead 432 at its center is comparable to or slightly smaller than the inner diameter of the medical tube 100, thereby forming an interface at the center between the bead 432 and the inside of the medical tube 100. By varying the diameter of the bead 432 along its length, the surface area of the bead 432 that engages the medical tube's inner surface can be reduced (compared to a cylindrical member of the same length and having a constant diameter comparable to the ID of the medical tube 100), and friction between the bead 432 and the medical tube 100 can be mitigated. However, in some examples, the bead 432 may have a constant diameter along its length. In a preferred embodiment, there is a slight gap between the bead 432 and the inner diameter of the medical tube 100 such that fluid will be conveyed in part due to surface tension effects at the interface between the bead 432 and the medical tube 100.

The bead 432 can be coupled to the distal end of the wire 402 or some other portion of the wire 402. Moreover, the bead 432 can be integrally formed with the wire 402 or the bead 432 can be separately formed and then attached to the wire 402. In the illustrated example, the bead 432 includes a through-hole 436 that is aligned (e.g., parallel) with the medical tube's axis X and the bead 432 is coupled to the wire 402 such that a portion of the wire 402 passes through the through-hole 436. The bead 432 can be coupled by molding the bead 432 directly onto the wire 402 or by molding the bead 432 separately from the wire 402 and then inserting the wire 402 through the through-hole 436.

In some examples, the bead 432 can include a through-hole 438 that is aligned (e.g., coaxial) with the medical tube's axis X and permits material (e.g., blood or other bodily fluids) to transfer through the bead 432 as the wire assembly 400 is translated through the medical tube 100 or at rest. This can mitigate resistance applied to the bead 432 during translation. This can also serve to allow free flow of material through the bead 432 when it is at rest in any portion of the medical tube 100. It can also serve to equalize pressure on the distal and proximal sides of the bead 432, especially when it is translating. Although fluid may be free to flow through the hole 438, the body of the bead 432 surrounding the hole 438 can still provide a clearance function as the bead 432 is actuated through the medical tube 100. In some examples, a one-way valve can be provided within the hole 438 that will open during advancement of the bead 432 and close during retraction of the bead 432 through the medical tube 100.

In some embodiments the bead 432 may have a relatively large through-hole 432 relative to its outer diameter such that the bead 432 becomes a thin walled configuration, as shown in FIG. 11C.

In other examples, the bead 432 may be substantially solid so as not to permit the transfer of material through the bead 432. In such examples, the bead 432 may still include the through-hole 436 discussed above for coupling the bead 432 to the wire 402. Preferably, the through-hole 436 is fit to the wire 402 such that fluid communication through the hole 436 is substantially inhibited by the presence of the wire 402 within the hole 436.

Figure 11D:
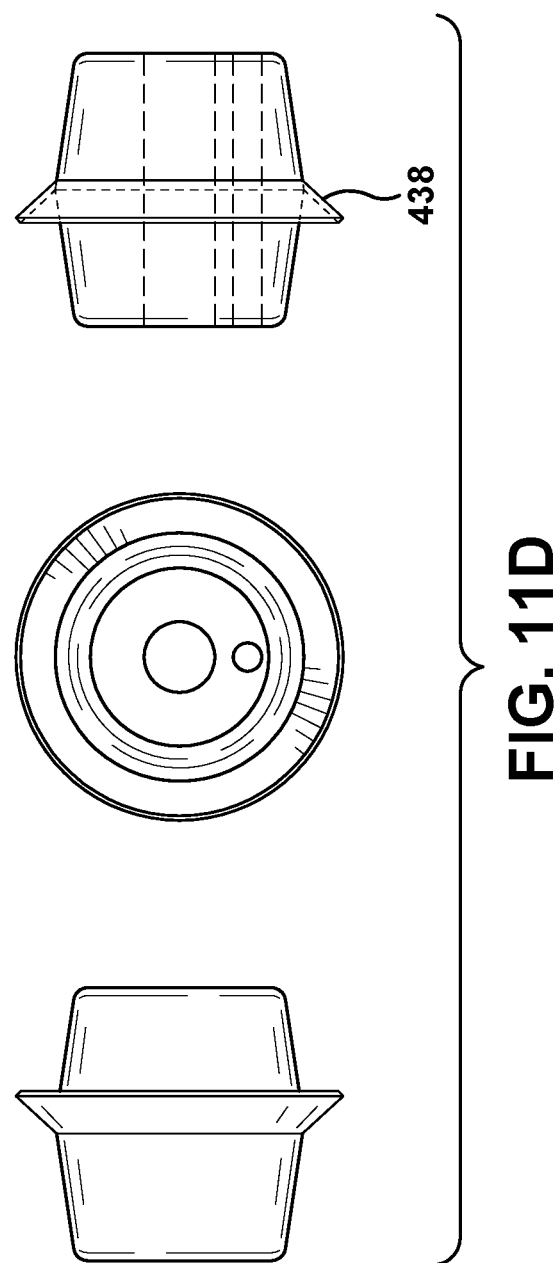
FIG. 11D shows a side view, top view and front view of yet another example bead that is part of the seventh example clearance wire assembly.

In some examples, the bead 432 may have a skirt 438 extending from the body of the main body of the bead 432, as shown in FIG. 11D. The skirt 438 may be made from a flexible material such as an elastomer or a wire mesh. The skirt 438 can engage the inner diameter of the medical tube 100 to produce a squeegee effect that moves fluid an debris along the tube 100 with the bead 432. In other embodiments the skirt 438 may be attached to other clearance members or directly to the guide wire 402.

Figure 11E:
FIG. 11E shows a clearance wire assembly with multiple beads.
Figure 11F:
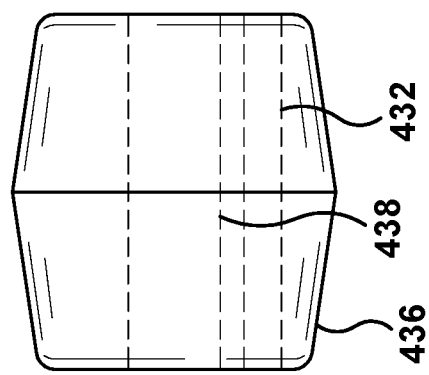
FIG. 11F shows a side view of still yet another example bead that is part of the seventh example clearance wire assembly.

In some embodiments, one or more beads 432 may be coupled to the wire 402, as shown in FIG. 11E. Moreover, one or more beads 432 may be coupled in combination with other clearance member configurations. In one embodiment the distal end 102 of the medical tube 100 and any perforations in the medical tube 100 are sized such that the bead 432 cannot escape the medical tube 100 through the distal end 102 or perforations. In particular, the distal end 102 of the medical tube 100 can be tapered to a smaller diameter or can include a tip that is sufficiently smaller than the bead 432 to prevent it from leaving the distal end 102 of the tube 100. Another example bead 432 is illustrated in FIG. 11F.

Figure 12A:
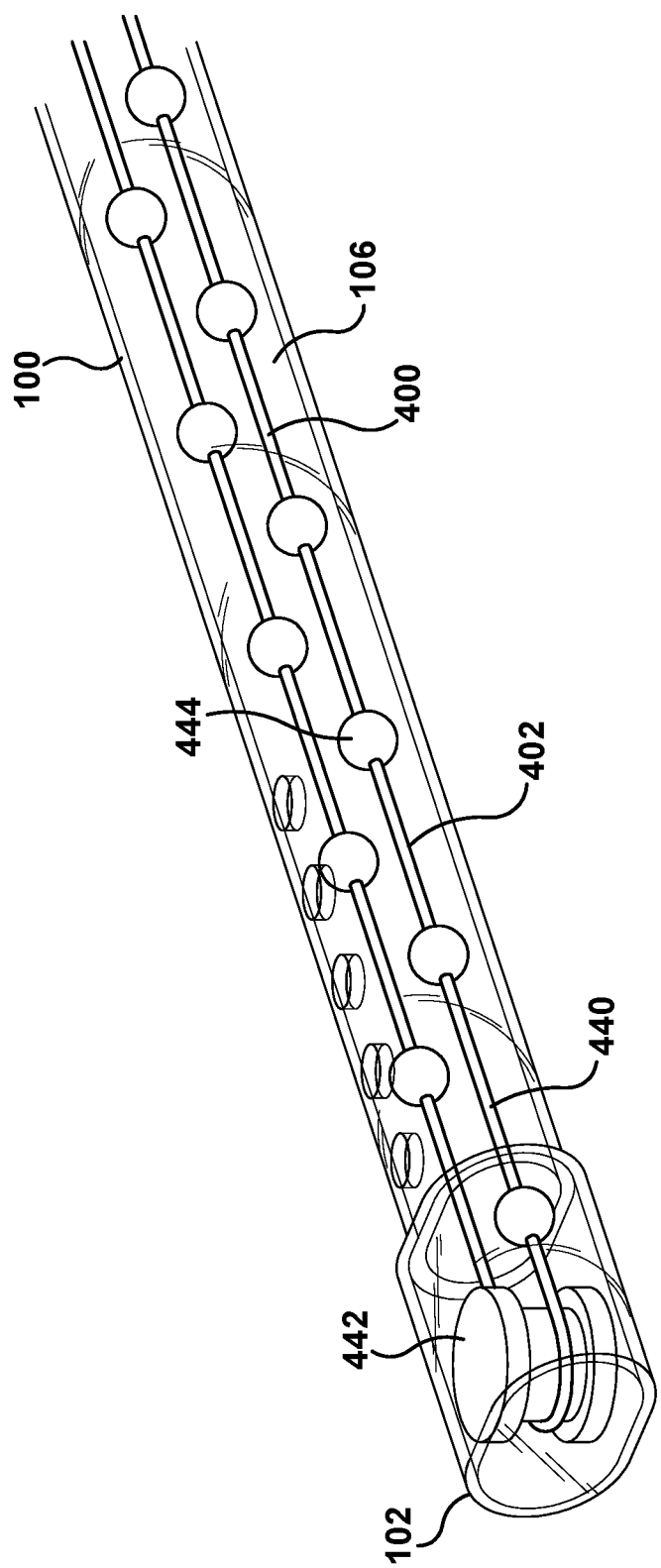
FIG. 12A shows a schematic perspective view of the medical tube with an eighth example clearance wire assembly that has spherical clearance members.

Another embodiment of the clearance wire assembly 400 is illustrated in FIG. 12A, wherein the clearance wire assembly 400 is in the form of a conveyor loop that extends through the passageway 106 of the medical tube 100 and can move or circulate in a conveyor motion. In this embodiment, the clearance wire assembly 400 includes a conveyor belt 440 (e.g., the guide wire 402) and one or more pulleys 442 located within the medical tube 100 or some other portion of the fluid system 10 about which the belt 440 can be wound in order to yield its circuitous, never-ending travel path. The belt 440 may be a wire or monofilament. Moreover, the belt 440 can be ribbon-shaped such that the belt 440 has a rectangular cross-section. Alternatively, the belt 440 can be wire-shaped such that the belt 440 has a circular cross-section. The wire assembly 400 can be moved such that the belt 440 conveys continuously or intermittently about the pulleys 442. Moreover, wire assembly 400 can be moved such that the belt 440 conveys at all times in the same direction (e.g., clockwise) or in alternating directions (e.g., clockwise and then counter-clockwise).

The conveyor-type wire assembly 400 in FIG. 12A can include one or more clearance members 444 coupled to the belt 440 that can be conveyed along the aforementioned circuitous path through the passageway 106 as the belt 440 rounds the pulleys 442 along its circuitous path. The clearance members 444 may be spaced approximately one inch apart from each other, though other distances are possible in other examples. Moreover, the clearance members 444 can be spherical or may comprise other shapes such as, for example, flat discs, hemi-spheres, or cups. For instance, the clearance members 444 shown in FIG. 12A comprise spherical beads that are connected to the belt 440. In another example, as shown in FIG. 12B, the clearance members 444 may comprise cups, wherein each cup 444 is arranged such that its opening is directed toward the cup's direction of travel.

Figure 13:
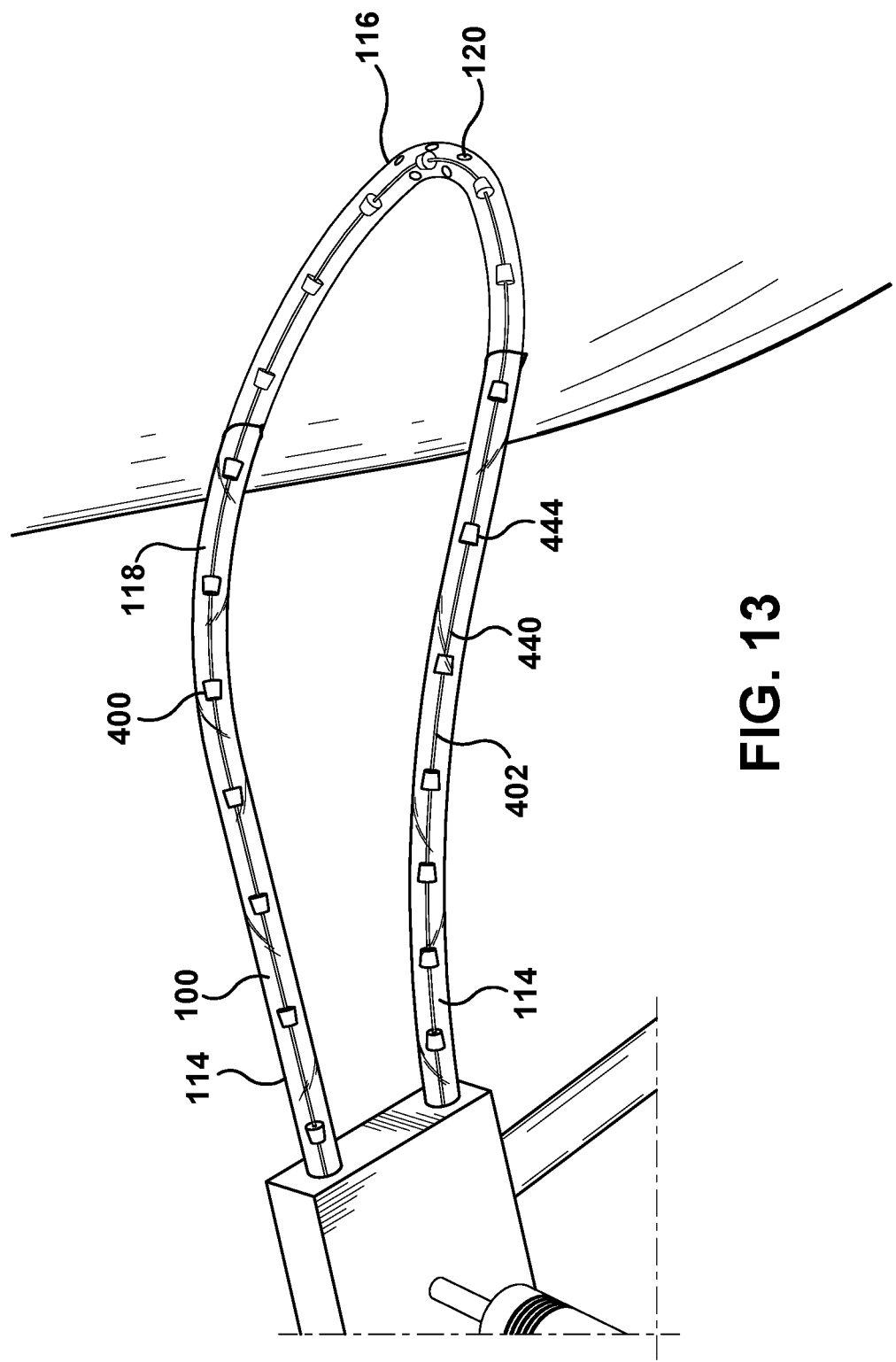
FIG. 13 shows a schematic perspective view of a ninth example clearance wire assembly.

Another conveyor-type embodiment of the clearance wire assembly 400 is illustrated in FIG. 13, wherein the wire assembly 400 similarly comprises a belt 440 and clearance members 444 as described above. In this embodiment, the medical tube 100 has two proximal portions 114 that will reside outside of the patient's body and a distal portion 116 that will reside in the patient's body. The distal portion 116 will connect the two proximal portions 114 to form part of a continuous loop 118 that runs through the patient. Moreover, the distal portion 116 can include one or more apertures 120 for material to transfer between the medical tube 100 and the patient's body. The medical tube 100 may penetrate the patient's body in two separate locations so that the distal portion 116 can reside within the patient's body. Alternatively, the same incision site may be used for both ends of the tube 100.

The belt 440 of the clearance wire assembly 400 in FIG. 13 can be conveyed continuously or intermittently about the continuous loop 118, either in the same direction or in alternating directions.

As is apparent from the description above, the clearance wire assembly 400 can have a variety of different configurations, any of which can be actuable (e.g., movable) through the medical tube 100 to facilitate disruption of material accumulated within the medical tube 100. With reference now to FIGS. 14-22, various drive systems will now be described that can facilitate movement of the clearance wire assembly 400 in the manners discussed above.

Figure 14:
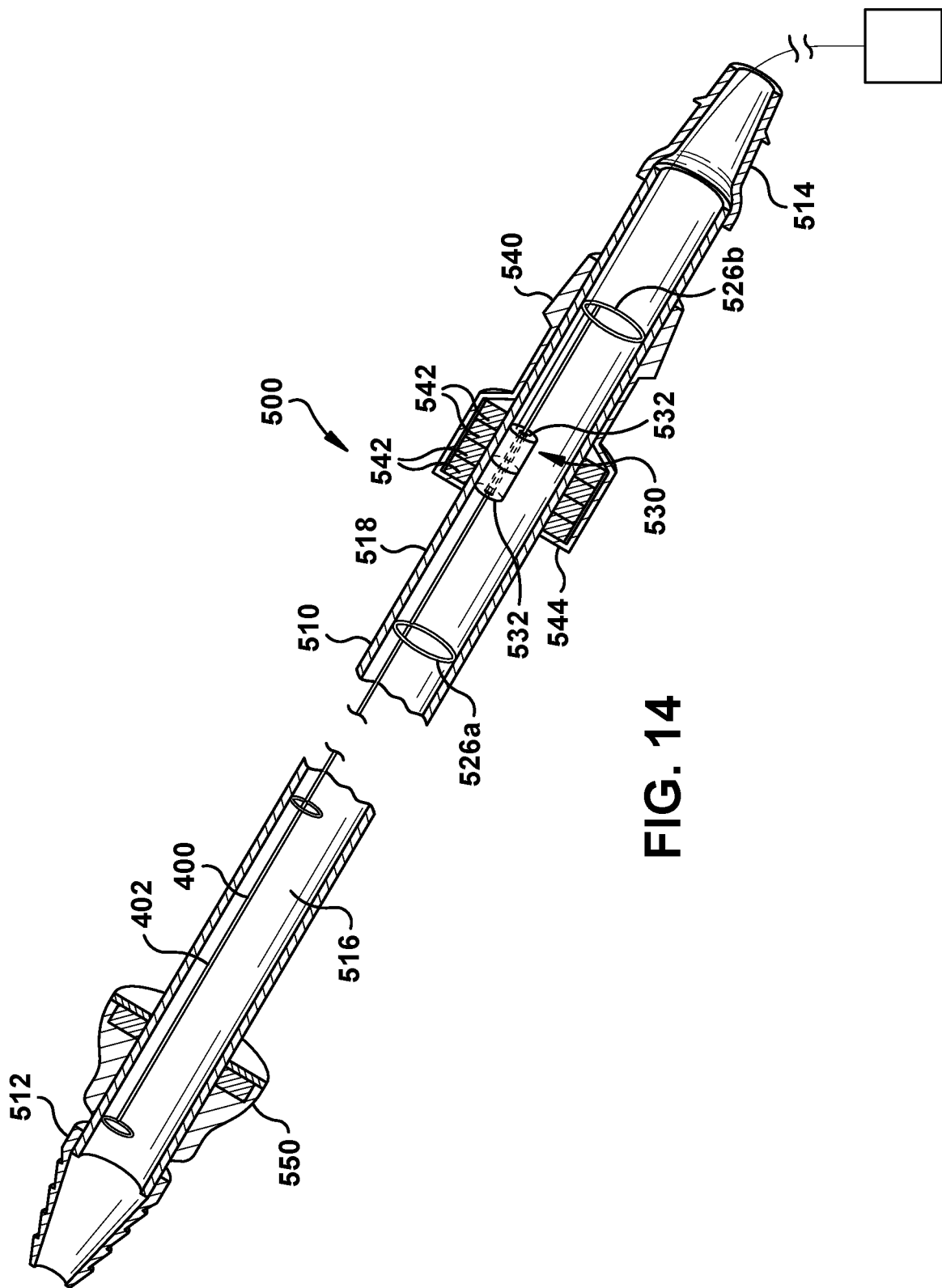
FIG. 14 shows a schematic cross section of one example drive system for a clearance-wire assembly of the fluid system.
Figure 15:
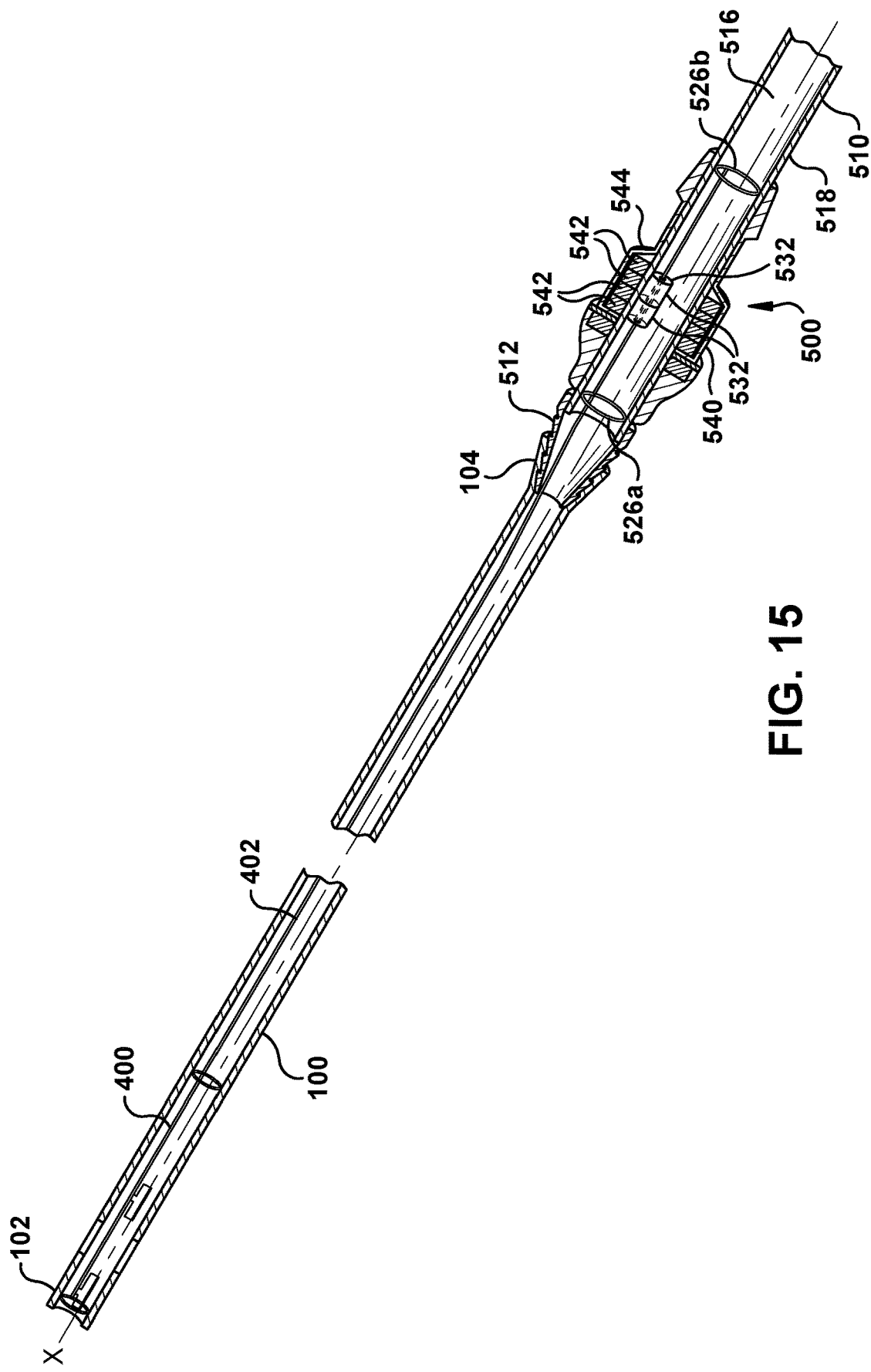
FIG. 15 shows another schematic cross section of the drive system shown in FIG. 14.

As shown in FIGS. 14 & 15, the fluid system 10 in some embodiments can include a magnetic drive system 500 that is operable to actuate the clearance wire assembly 400. One form of actuation that can be provided by the magnetic drive system 500 is translation of the clearance wire assembly 400 back and forth through the medical tube 100 along the axis X of the medical tube 100. Another form of actuation that can be provided by the magnetic drive system 500 is rotation of the clearance wire assembly 400 within the medical tube 100 about the axis X. The magnetic drive system 500 can correspond to the clearance device disclosed in U.S. Pat. No. 7,951,243, the contents of which are attached as Exhibit B and incorporated by reference herein in their entirety.

The magnetic drive system 500 includes a guide tube 510 having a distal end 512 that is fluidly coupled to the proximal end 104 of the medical tube 100 and a proximal end 514 that is fluidly coupled to a suction source such as, for example, the receptacle 202 of the drain assembly 200 shown in FIG. 2. The guide tube 510 defines a guide-tube passageway 516 and an outer circumference 518.

The drive system 500 further includes a magnetic guide 530 having one or more first magnetic elements 532 that are fixedly coupled to the guide wire 402 of the clearance wire assembly 400. The first magnetic elements 532 can be permanent magnets such as, for example, neodymium magnets (N5-N52). Alternatively, the first magnetic elements 532 may be metal elements having magnetic properties, which are not necessarily permanent magnets. As used herein, a metal element has magnetic properties if it is capable of being attracted by a permanent magnet via magnetic forces.

The drive system 500 further includes a shuttle member 540 disposed over, and preferably in contact with, the outer circumference 518 of the guide tube 510. The shuttle member 540 has a through bore preferably having a diameter substantially corresponding to the outer circumference 518, such that the shuttle member 540 can slidably and smoothly translate along the length of the guide tube 510 with the guide tube 510 received through its bore. The shuttle member 540 includes one or more second magnetic elements 542 embedded or enclosed within a shuttle housing 544. Optionally, the second magnetic element(s) 542 can form all or part of the housing 544. Alternatively, the shuttle member 540 may consist only of the second magnetic element(s) 542. In the illustrated embodiment, the second magnetic elements 542 are provided in the form of rings wherein the guide tube 510 passes through openings at the center of each said ring. As with the first magnetic elements 532 discussed above, the second magnetic elements can be permanent magnets or metal elements having magnetic properties that are not necessarily permanent magnets. The magnets may be coated or plated using nickel, gold, epoxy, PTFE, parylene or other metals, alloys, polymer or combination thereof. The coating may serve as a barrier layer to prevent degradation of the magnet material, prevent leaching of metals from the magnet, provide a biocompatible and/or thromboresistant surface and/or provide a low friction surface for sliding on the guide tube.

The first and second magnetic elements 532, 542 of the magnetic guide 530 and shuttle member 540 are aligned magnetically with respect to each other to produce a magnetic force between the first and second magnetic elements 532, 542 that acts through the wall of the guide tube 510 to magnetically couple the shuttle member 540 to the magnetic guide 530. Consequently, sliding or translating the shuttle member 540 along the length of the guide tube 510 induces a corresponding translational movement of the magnetic guide 530 magnetically coupled thereto, and of the guide wire 402 that is fixedly coupled to the magnetic guide 530. Thus, the shuttle member 540 can be translated along the guide tube 510 to move the guide wire 402 of the clearance wire assembly 400 through the medical tube 100. Furthermore rotation of the shuttle member 540 tube may provide rotation of the clearance wire assembly 400.

Preferably, the first and second magnetic elements 532 and 542 have axially-aligned North-South polarity relative to the longitudinal axis of the guide tube 510, though the magnetic elements 532 and 542 can have radially-aligned North-South polarity in some examples. It has been found that magnets having axially-aligned polarity can provide suitable attractive force between the magnetic elements 532 and 542 to retain the magnetic guide 530 and shuttle member 540 in tandem while translating the shuttle member 540 along the tube 510 length, without unduly increasing friction as they translate along the tube 510.

In some examples, the drive system 500 also includes distal and proximal retaining members 526a, 526b fixedly coupled to the guide wire 402 on opposite sides of the magnetic guide 530. The retaining members 526a, 526b are preferably dimensioned so that they cannot pass through the distal and proximal ends 512, 514 of the guide tube 510, respectively, thereby retaining the magnetic guide 530 and the associated region of the guide wire 402 inside the guide tube 510. Thus, the distal and proximal retaining members 526a, 526b can provide limits to the distance translatable by the guide wire 402 through the medical tube 100. Moreover, in some examples, the drive system 500 can include one or more shuttle stops 550 coupled to the outer circumference 518 of the guide tube 510 that can prevent translation of the shuttle member 540 beyond the shuttle stops 550 and thereby inhibit further translation of the guide wire 402 through the medical tube 100.

Figure 16:
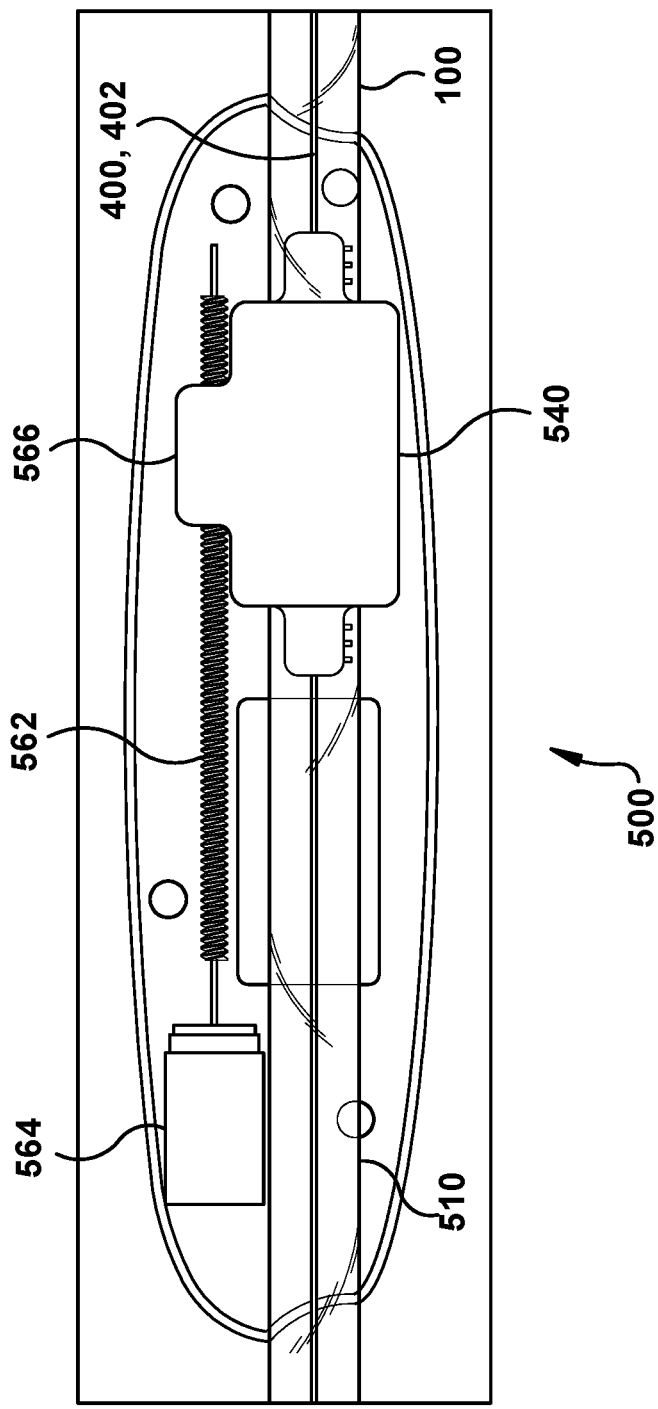
FIG. 16 shows a schematic cross section of the drive system shown in FIG. 14 with a lead screw driving mechanism.

The shuttle member 540 of the drive system 500 can be translated along the guide tube 510 either directly by hand or with a separate drive mechanism. For instance, as shown in FIG. 16 the drive system 500 can include a lead screw 562 and a motor 564 that is operable to rotate the lead screw 562. In this example, the shuttle member 540 can include a coupling portion 566 with a threaded bore extending at least partially therethrough that threadably receives lead screw 562. As the motor 564 is operated to rotate the lead screw 562, the shuttle member 540 will translate along the lead screw 562 and consequently translate along the guide tube 510 of the drive system 500, thereby moving the guide wire 402 of the clearance wire assembly 400. The direction of translation will depend upon the direction of rotation for the lead screw 562. Preferably, the motor 564 is operable to rotate the lead screw 562 in both clockwise and counter-clockwise directions such that the motor 564 is operable to move the guide wire 402 of the clearance wire assembly 400 both forwards and backwards. The lead screw could be a standard threaded rod and can have thread designs commonly used for lead screws such as an acme thread.

Figure 17:
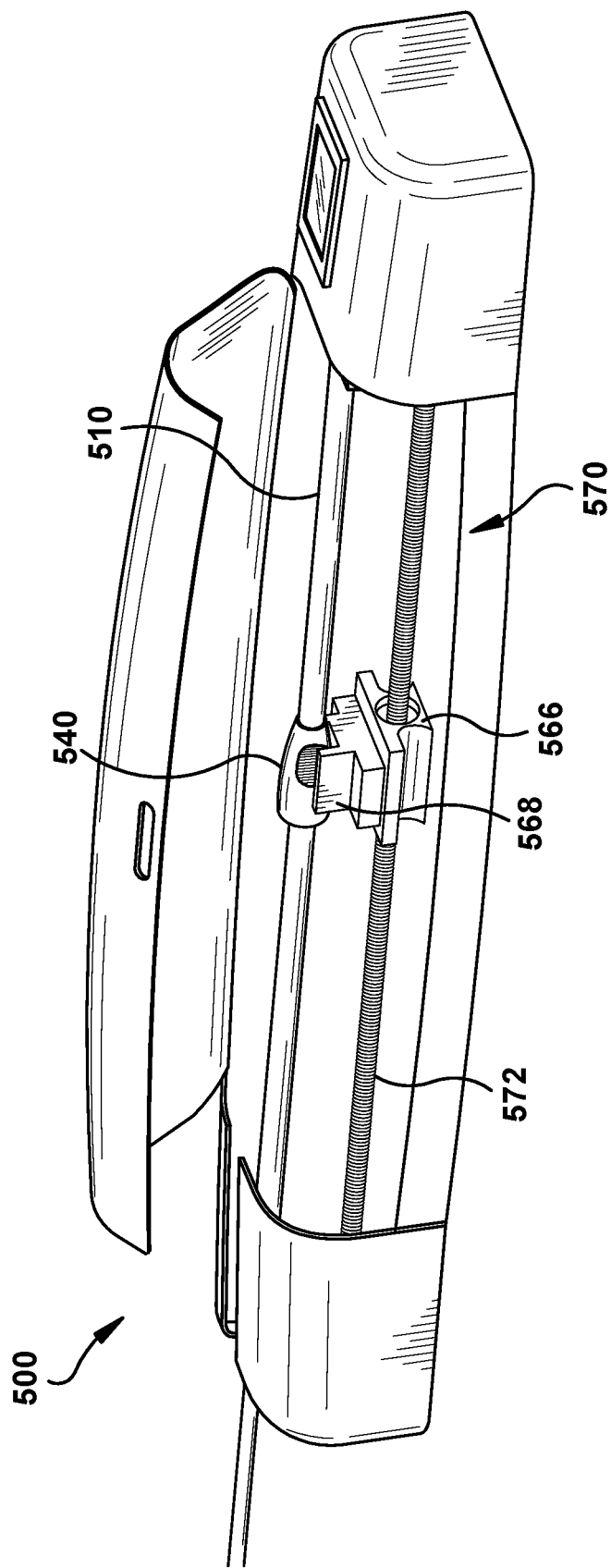
FIG. 17 shows an example linear actuator that can be used to drive the drive system shown in FIG. 14.

In some examples, one or more electromagnetic linear actuators can be coupled to the shuttle member 540 to translate the shuttle member 540 in a linear motion along the guide tube 510. Such actuators are generally known in the art, and may be coupled to the shuttle member 540 as illustrated in FIG. 17. In this example, the drive system 500 includes a carriage 566 having a nest 568 into which the shuttle member 540 is received. The nest 568 may receive the shuttle member 540 using a number of mechanical fits such as, for example, a releasable snap fit, a slip fit, an interference fit, or a compression fit. Alternatively, the carriage 566 may have one or more posts that each mate into a corresponding female fitting on the shuttle member 540, or vice versa. Other means for mechanically securing the shuttle member 540 to the carriage 566 may be used such as, for example, straps, zip ties, clamps, or an enclosure that at least partially encloses the shuttle member 540. Alternatively, the carriage 566 may have a magnetic element such as permanent magnet(s) or an electromagnet that directly couples to the magnetic guide 530, thereby eliminating the need for the shuttle member 540. The carriage 566 can be coupled to (e.g., be part of) a linear actuator and can be actuated by the linear actuator to result in translation of the clearance wire assembly 400 inside the guide tube 510 and therefore the clearance member(s) inside the medical tube 100. For example, the carriage 566 may be coupled to an actuator 570 having a lead screw 572 or a ball that is rotated by a motor to actuate the carriage 566. The motor could be a DC or AC motor. It could be a stepper motor or servo motor. The carriage 566 may also be coupled to a belt drive actuator wherein the carriage 566 is mounted on a belt that is under tension and driven by a motor. The carriage 566 may have bearing(s) that ride along a rail(s). Such a system could employ encoders and/or limit switches (such as proximity switch, reed and/or hall effect sensors) with the appropriate control systems to actuate the carriage 566 between two or more positions resulting in clearance member actuation within the medical tube 100.

Still in other examples, the carriage 566 can be coupled to one or more pneumatic actuators to actuate the carriage 566 and shuttle member 540 in a linear motion along the guide tube 510.

Still in other examples, the drive system 500 can include a worm drive mechanism wherein a spur gear is rotated by a motor. The spur gear can threadably engage a lead screw that is fixed relative to the shuttle member 540 such that rotation of the spur gear will cause the lead screw to translate across the spur gear and consequently cause the shuttle member 540 to translate in a linear motion along the guide tube 510.

The magnetic drive system 500 can comprise a variety of different drive mechanisms that can be operable to translate the shuttle member 540 along the guide tube 510 and consequently translate the guide wire 402 of the clearance wire assembly 400 through the medical tube 100. Moreover, any of the drive mechanisms discussed above can be operatively connected to a control system such as, for example, the control system 300 described above, to automatically control the drive mechanism. In particular, the controller 302 of the control system 300 can be operatively coupled to the actuator/motor of the drive mechanism and can be configured to selectively operate the actuator/motor according to a particular program and/or in response to the parameter(s) detected by the sensor(s) 306 of the control system 300.

Turning to FIG. 18, the fluid system 10 in some embodiments can include an induction motor drive system 600 that is operable to rotate the clearance wire assembly 400 within the medical tube 100. The induction motor drive system 600 includes a rotor 630 disposed within a tube portion 632 which, in the present example, corresponds to a portion of the medical tube 100. In other examples, the tube portion 632 may correspond to a guide tube or some other tube that is fluidly coupled to the proximal end 104 of the medical tube 100. The rotor 630 is fixedly coupled to the guide wire 402 of the clearance wire assembly 400 such that rotation of the rotor 630 will cause the portion(s) of the guide wire 402 fixedly coupled thereto to rotate with the rotor 630. In the illustrated example, the rotor 630 is fixedly coupled to a proximal end of the guide wire 402, though the rotor 630 can be fixedly coupled to more distal portions of guide wire 402 in other examples. The rotor 630 can either be a wound type or a squirrel-cage type rotor.

The induction motor drive system 600 further includes a shuttle member 640 disposed over the outer circumference of the tube portion 632 wherein the rotor 630 is located. The shuttle member 640 includes a stator 642 embedded or enclosed within a shuttle housing 644 that is preferably slightly spaced from the tube portion 632 such that an air gap will be present between the stator 642 and the rotor 630. In some examples, the shuttle member 640 may consist only of the stator 642.

The stator 642 of the shuttle member 640 is aligned with the rotor 630 within the tube portion 632 such that when AC current passes through windings of the stator 642, a rotating magnetic field will be generated that causes the rotor 630 within the tube portion 632 to rotate, which in turn will cause the portion(s) of the guide wire 402 fixedly coupled thereto to rotate. The speed of rotation can be adjusted by adjusting the frequency of the AC current supplied the stator 642.

The stator 642 of the induction motor drive system 600 can be operatively connected to a power source (e.g., controller) that is configured to selectively supply AC current to the stator 642. For instance, the stator 642 can be operatively connected to the controller 302 of the control system 300 described above, which can selectively supply AC current to the stator 642 to selectively operate the induction motor drive system 600 and rotate the clearance wire assembly 400 in any of the manners described above. In particular, the controller 302 can be configured to selectively operate the induction motor drive system 600 according to a particular program and/or in response to the parameter(s) detected by the sensor(s) 306 of the control system 300.

In some examples, the induction motor drive system 600 can be configured similar to the magnetic drive system 500 such that the shuttle member 640 of the induction motor drive system 600 can me translated along the tube portion 632 to translate the guide wire 402 within the medical tube 100. In such examples, the shuttle member 640 of the induction motor drive system 600 can likewise be driven manually or by any of the driving mechanisms described above in connection with the magnetic drive system 500.

Turning to FIGS. 19A-E, the fluid system 10 in some embodiments can include a spool drive system 700 that is operable to translate the clearance wire assembly 400 within the medical tube 100. The spool drive system 700 in some examples can correspond to the clearance device disclosed in U.S. Patent Application Publication No. 2015/0231313, the contents of which are attached as Exhibit C and incorporated by reference herein in their entirety. In one example, as shown in FIGS. 19A-D, the spool drive system 700 comprises a spool housing 702 having an inlet 704 that can be coupled to the proximal end 104 of the medical tube 100. The spool housing 702 comprises a first portion 706 and a second portion 708 that can be coupled together (e.g., via fasteners, welds, adhesive, etc.) to form an enclosure. Within the spool housing 702 resides a spool 710 that is rotatable about an axis. Moreover, the spool housing 702 defines a track 712 that is spaced from the spool 710 and extends at least partially about the perimeter of the spool 710, following a substantially similar line of curvature as the spool 710.

The guide wire 402 of the clearance wire assembly 400 can fed through the inlet 704 of the spool housing 702 and coupled (e.g. via set screw, adhesive, press fit, etc.) to the spool 710 such that rotation of the spool 710 about the spool's axis causes the guide wire 402 to wind or unwind about the spool 710 and move between an advanced state and a retracted state. In some embodiments, the distal end of the guide wire 402 may be positioned within the medical tube 100. If the spool 710 is rotated in one direction, the guide wire 402 will wind about the spool 710, causing the guide wire 402 (and any clearance member coupled thereto) to translate away from the distal end 102 of the medical tube 100 (i.e., retract). Conversely, if the spool 710 is rotated in the opposite direction, the guide wire 402 will unwind about the spool 710, causing the guide wire 402 (an any clearance member coupled thereto) to translate toward the distal end 102 of the medical tube 100 (i.e., advance). Thus, rotation of the spool 710 can control the translation (actuation) of the wire assembly 400 within the medical tube 100.

As the spool 710 is rotated, the track 712 of the spool housing 702 will help direct the guide wire 402 onto or off of the spool 710. Moreover, the track 712 can help maintain the guide wire 402 in a wound state and prevent the guide wire 402 from unwinding due to stiffness of the guide wire 402. However, friction from the track 712 can provide resistance to the guide wire 402 that in some examples, can substantially impede winding or unwinding of the guide wire 402 onto or off of the spool 710. Thus, the track 712 can comprise one or more aspects that can help reduce the friction applied by the track 712 to the guide wire 402.

For instance, in the illustrated example, the track 712 comprises a grooved surface 714 that extends at least partially about the perimeter of the spool 710 and includes grooves 716 that are circumferentially spaced about the spool 710. The grooves 716 of the track 712 will reduce the surface area of the track 712 that engages the guide wire 402 (as compared to a track 712 with a non-grooved surface), thereby reducing the amount of friction applied by the track 712 to the guide wire 402.

In another example, the surface 712 will include ridges (as opposed to grooves) that are circumferentially spaced about the spool 710. The ridges of the track 712 will contact the guide wire 712 (as opposed to the entire track surface), thereby reducing the surface area of the track 712 that engages the guide wire 402 and the amount of friction applied by the track 712 to the guide wire 402.

Figure 19A:
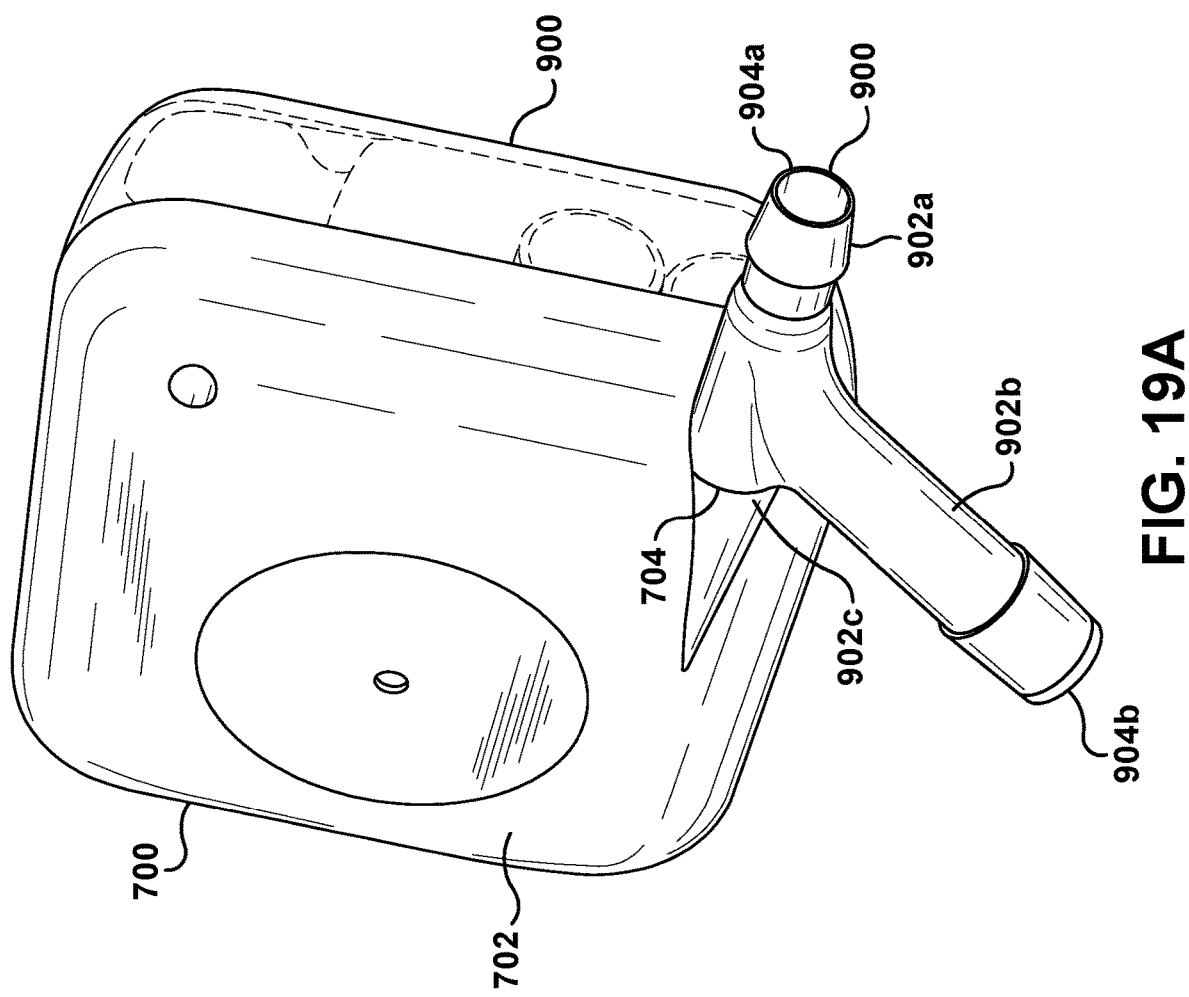
FIG. 19A shows a schematic perspective view of a third example drive system for a clearance-wire assembly of the fluid system.
Figure 19B:
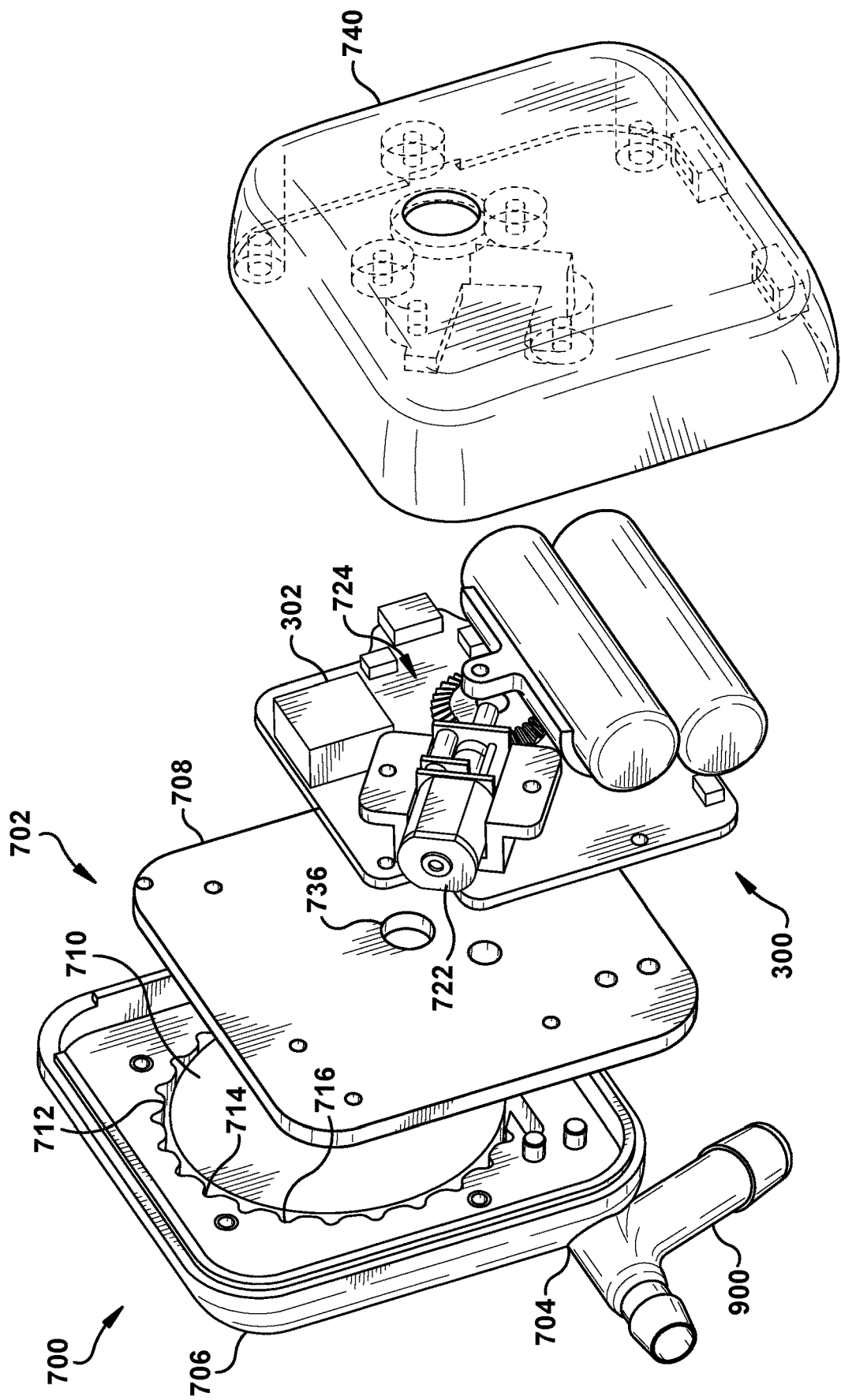
FIG. 19B shows an exploded view of the third example drive system.
Figure 19C:
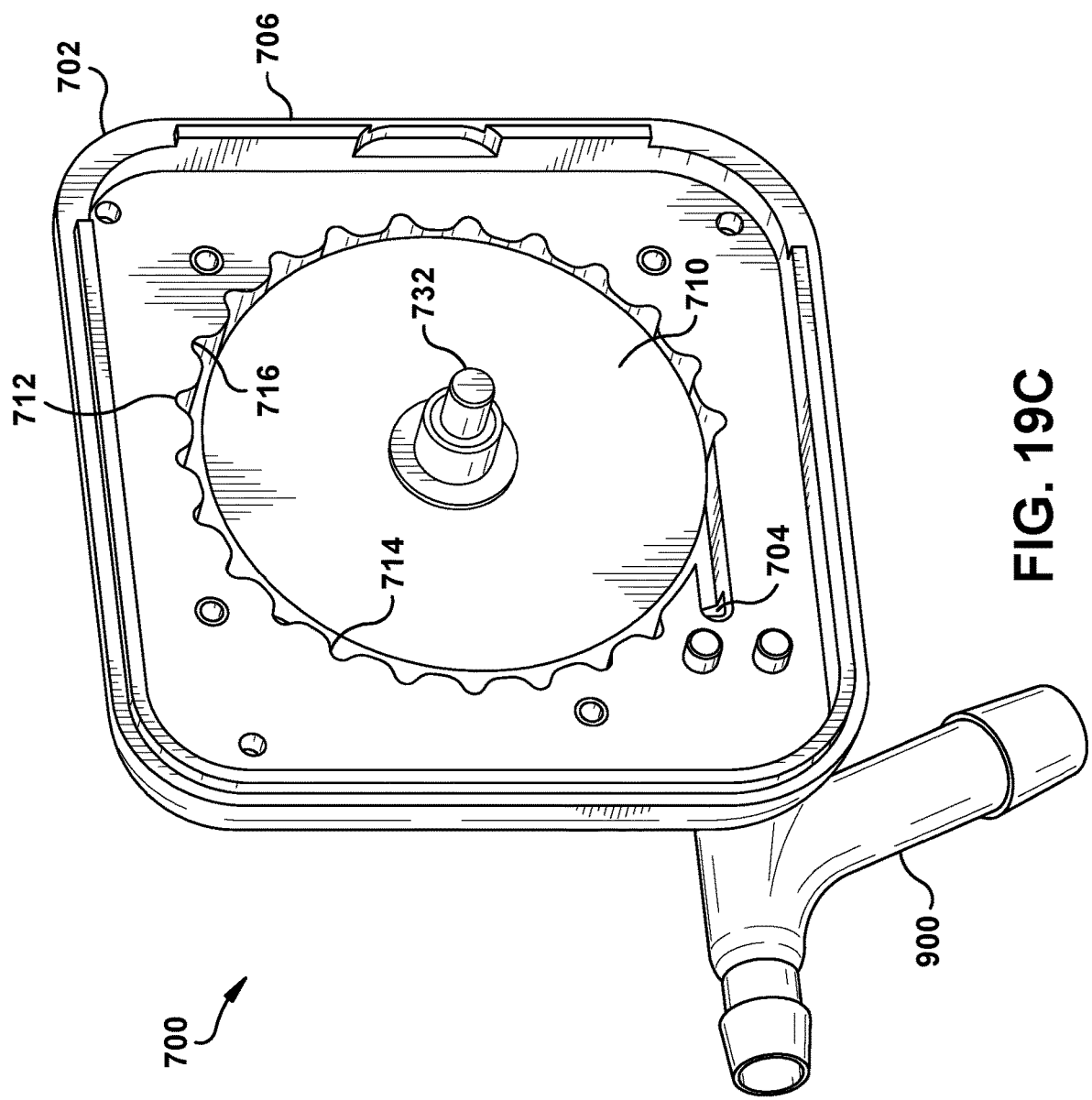
FIG. 19C shows a schematic perspective view of the third example drive system with a control system and motor housing removed.
Figure 19D:
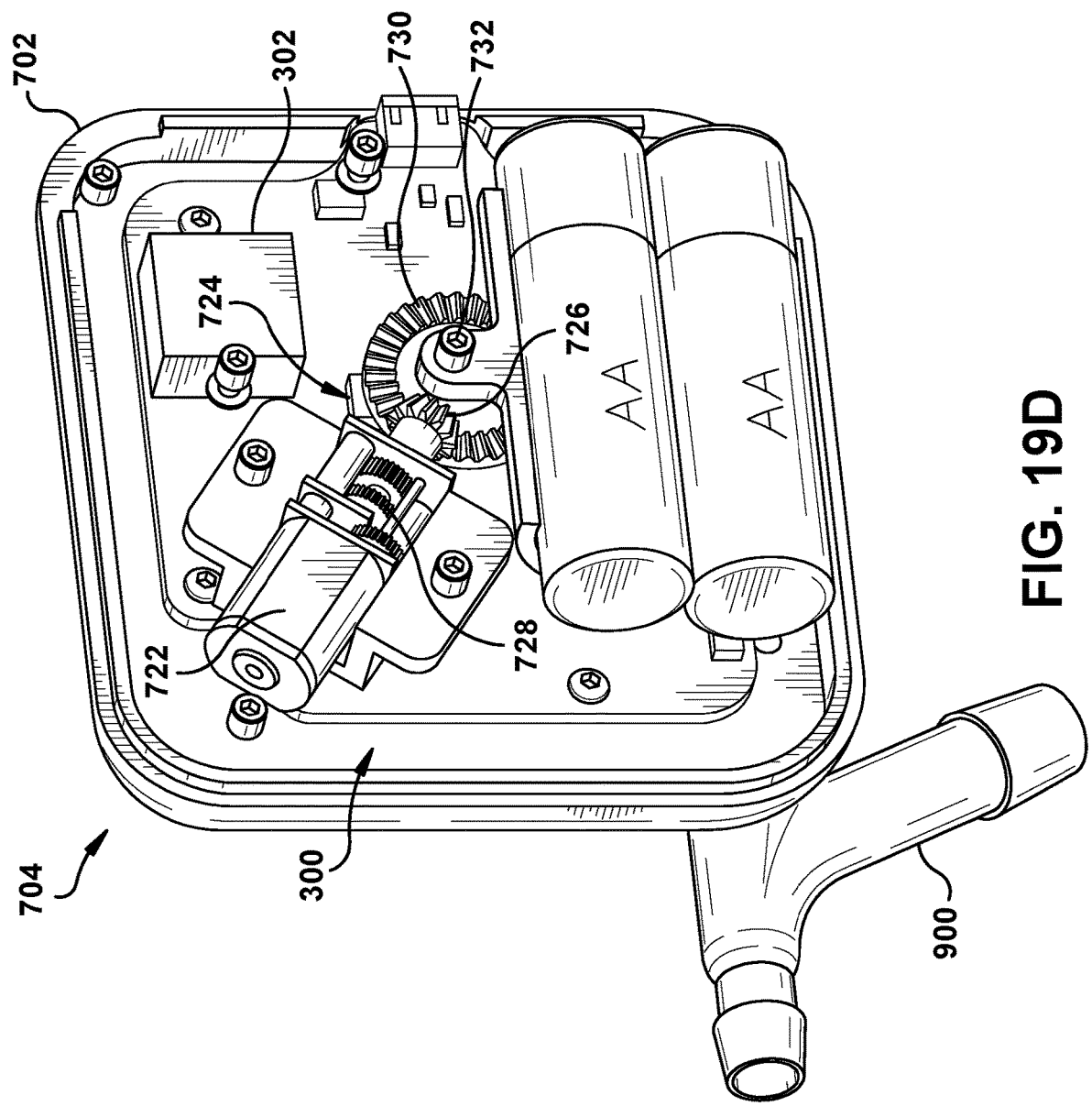
FIG. 19D shows a schematic perspective view of the third example drive system with the motor housing removed.
Figure 19E:
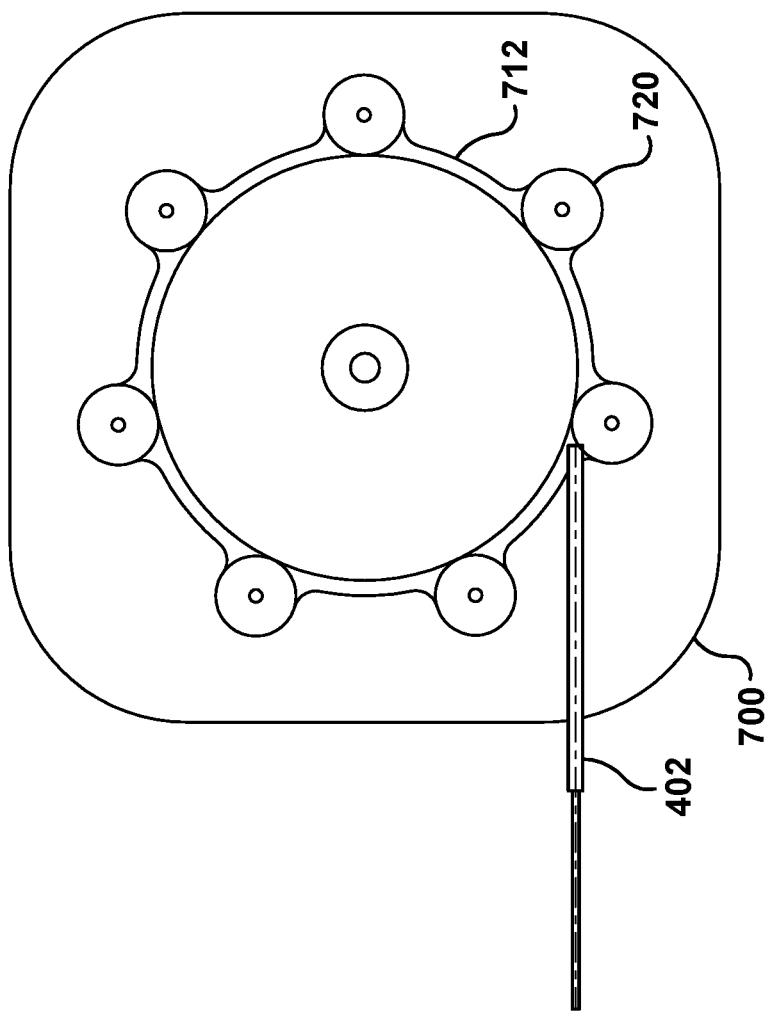
FIG. 19E shows a schematic, partial cross-section view of a variation of the third example drive system.

In some examples, the track 712 can comprise wheels 720 circumferentially spaced about the spool 710 that will rotatably engage the guide wire 402, as shown in FIG. 19E. Rotatable engagement of the wheels 720 can provide less resistance than other examples wherein the guide wire 402 engages a rigid surface. In such examples, the wheels 720 can be biased towards the spool 710 with springs or other biasing structure to help maintain engagement of the wheels 720 with the guide wire 402.

Also in some examples, the one or more components of the track 712 may comprise a low friction material or be coated with a low friction material such as, for example, hydrophilic coatings, hydrogels, parylene, PTFE, FEP, low friction polymer, or low friction silicone. For instance, the grooved surface 714 and/or the wheels 720 described above may comprise or be coated with such a low friction material. Or the track may have a liner composed of such material, for example, a thin ribbon of stainless steel sheet metal (or flat wire) may be coated with PTFE and installed (coupled) with the housing to form the track surface that interfaces with the wire. The ribbon may be held in place by various means such as adhesive, clips or it may be made from spring temper steel and held in place by spring tension against the housing. It may be held in place by other means as well In one configuration the track 712 is composed of ball bearings contained within an inner and outer race. In this embodiment the wire engages with the ball bearings allowing for low friction movement of the wire.

In some examples, the spool drive system 700 can include a motor 722 that is operable to rotate the spool 710 within the spool housing 702 and cause translation of the wire assembly 440 within the medical tube 100. As shown in FIG. 19D, the motor 722 can be arranged outside of the spool housing 702 and can be rotatably coupled to the spool 710 within the spool housing 702 via a transmission mechanism 724. In the illustrated embodiment, the transmission mechanism 724 comprises a first bevel gear 726 fixed to a shaft 728 of the motor 722 and a second bevel gear 730 fixed to a shaft 732 of the spool 710 that threadably engages the first bevel gear 726. However, the transmission mechanism 724 may comprise other types and/or combinations of gears and shafts in other examples to rotatably couple the motor 722 to the spool 710. Indeed, in some examples, the transmission mechanism 724 may simply consist of a shaft that is common to both the motor 722 and spool 710.

A portion of the transmission mechanism 724 (e.g., the shaft 732 of the spool 710) will penetrate through an aperture 736 (shown in FIG. 19B) in the spool housing 702. In some examples, a seal can be provided that can permit the transmission mechanism 724 to penetrate through the aperture 736 while inhibiting fluids and other materials from transferring through the aperture 736. Thus, a sterile field within the spool housing 702 can be preserved with respect to the environment outside of the spool housing 702. In addition or alternatively, the spool drive system 700 can comprise a motor housing 740 (shown in FIGS. 19A-B) that can be coupled to the spool housing 702 (e.g., via fasteners)

to enclose the motor 722 and transmission mechanism 724. The motor housing 740 can be sealed against the spool housing 702 to provide a sterile environment around the motor 722 and transmission mechanism 724 that is sealed from an environment exterior to the motor housing 740.

In some examples, the motor 722 can be battery powered. Furthermore, the motor 722 can be operatively connected to the controller 302 of the control system 300 described above, which can selectively operate the motor 722 to translate the clearance wire assembly 400 in any of the manners described above. In particular, the controller 302 can be configured to selectively operate the motor 722 according to a particular program and/or in response to the parameter(s) detected by the sensor(s) 306 of the control system 300. Moreover, the control system 300 and controller 302 may reside at least partially within the motor housing 740, as shown in FIG. 19B.

The spool housing 702 will likely be separated from the blood path by a seal that allows a vacuum to be maintained in the fluid path. The spool housing 702 may need to be sterile, having a seal that maintains sterility form the motor housing. The seal may also maintain a pressure as a safety (backup) against losing pressure. The seals can take various forms such as rubber seals or welds. Where a rotating shaft or translating wire traverses a seal, it will need to be an appropriate type of seal. In an alternate embodiment the motor housing 740 may be removably coupled to the spool housing 702, so that it can be reused and the spool housing 702 disposed of.

Figure 20:
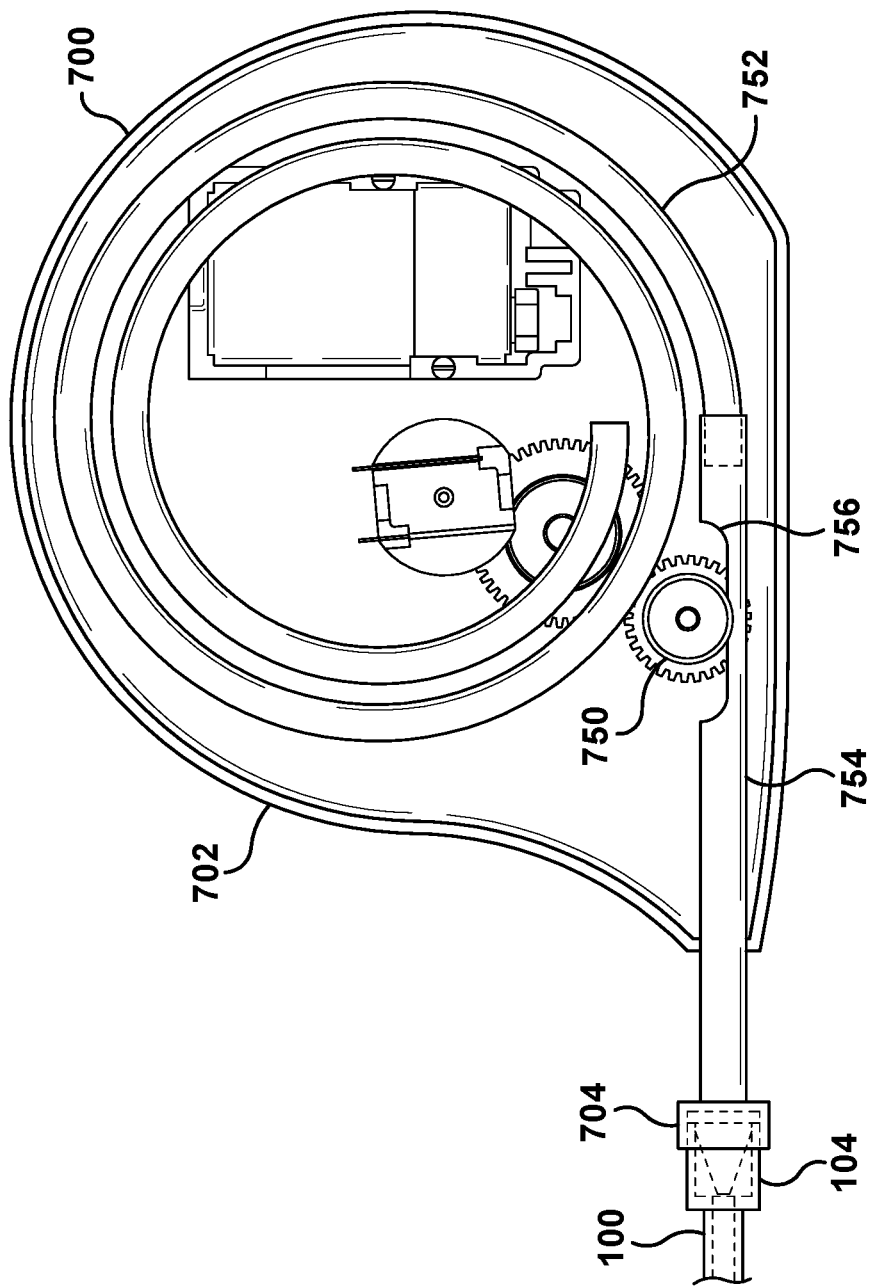
FIG. 20 shows a schematic, partial cross-section view of another variation of the third example drive system.

Turning to FIG. 20, in a variation of the spool drive assembly 700 described above, the spool 710 is replaced with a roller 750 and the track 712 is replaced with coiled tube 752. In this example, the spool drive assembly 700 has an inlet tube 754 with a cutout region 756 and the roller 750 is disposed within the cutout region 756 and is rotatable relative to the spool housing 702. The guide wire 402 of the clearance wire assembly 400 can be fed through the inlet 704 of the spool housing 702 such that a portion of the guide wire 402 will reside between (and preferably engage) the outer circumference of the roller 750 and an inner surface of the inlet tube 754. The roller 750 can then be rotated in one direction (e.g., counter-clockwise) to pull the guide wire 402 proximally (i.e., away from the patient) through the space between the roller 750 and the inner surface of the inlet tube 754, thereby causing the guide wire 402 to retract through the medical tube 100. Alternatively, the roller 750 can be rotated in an opposite direction (e.g., clockwise) to push the guide wire 402 distally (i.e., toward the patient) through the space between the roller 750 and the inner surface of the inlet tube 754, thereby causing the guide wire 402 to advance through the medical tube 100. The roller 750 can be rotated similar to the spool 710 using the motor 722 and control system 300 described above.

The coiled tube 752 will receive the guide wire 402 as it is pulled proximally by the roller 750 into the spool housing 702. The coiled tube 752 may be manufactured from a low friction material. Various polymers may be used such as PTFE, FEP, or other low friction polymer. However, it is to be appreciated that the tube 752 can have other configurations in other examples such as, for example, a straight configuration. Moreover, in some embodiments the coiled tube 752 may be integral with the spool housing 702.

Figure 21:
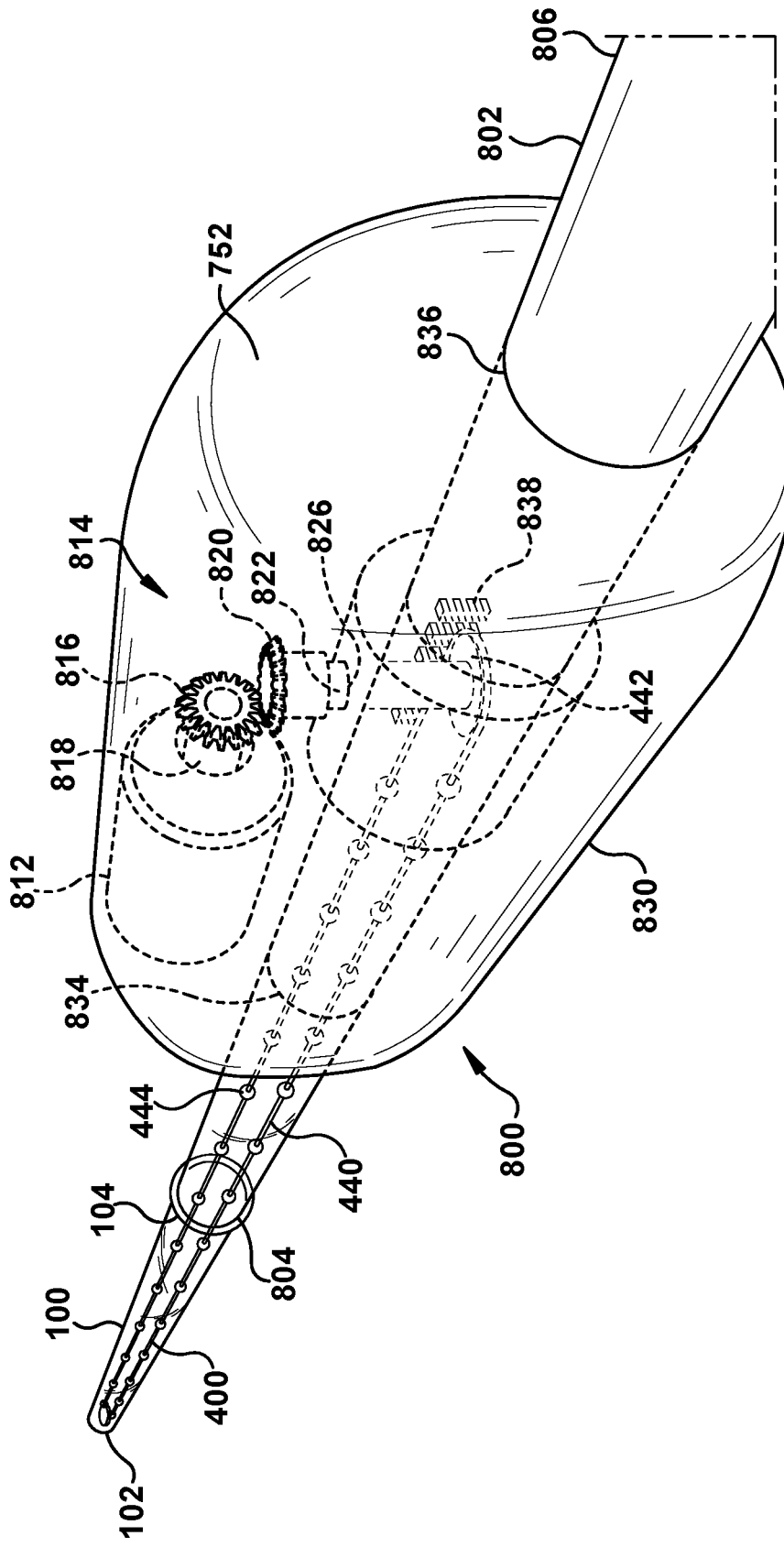
FIG. 21 is a schematic perspective view of a fourth example drive system for a clearance-wire assembly of the fluid system.

Turning to FIG. 21, the fluid system 10 in some embodiments can include a conveyor drive system 800 that is operable to convey, for example, the conveyor-type wire assembly 400 discussed above in connection with FIGS. 12A-C. The conveyor drive system 800 includes a conveyor tube 802 having a distal end 804 that is coupled to the proximal end 104 of the medical tube 100 and a proximal end 806 that is fluidly coupled to a suction source such as, for example, the receptacle 202 of the drain assembly 200 shown in FIG. 2. A pulley 442 at a proximal end of the wire assembly 400 resides within the conveyor tube 802 and is arranged such that a rotational axis of the pulley 442 intersects with and is perpendicular to the central axis of the conveyor tube 802.

The conveyor drive system 800 includes a motor 812 arranged outside of the conveyor tube 802 that is rotatably coupled to the pulley 442 within the conveyor tube 802 via a transmission mechanism 814. In the illustrated embodiment, the transmission mechanism 814 comprises a first bevel gear 816 fixed to a shaft 818 of the motor 812 and a second bevel gear 820 fixed to a shaft 822 of the pulley 442 that threadably engages the first bevel gear 816. However, the transmission mechanism 814 may comprise other types and/or combinations of gears and shafts in other examples to rotatably couple the motor 812 to the pulley 442. Indeed, in some examples, the transmission mechanism 814 may simply consist of a shaft that is common to both the motor 812 and pulley 442.

A portion of the transmission mechanism 814 (e.g., the shaft 822 of the pulley 442) will penetrate through an aperture 826 in the conveyor tube 802. In some examples, a seal can be provided that can permit the transmission mechanism 814 to penetrate through the aperture 826 while inhibiting fluids and other materials from transferring through the aperture 826. Thus, a sterile field within the conveyor tube 802 can be preserved with respect to the environment outside of the conveyor tube 802. In addition or alternatively, the drive system 800 can comprise a housing 830 that will enclose the motor 812 and transmission mechanism 814. The housing 830 can have a sealed inlet 834 and sealed outlet 836 that the conveyor tube 802 can extend through such that the portion of the conveyor tube 802 penetrated by the transmission mechanism 814 is also enclosed within the housing 830. Thus, the housing 830 can provide a sterile environment around the motor 812, transmission mechanism 814, and conveyor tube 802 that is sealed from an environment exterior to the housing 830.

The motor 812 of the drive system 800 can be operated to rotate the pulley 442 within the conveyor tube 802, which in turn will result in conveyance of the wire assembly 440 about the pulley 442. In some examples, the pulley 422 can comprise teeth about its perimeter that will engage the belt 440 and/or clearance members 444 of the wire assembly 400 as the pulley 422 is rotated to facilitate conveyance of the wire assembly 400. In other examples, the pulley 422 may simply comprise a smooth circumferential surface and the wire assembly 400 will be tensioned about the circumferential surface such that rotation of the pulley 422 will convey the wire assembly 400 via friction between the wire assembly 400 and the circumferential surface.

The motor 812 can be operated such that the belt 440 of the wire assembly 400 conveys continuously or intermittently about the pulleys 442. Moreover, the motor 812 can be operated such that the belt 440 conveys at all times in the same direction (e.g., clockwise) or in alternating directions (e.g., clockwise and then counter-clockwise). In some examples, the motor 812 can be operatively connected to the controller 302 of the control system 300 described above, which can selectively operate the motor 812 to convey the clearance wire assembly 400 in any of the manners described above. In particular, the controller 302 can be configured to selectively operate the motor 812 according to a particular program and/or in response to the parameter(s) detected by the sensor(s) 306 of the control system 300.

Figure 22A:
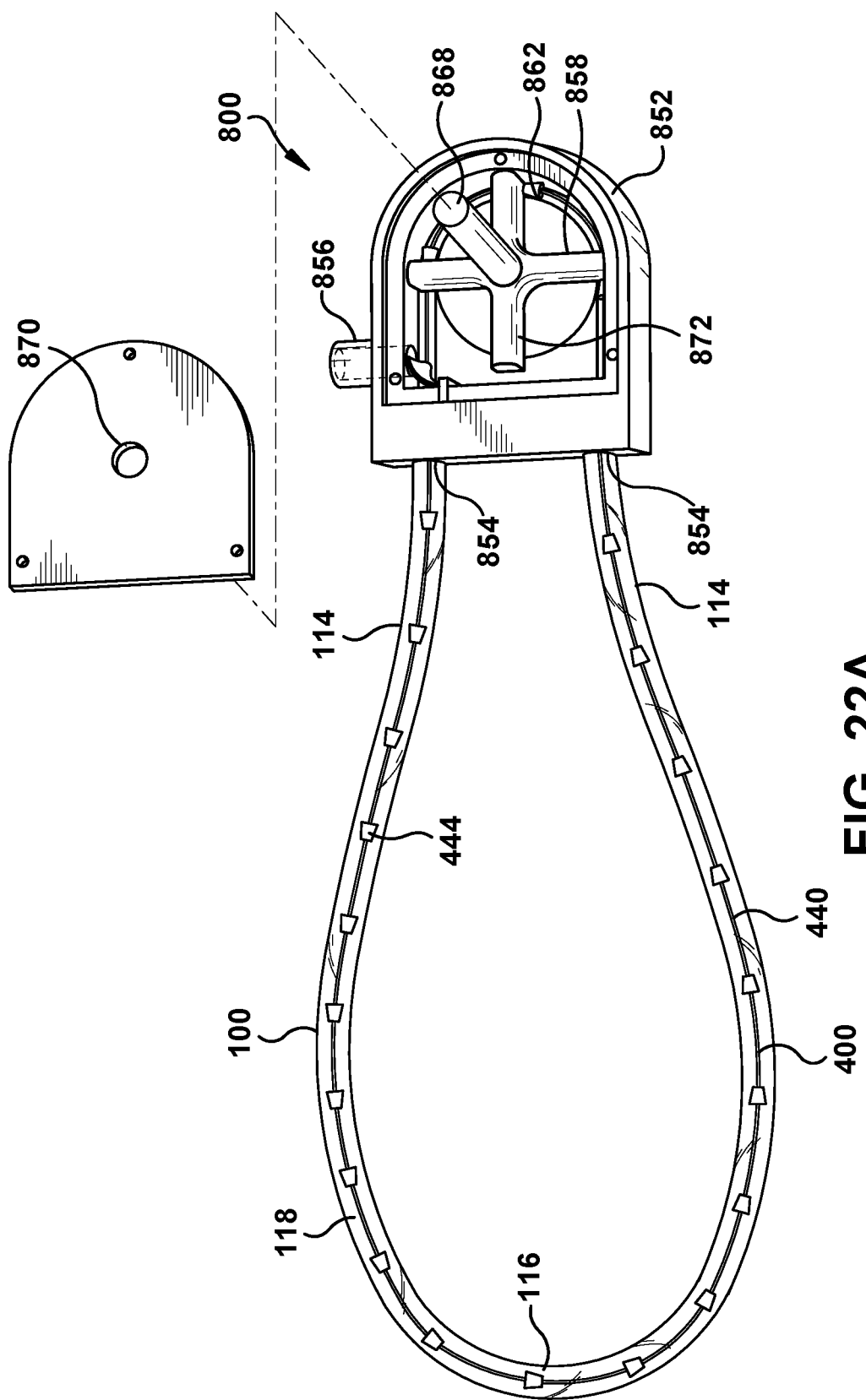
FIG. 22A is an exploded view of a fifth example drive system for a clearance-wire assembly of the fluid system.
Figure 22B:
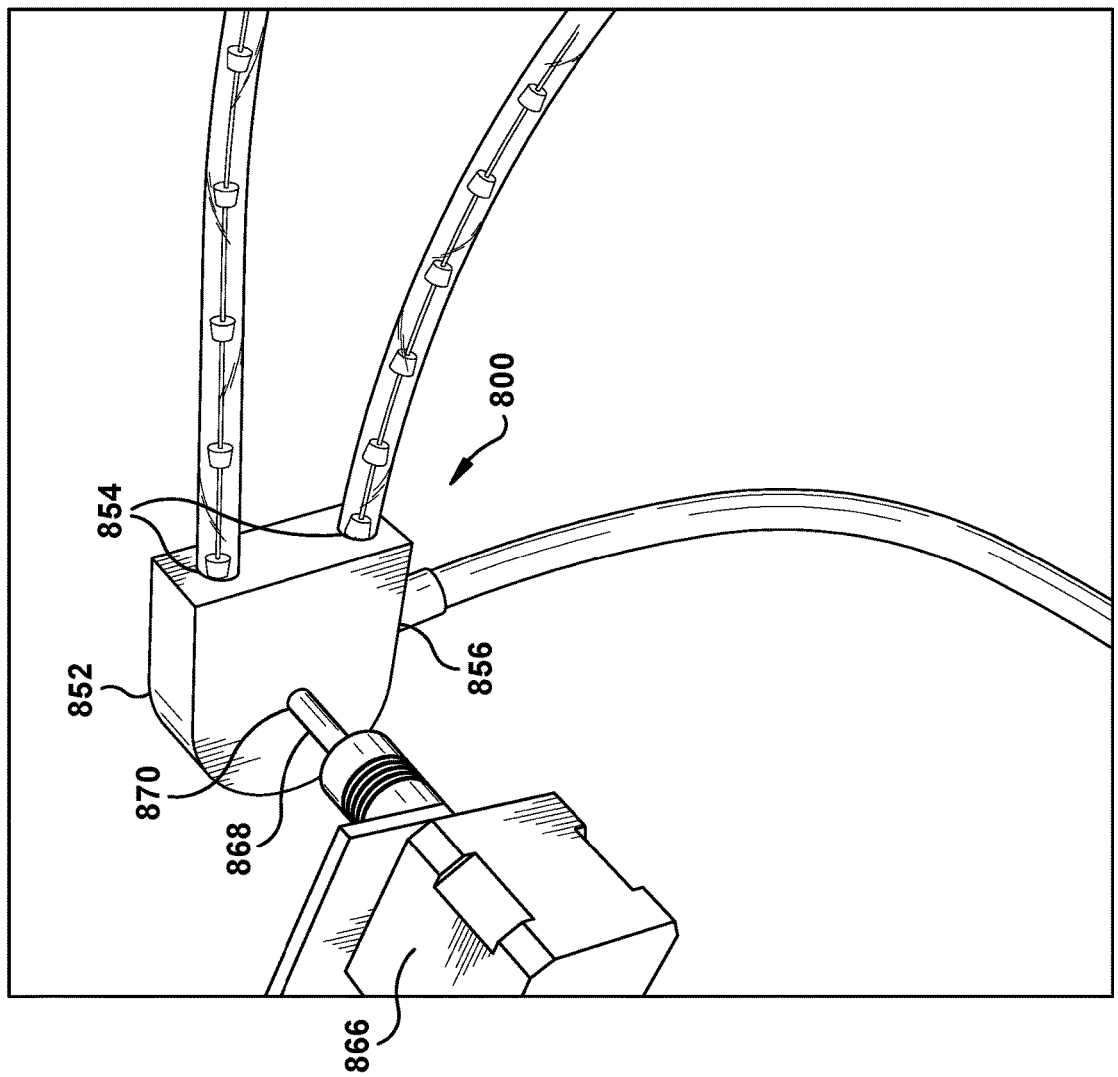
FIG. 22B is a perspective view of the fifth example drive system.

In some examples, the conveyor drive system 800 will include one or more brushes 838 located within the conveyor tube 802 that will engage the clearance members 444 and/or the belt 440 of the clearance wire assembly 400 as the belt 440 is conveyed about the pulley 442. This can help clean the clearance wire assembly 400 and dislodge any material that may be collected on the clearance wire assembly 400. The brushes 838 may be heparin coated Another example conveyor drive system 800 is illustrated in FIGS. 22A & 22B, which is operable to convey, for example, the conveyor-type wire assembly 400 discussed above in connection with FIG. 13. The conveyor drive system 800 includes a housing 852 having two ports 854 that are each fluidly coupled to one of the two proximal portions 114 of the medical tube 100. The housing 852 can further include a third port 856 that is fluidly coupled to a suction source such as, for example, the receptacle 202 of the drain assembly 200 shown in FIG. 2. Arranged within the housing 852, the drive system 800 can further include a sprocket 858 that is rotatable. Moreover, the housing 852 can define a track 862 that extends partially (e.g., halfway) about the perimeter of sprocket 858 and is coaxial with the sprocket 858.

The housing 852 and the medical tube 100 together will form the continuous loop 118 that the belt 440 of the wire assembly 400 is conveyed about. More specifically, the belt 440 will extend through the medical tube 100, into the housing 852 through both ports 854, and wrap around the sprocket 858 along the track 862.

The conveyor drive system 800 includes a motor 866 (shown in FIG. 22B) arranged outside of the housing 852 that is rotatably coupled to the sprocket 858 within the housing 852 via a transmission mechanism 868. In the illustrated embodiment, the transmission mechanism 868 comprises a shaft that is common to both the motor 866 and the sprocket 858. However, the transmission mechanism 868 may comprise additional gears and/or shafts in other examples to rotatably couple the motor 866 to the sprocket 858.

A portion of the transmission mechanism 868 will penetrate through an aperture 870 in the housing 852. Preferably, a seal can be provided that can permit the transmission mechanism 868 to penetrate through the aperture 870 while inhibiting fluids and other materials from transferring through the aperture 870. Thus, a sterile field within the housing 852 can be preserved with respect to the environment outside of the housing 852.

The motor 866 of the drive system 800 can be operated to rotate the sprocket 858 within the housing 852, which in turn will result in conveyance of the wire assembly 400 about the sprocket 858. In the present example, the sprocket 858 comprises spindles 872 that will engage the clearance members 444 of the wire assembly 400 as the sprocket 858 is rotated to facilitate conveyance of the wire assembly 400. In other examples, the sprocket 858 can comprise teeth about its perimeter that will engage the belt 440 and/or clearance members 444 of the wire assembly 400 as the sprocket 858 is rotated to facilitate conveyance of the wire assembly 400. Still in other examples, the sprocket 858 may simply comprise a smooth circumferential surface and the wire assembly 400 will be tensioned about the circumferential surface such that rotation of the sprocket 858 will convey the wire assembly 400 via friction between the wire assembly 400 and the circumferential surface.

The motor 866 can be operated such that the wire assembly 400 conveys continuously or intermittently about the sprocket 858. Moreover, the motor 866 can be operated such that the belt 440 conveys at all times in the same direction (e.g., clockwise) or in alternating directions (e.g., clockwise and then counter-clockwise). In some examples, the motor 866 can be operatively connected to the controller 302 of the control system 300 described above, which can selectively operate the motor 866 to convey the clearance wire assembly 400 in any of the manners described above. In particular, the controller 302 can be configured to selectively operate the motor 866 according to a particular program and/or in response to the parameter(s) detected by the sensor(s) 306 of the control system 300.

Figure 23:
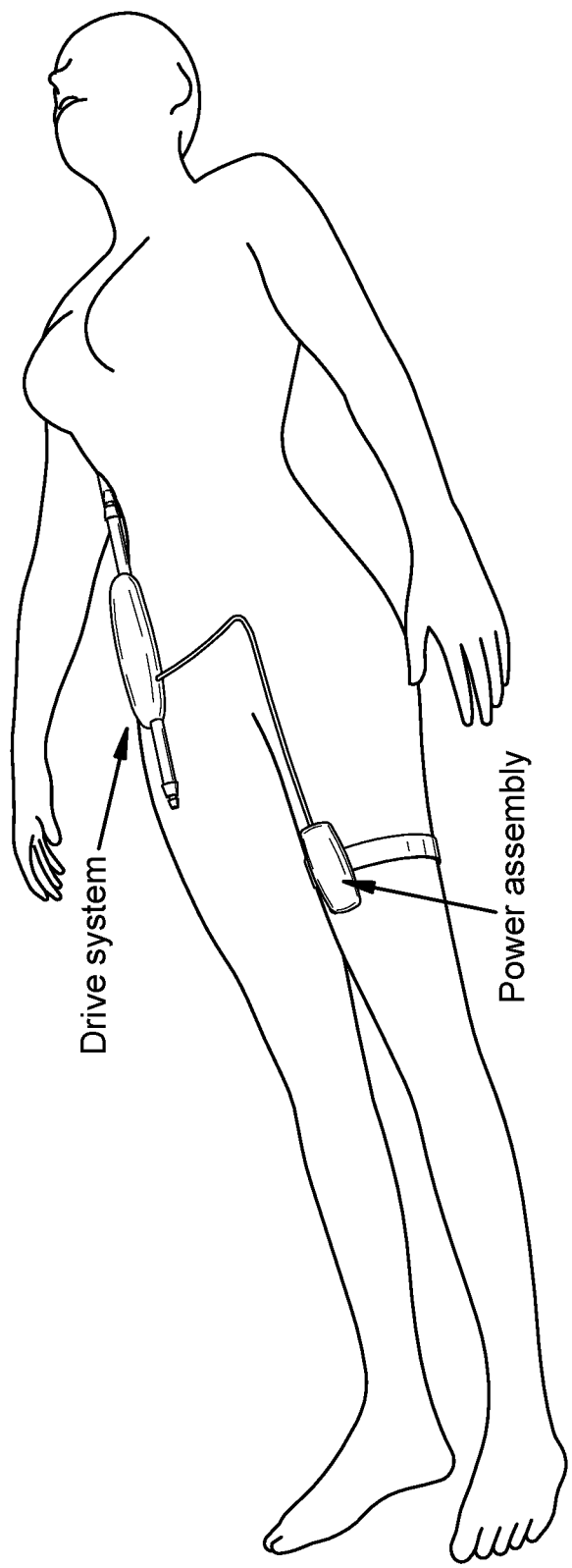
FIG. 23 is a schematic perspective view of a drive system with a power assembly separated from a main body of the drive system.

The various drive systems 500, 600, 700, 800 discussed above can each be utilized to move the clearance wire assembly 400 within the medical tube 100 according to one or more of the manners described above. In particular, the drive systems 500, 600, 700, 800 can each be utilized to translate, rotate, and/or convey the clearance wire assembly 400 within the medical tube 100. Moreover, the drive systems 500, 600, 700, 800 can be operatively coupled to a controller such as, for example, the controller 302 of the control system 300 described above, in order to automatically control movement of the clearance wire assembly 400 within the medical tube 100. Preferably, the drive systems 500, 600, 700, 800 can be configured (e.g., sized and shaped) to be hand held and in some examples, disposable. If a drive system is motorized, the motor can be powered with rechargeable batteries. Moreover, in some examples, the motor can be powered by a power assembly that is separate from a main body of the drive system and connected to the main body via wiring, as shown in FIG. 23. By separating the power assembly, the power assembly can be replaced/recharged without having to disassemble the main body of the drive system.

Figure 24:
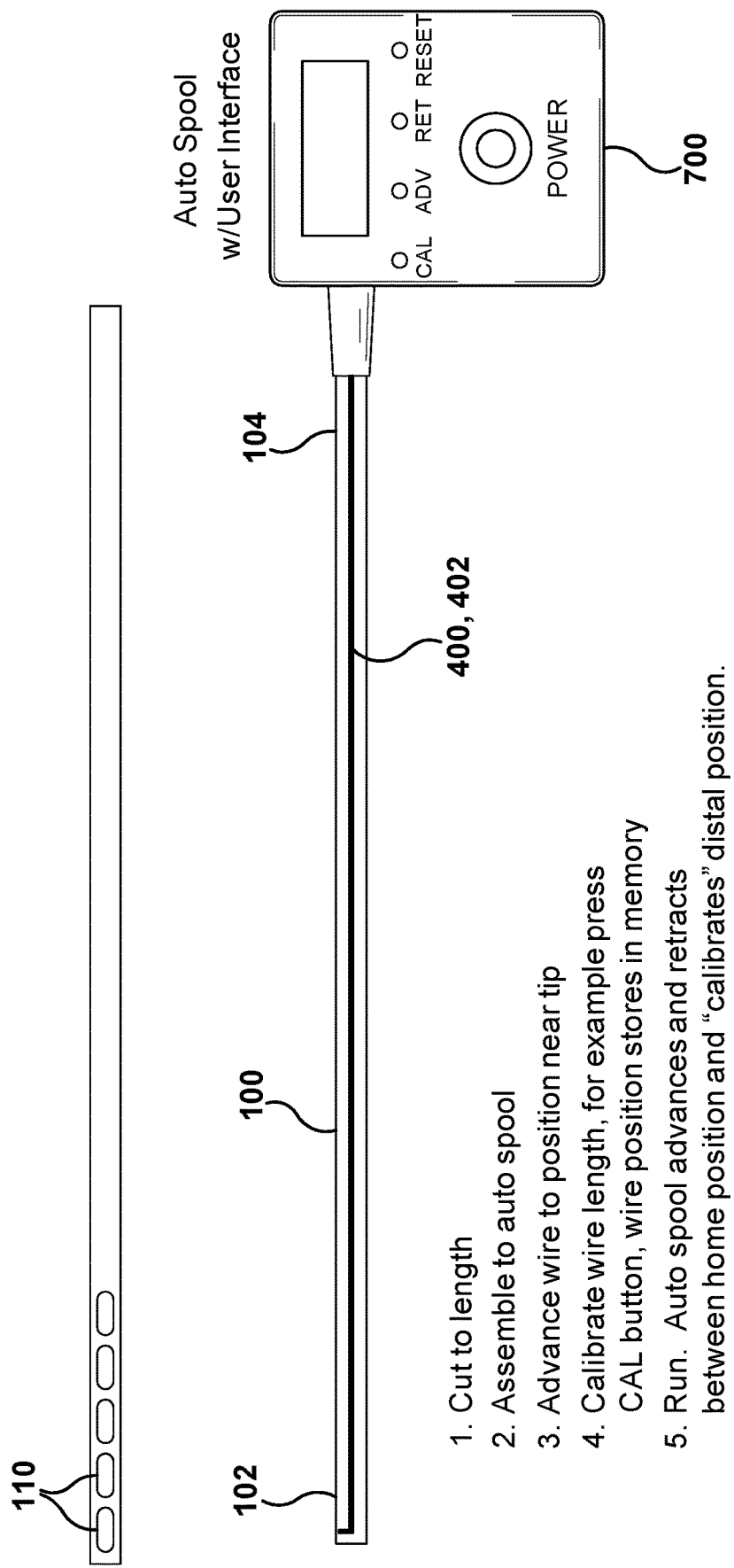
FIG. 24 shows a schematic side view of a fluid system with a drive system that is configured to permit calibration of the drive system.

For embodiments wherein the fluid system 10 has a drive system (e.g., one of drive systems 500, 600, 700, 800) configured to translate or convey the clearance wire assembly 400 along the passageway 106 of the medical tube 100, the drive system can be configured to permit calibration of the distance translated/conveyed by the clearance wire assembly 400. For instance, FIG. 24 shows an example spool drive system 700 configured to translate the clearance wire assembly 400 along the passageway 106 of the medical tube 100. The spool drive system 700 can be operated to advance the clearance wire assembly 400 toward the distal end 102 of the medical tube 100 until the clearance wire assembly 400 reaches a position desired to be a fully-advanced position. For example, the spool drive system 700 can be operated to advance the clearance wire assembly 400 toward the distal end 102 of the medical tube 100 until the distal end of the clearance wire assembly 400 reaches the distal end 102 of the medical tube 100. The position of the clearance wire assembly 400 can be detected using various means such as by counting steps of a stepper motor, hall sensors, optical encoder, etc. A button, switch, touchscreen, or some other structure can then be engaged (e.g., pressed) by a user to send a signal to a controller (e.g., controller 302) indicating that clearance wire assembly 400 is in the fully-advanced position. The controller can then store this position in memory to calibrate the fully-advanced position for the drive system 700.

Similarly, the spool drive system 700 can be operated to retract the clearance wire assembly 400 toward the proximal end 104 of the medical tube 100 until the clearance wire assembly 400 reaches a position desired to be a fully-retracted position. For example, the spool drive system 700 can be operated to retract the clearance wire assembly 400 toward the proximal end 104 of the medical tube 100 until the distal end of the clearance wire assembly 400 is proximal to a set of apertures 110 in a distal portion the medical tube 100. The position of the clearance wire assembly 400 can be detected using various means such as by counting steps of a stepper motor, hall sensors, optical encoder, etc. A button, switch, touchscreen, or some other structure can then be engaged (e.g., pressed) by a user to send a signal to a controller (e.g., controller 302) indicating that clearance wire assembly 400 is in the fully-retracted position. The controller can then store this position in memory to calibrate the fully-retracted position for the drive system 700.

Once the fully-advanced position and fully-retracted position have been calibrated, the controller can operate the drive system 700 such that the clearance wire assembly 400 translates within the medical tube 100 between the fully-advanced position and fully-retracted position.

It is to be appreciated that any of the drive systems 500, 600, 800 discussed above can also be similarly calibrated as the drive system 700 shown in FIG. 24. Furthermore, in some examples, the drive systems 500, 600, 700, 800 can be configured to automatically calibrate without the need for a user to indicate when the clearance wire assembly 400 has reached the fully-advanced position and/or fully-retracted position. For instance, in some examples each drive system 500, 600, 700, 800 can include one or more sensors (e.g., sensor(s) 306) that can detect when its associated clearance wire assembly 400 has reached the fully-advanced position and/or fully-retracted position and send a signal to its associated controller indicating the wire assembly's position such that the controller can store the position in memory and calibrate the drive system.

Figure 25:
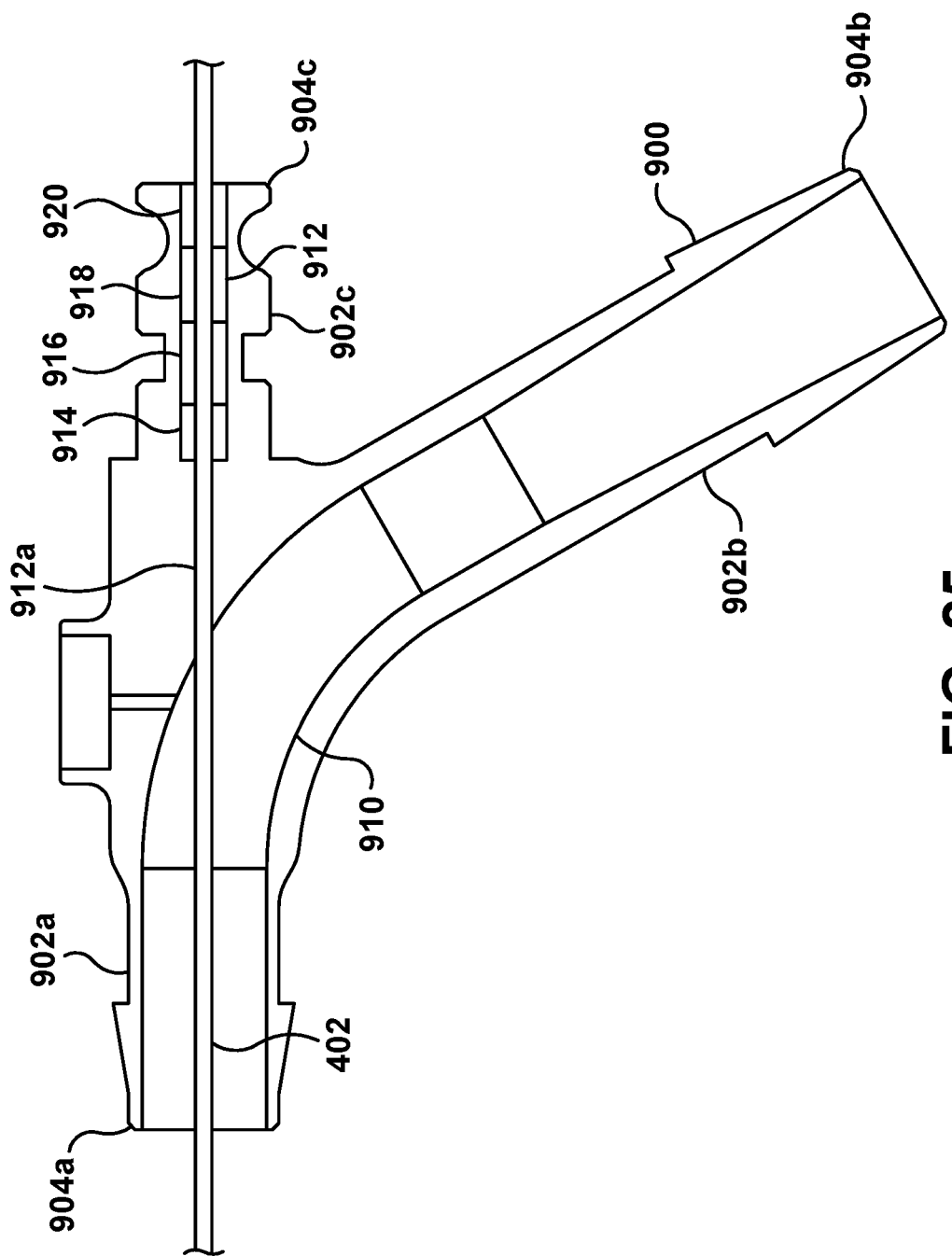
FIG. 25 is a cross-section view of an example Y-coupling that can be used to couple the medical tube of the fluid system with another structure.

Turning now to FIG. 25, a Y-coupling 900 will be described that can be used to couple the medical tube 100 to various structures such as, for example, the drive systems 500, 600, 700, 800 discussed above. The Y-coupling 900 includes a first tube portion 902a having an end 904a that can be fluidly coupled to the proximal end 104 of the medical tube 100. The Y-coupling 900 further includes a second tube portion 902b having an end 904b that can be fluidly coupled to a suction source such as, for example, the receptacle 202 of the drain assembly 200 shown in FIG. 2. Moreover, the Y-coupling 900 further includes a third tube portion 902c having an end 904c that can be coupled to another structure such as, for example, an inlet or port of one of the drive systems 500, 600, 700, 800 discussed above. For instance, FIG. 19A shows the Y-coupling 900 wherein the end 904c is coupled to the spool drive system 700 discussed above.

The Y-coupling 900 defines a passageway 910 that provides fluid communication between the end 904a of the first tube portion 902a and the end 904b and of the second tube portion 902. Thus, the passageway 910 can provide a path for material to be sucked out of the medical tube 100 and discharged to the suction source.

The Y-coupling 900 further includes an aperture 912 that extends through the third tube portion 902c and opens into the passageway 910. The aperture 912 is sized to permit the guide wire 402 of the clearance wire assembly 400 to pass through the aperture 912. Thus, when the medical tube 100 is connected to the Y-coupling 900, the guide wire 402 can extend from within the medical tube 100, through the Y-coupling 900, and into whatever structure is coupled to the end 904c of the Y-coupling 900.

In some examples, at least a portion of the aperture 912 (e.g., portion 912a) has a diameter that is just slightly larger than the diameter of the guide wire 402. This will permit the guide wire 402 to pass through the aperture 912 but inhibit fluids (e.g., bodily fluids) and other materials from passing through the aperture 912. By inhibiting fluids and other materials from passing through the aperture 912, a vacuum within the passageway 910 (and the medical tube 100 in fluid communication with the passageway 910) can be preserved and isolated from whatever pressurized environment may be in communication with the end 904c of the third tube portion 902c. Moreover, fluids (e.g., bodily fluids) and other materials passing through the passageway 910 can be inhibited from passing through the aperture 912 into whatever structure is coupled to the end 904c of the third tube portion 902c.

In addition or alternatively, in some examples one or more cylindrical bushings 914 can be provided within the aperture 912 that the guide wire 402 can pass through. Each bushing 914 can comprise, for example, Delrin, ceramic, stainless steel, PEEK, PTFE, closed cell urethane foam, packed fibers, and/or other materials.

In addition or alternatively, in some examples one or more cylindrical wipers can be provided within the aperture 912 to inhibit fluids (e.g., bodily fluids) and other materials from passing through the aperture 912. For example, a cylindrical wiper 916 may be provided within the aperture 912 that the guide wire 402 can pass through. The wiper 916 preferably comprises a porous material that can absorb any fluid that may attempt to pass through the wiper 916 with the guide wire 402. For example, the wiper 916 may comprise a foam, such as an open cell or closed cell polyurethane foam, polyethylene foam, hydrophilic foam, hydrogel, polyester weave, etc. In other examples, the wiper 916 may comprise a thin membrane of silicone rubber.

In addition or alternatively, in some examples one or more cylindrical lubricators 918 can be provided within the aperture 912 that will lubricate the guide wire 402 as it passes through the lubricator(s) 918. Each lubricator can comprise, for example, medical grade silicone oil, heparin solution, PTFE lubricant, mineral oil, petroleum jelly, etc.

In addition or alternatively, in some examples one or more valves 920 can be provided within the aperture 912 that can be actuated to selectively open and close fluid communication through aperture 912.

In the illustrated example, the Y-coupling 900 includes the combination of the smaller diameter portion 912a, the bushing 914, the wiper 916, the lubricator 918, and the valve 20 described above. In such examples, these four elements are preferably arranged such that the smaller diameter portion 912a is distal to the bushing 914, the bushing 914 is distal to the wiper 916, the wiper 916 is distal to the lubricator 918, and the lubricator 918 and distal to the valve 920, though other arrangements and/or combinations of these elements are possible in other examples.

In addition a seal may be used at the junction of the fluid path 910 and the channel 912 to restrict or eliminate fluid and debris from entering the channel. The seal may be an elastomer gasket such as a domed slit valve or flat seal that allows passage of the guide wire and in some configurations the clearance member.

Figure 26:
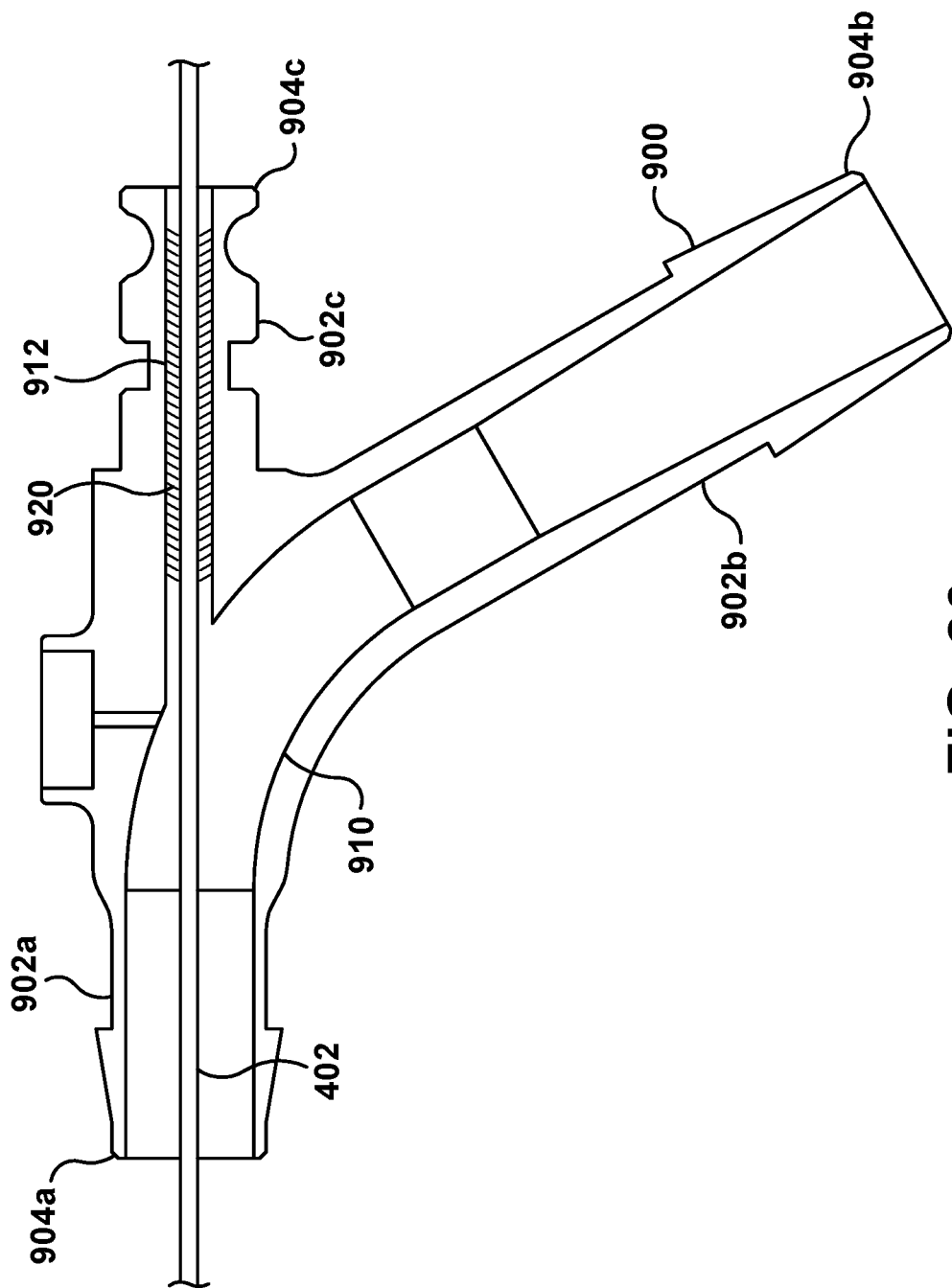
FIG. 26 is a cross-section view of another example Y-coupling that can be used to couple the medical tube of the fluid system with another structure.

Turning to FIG. 26, in some examples the Y-coupling 900 comprises bristles 920 within the aperture 912 that will mechanically remove material (e.g., clot) from the guide wire 402 as it translates through the aperture 912. The removal of material occurs at the turn off to the vacuum source to encourage such material to be removed toward the drainage canister. A valve may be provided to separate the bristles 920 from the fluid path to prevent blood clot from collecting on the bristles 920.

Figure 27:
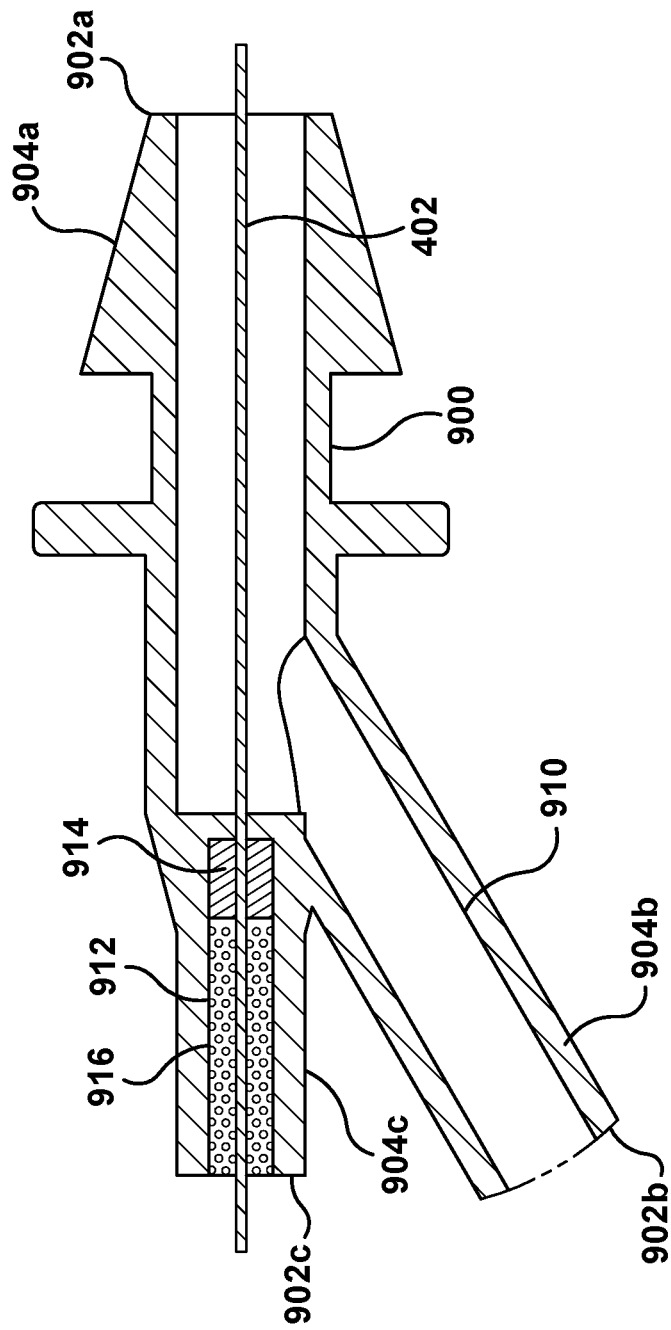
FIG. 27 is a cross-section view of another example Y-coupling that can be used to couple the medical tube of the fluid system with another structure.

Another example Y-coupling 900 is illustrated in FIG. 27 that has an aperture 912 that is closely fitting to the guide wire 402, which serves to scrape large blood clot and debris off of the wire, it has a bushing 914 that may be a rigid material (for e.g. delrin, polycarbonate, etc) or an elastomeric material such as silicone rubber that provides a seal to separate the fluid path, which may be under vacuum and the spool compartment, which may be at atmospheric pressure, it also serves to wipe additional blood and other fluid from the wire to reduce potential them to be brought into the spool compartment. The y-junction may also have a wiper 916, which may be made from open cell polyurethane foam, hydrophilic foam or other hydrophilic material such as a hydrogel, or other media, that is preferably porous. Moreover, the passageway 910 comprises two linear channels that intersect (as opposed to the curved channel as shown in FIGS. 25 and 26)

Figure 28:
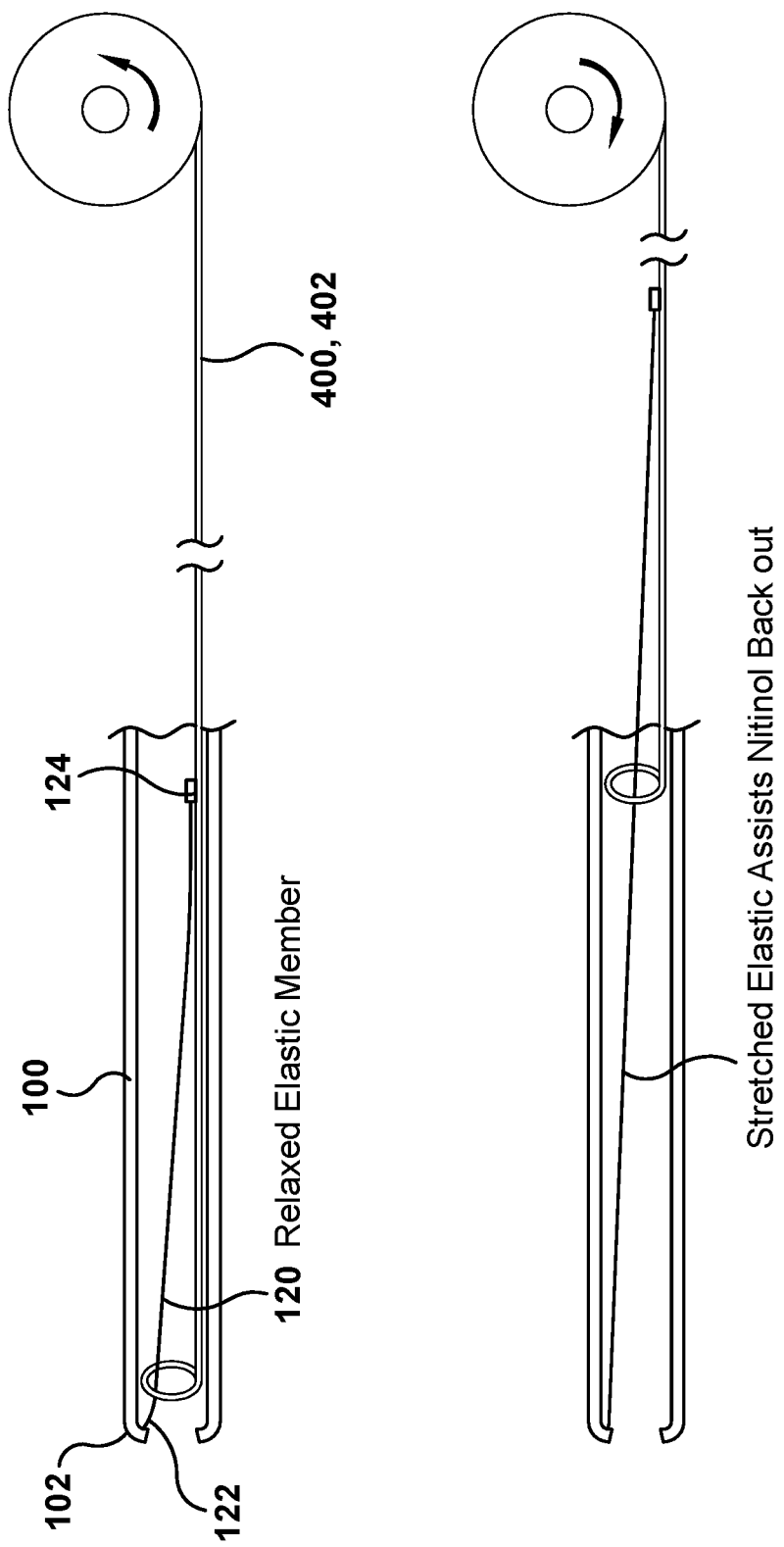
FIG. 28 is a schematic, partial-cross-section view showing an example elastic member for the fluid system.

Turning now to FIG. 28, an elastomeric return feature will now be described that can facilitate translation of the clearance wire assembly 400 through the medical tube 100. More specifically, the medical tube 100 in some examples can include an elastic member 120 extending within the passageway 106 that is fixedly coupled at its distal end 122 to a portion (e.g., the distal end 102) of the medical tube 100. The elastic member 120 can be further fixedly coupled at its proximal end 124 to a portion (e.g., guide wire 402) of the clearance wire assembly 400. The elastic member 120 can be configured such that as the clearance wire assembly 400 retracts through the medical tube 100 toward it proximal end 104, the elastic member 120 will be stretched by the clearance wire assembly 400. In this stretched state, the elastic member 120 will bias (e.g., pull) the clearance wire assembly 400 toward the distal end 102 of the medical tube 100. This bias from the elastic member 120 can help maintain the guide wire 402 of the clearance wire assembly 400 in a straight configuration within the medical tube 100, particularly during later advancement of the clearance wire assembly 400 toward the distal end 102 of the medical tube 100.

Figure 29:
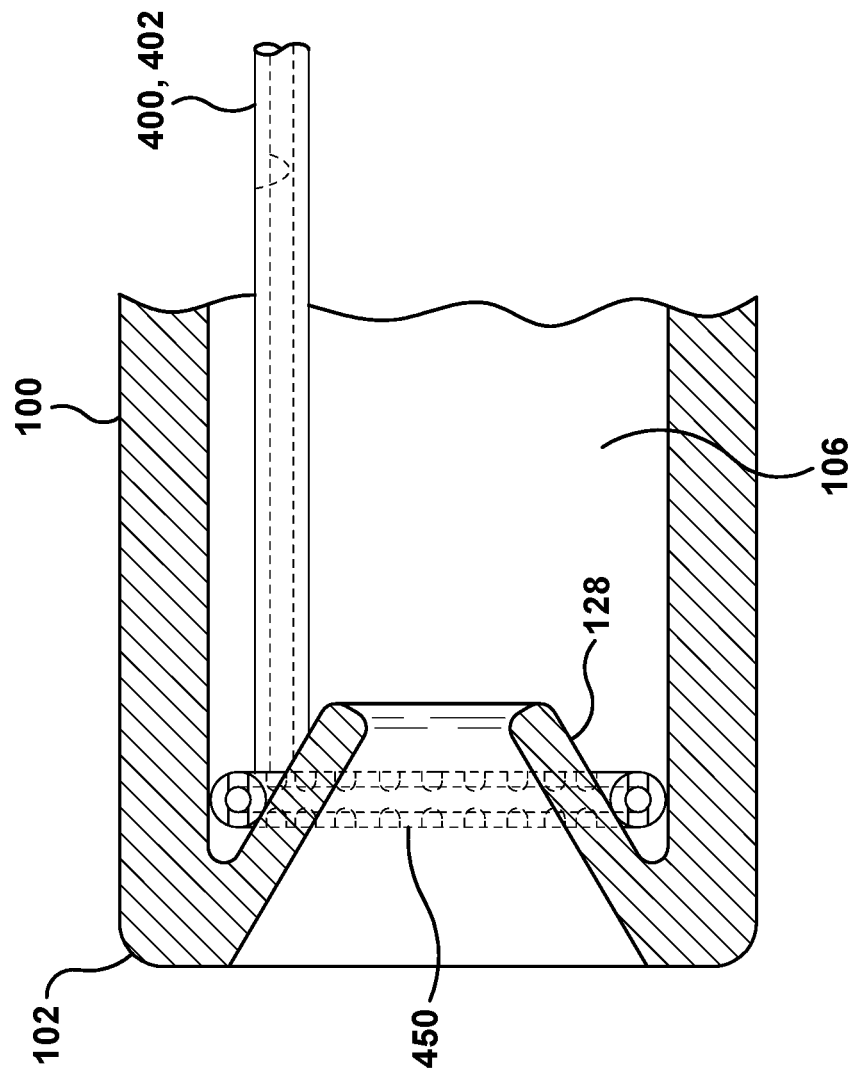
FIG. 29 is a schematic, partial-cross-section view showing an example conical seat for the fluid system.

Turning now to FIG. 29, the medical tube 100 in some examples can include a conical seat 123 that can facilitate disruption of material that may accumulate on a clearance member of the clearance wire assembly 400. The conical seat 128 extends radially inward and in a proximal direction from the distal end 102 of the medical tube 100, within the passageway 106. In this embodiment, the clearance wire assembly 400 includes a clearance member in the form of a loop 450. During or after use, the clearance wire assembly 400 can be advanced toward the distal end 102 of the medical tube 100 until the conical seat 128 projects through the clearance-member loop 450, thereby disrupting any material that may be accumulated within the loop 450.

As discussed above, the clearance wire assembly 400 can be moved within the medical tube 100 to facilitate the disruption of material accumulated within the medical tube 100. Preferably, an interior surface of the medical tube 100 will be coated with a layer of material that can reduce the frictional properties of the medical tube's, thereby reducing any resistance that the medical tube 100 may apply to movement of the clearance wire assembly 400 within the medical tube 100. Example materials that the inner surface of the medical tube 100 may be coated with are hydrophilic coatings, hydrogels, PVP, parylene C, parylene N, PTFE, Pebax and low friction silicone. However, in some examples, it may be desirable for portions of the medical tube's inner surface to not be coated with a friction-reducing layer.

For instance, as discussed above, the medical tube 100 is some examples can be fluidly coupled to various structure such as, for example, the drain assembly 200 described above and/or the drive systems 500, 600, 700, 800 described above. To fluidly couple the medical tube 100, fittings such as, for example, hose barbs may be utilized, which can be inserted within an end of the medical tube 100. The end of the medical tube 100 can then contract to provide a fluid tight seal between the fitting and the medical tube 100. However, if a friction-reducing agent is applied to the medical tube's inner surface where the medical tube 100 engages the fitting, a tight fluid seal may not be realized and the fitting could possibly disengage from the medical tube 100.

Accordingly, one aspect of the subject disclosure is directed to a method of applying a friction-reducing agent to the inner surface of the medical tube 100 wherein portion(s) (e.g., one or both ends or a portion in between) of the medical tube's inner surface are masked prior to application of the agent. The inner surface portion(s) can be masked using, for example, masking material that is applied to the surface portion with adhesive. Alternatively, a cylindrical plug may be inserted within the medical tube 100 that has an outer cylindrical wall having a diameter that substantially matches the diameter of the inner surface, and a length corresponding to the length of the tube's ID where it is desired not to apply a coating. In one example the plug is expandable and may be made from an elastomeric material such as a rubber. In another example the plug may have o-rings that engage and seal against the ID of the tube. In one example the plug is a tube that is open at its center for the passage of gas or fluid, thereby allowing coating to enter from both sides of the tube. Such a plug can block inner-surface portions engaged by the plug from exposure to the agent. Once the desired inner surface portion(s) have been masked, the friction-reducing agent (e.g., parylene) may be applied to the inner surface of the medical tube 100 to coat the remaining portions of the inner surface that are not masked. After the agent is applied (and in some examples, cured or dried), the masking device(s) (e.g. plug(s)) can be removed from the medical tube 100.

The method described above can produce a medical tube 100 having an interior surface that is partially coated with a friction-reducing agent such that one or more portions (e.g., one or both ends) of the medical tube's inner surface are not coated with the agent.

It should be appreciated that the method described above could be similarly applied to an exterior surface of the medical tube 100 to partially coat the exterior surface with a friction-reducing agent, particularly such that one or more portions (e.g., one or both ends) of the medical tube's exterior surface are not coated with the agent. For example, the outer surface portion(s) can be masked using, for example, masking material that is applied to the surface portion with adhesive. Alternatively, a cylindrical ring may be slid over the medical tube 100 that has an inner cylindrical wall having a diameter that substantially matches the diameter of the outer surface, and a length corresponding to the length of the tube's OD where it is desired not to apply a coating. In one example the ring is expandable and may be made from an elastomeric material such as a rubber. In another example the ring may have o-rings that engage and seal against the OD of the tube. Such a ring can block outer-surface portions engaged by the ring from exposure to the agent. Once the desired outer surface portion(s) have been masked, the friction-reducing agent (e.g., parylene) may be applied to the outer surface of the medical tube 100 to coat the remaining portions of the outer surface that are not masked. After the agent is applied (and in some examples, cured or dried), the masking device(s) (e.g. ring(s)) can be removed from the medical tube 100.

Figure 30:
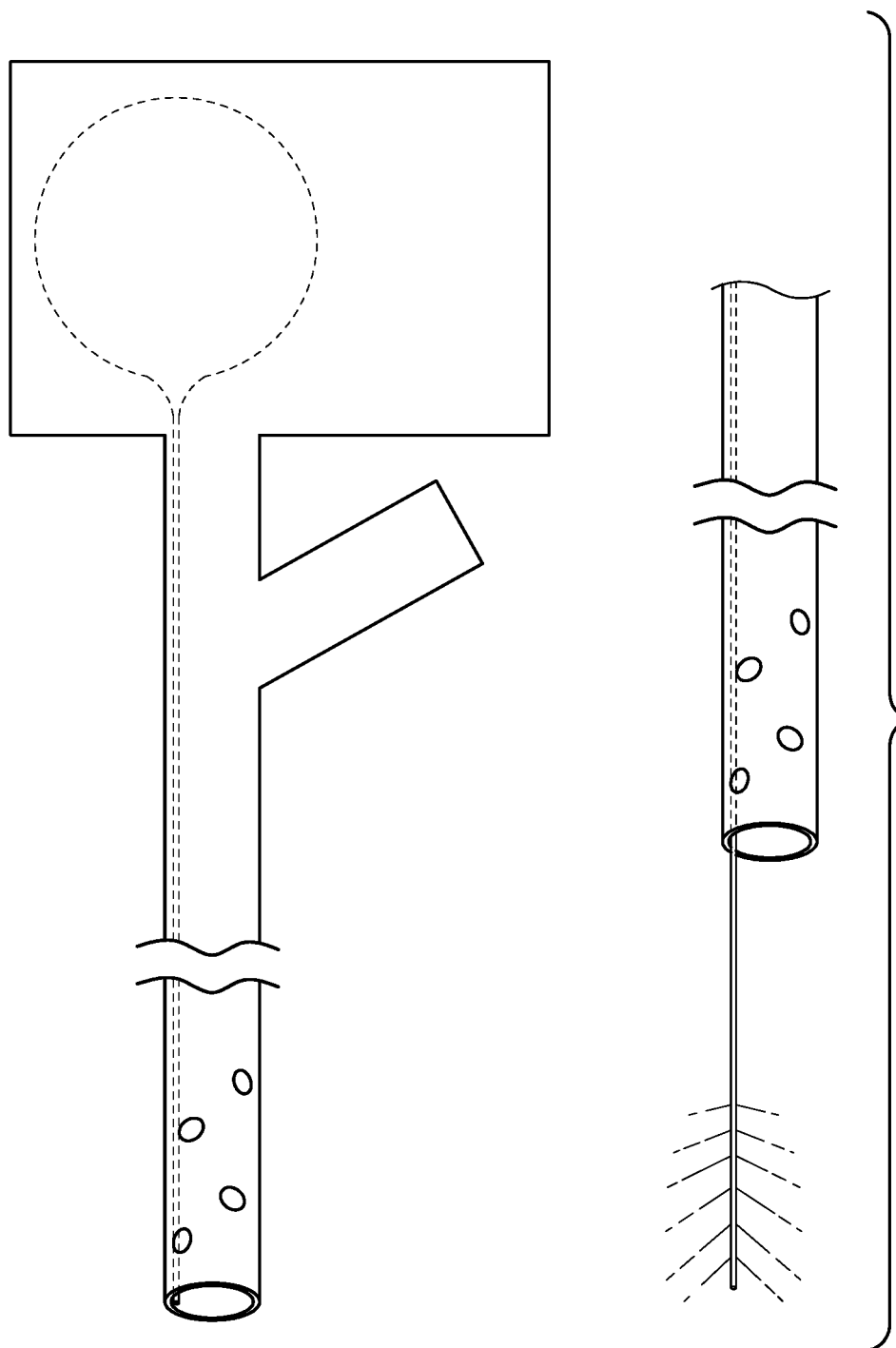
FIG. 30 is another embodiment of the described fluid system.

The fluid system 10 described above can be useful for delivering materials to the patient's body and/or removing materials from the patient's body through the described medical tube 100. In some aspects, the fluid system 10 can be configured to deliver therapeutic agents through the medical tube 100 to the patient. For instance, the fluid system 10 can comprise a delivery system that is fluidly coupled to the proximal end 104 of the medical tube 100 and is configured to deliver therapeutic agents through the medical tube 100 to the patient such as, for example, fluid (e.g., saline) controlled at a certain temperature (for example, body temperature), anti-inflammatory agents, anti-arrhythmic agents, infection medications, cardiovascular drugs, infectious disease control drugs, anti or pro inflammatory drugs, cancer treatment drugs, drugs to promote pleurodesis, pain relieving drugs, or any combination thereof. The delivery system can be operatively connected to a controller (e.g., controller 302) of a control system (e.g., control system 300), which can automatically operate the delivery system according to a particular program and/or in response to the parameter(s) detected by one or more sensors (e.g., sensors 306) of the control system. In one embodiment, the exact volume of the fluid inserted is tracked and subtracted from the total volume drained so that the volume of drainage is known, and it is known if all the fluid is later removed. With reference to FIG. 30, in one embodiment, a body space tube has one or more additional lumens in addition to a primary lumen. The additional lumen is for the administration of fluid outside of the body space tube to facilitate treating the space around the tube with the fluid. In one embodiment, the fluid is contained in a fluid reservoir that is part of tube clearance drive mechanism, or fluid collection canister. In one embodiment the fluid is controlled by a pump. In one embodiment, the fluid is administered by pressure applied to the reservoir, controlled by a fluid restricted or restrictive valve to maintain a steady volume of delivery to the body space outside the body space tube. In one embodiment, the lumen of the supplemental tube is the exact length of the body space drainage tube. In another embodiment, the tube can extend outside of the primary tube in one more directions to deliver fluid remote from the body space tube. In one embodiment, this fluid is temperature controlled, to be above body temperature, the same a body temperature, or below body temperature. In one embodiment, the fluid rate is controlled on a cc per minute basis. In one embodiment, the fluid administration is monitored and displayed digitally. In one embodiment, the fluid administration volume is monitored and subtracted from the total drainage so the exact amount of drainage recorded is divided into fluid delivery and fluid drained volumes. In one embodiment, total blood loss is estimated by a formula that includes total drainage minus administered fluid. In one embodiment, alarms are provided if the parameters of fluid delivered fail to evacuate, to prevent unrecognized retained administered fluid. In one embodiment the fluid removed is analyzed for properties such as pH, hematocrit, redox state, temperature (see our other list) to monitor the recovery of the body space with time from bleeding, infection, inflammation or other physical properties. In one embodiment, this is combined with medical tube clearance apparatus (all of our prior IP) to prevent the administration of fluid to the space that is not adequately drained due to body space drain tube occlusion from clot or other obstructing material. In one embodiment, the fluid is saline, or other physiologically balanced fluid replacement formulas. In one embodiment, the fluid is a chemical to induce pleurodesis (ie talc, tetracycline, doxycycline or other formulas meant to induce a sclerosis). In one embodiment the fluid is an antibiotic, antifungal, or other agent to treat an infection. In one embodiment, the agent is an anti-cancer agent to treat a neoplasm. In one embodiment, the fluid is an anti-inflammatory agent, anti-arrhythmic agent, anti-fibrinolytic agent, pro-fibrinolytic agents or any combination thereof. In one embodiment, the supplemental lumen can be advanced or retracted. In one embodiment, this can be done over a guide wire to prevent or minimize the potential for injury of internal structures.

Although the invention has been described with respect to certain embodiments, it is to be understood that the invention is not limited by the embodiments herein disclosed, which are exemplary and not limiting in nature, but is to include all modifications and adaptations thereto as would occur to the person having ordinary skill in the art upon reviewing the present disclosure, and as fall within the spirit and the scope of the invention as set forth in the appended claims.

What is claimed is:

1. A spool drive system for actuating a guide wire, said system comprising:
   a housing assembly having first and second opposing housing portions directly connected to one another and defining a common enclosure therebetween, and an inlet adapted to establish fluid communication between a medical tube and said enclosure;
   a spool within said enclosure, said spool being rotatable about an axis thereof to wind and unwind said guide wire on said spool, thereby withdrawing or advancing, respectively, said guide wire through said inlet;
   a track spaced from and extending at least partially about a perimeter of said spool following a curvature thereof within said enclosure, said track being adapted to direct said guide wire onto or off of said spool about the perimeter thereof as the spool is rotated;
   a motor disposed within said enclosure and operable to advance or withdraw said guide wire from or into said enclosure through said inlet, said first and second opposing housing portions being connected together to yield a single hand held assembly having both said spool and said motor within the common enclosure defined therebetween; and
   a partition wall disposed within and enclosed by the first and second opposing housing portions, said partition wall partitioning the enclosure into first and second portions thereof, wherein the spool is disposed within the first portion of the enclosure and the motor is disposed within the second portion of the enclosure.

2. The spool drive system of claim 1, said track being adapted to help maintain the guide wire in a wound state on said spool, preventing unwinding thereof that otherwise may result from stiffness of the guide wire.

3. The spool drive system of claim 1, said track comprising a grooved surface extending at least partially about the perimeter of the spool, said grooved surface comprising a plurality of circumferentially spaced grooves opposing a perimeter surface of the spool.

4. The spool drive system of claim 1, said track comprising a surface having a plurality of circumferentially spaced ridges opposing a perimeter surface of the spool.

5. The spool drive system of claim 1, said track comprising a plurality of circumferentially spaced wheels opposing a perimeter surface of the spool, said wheels being effective to rotatably engage the guide wire as it is wound or unwound on the spool.

6. The spool drive system of claim 5, said wheels being biased radially toward the perimeter surface of said spool in order to effectively engage said guide wire upon rotation of the spool.

7. The spool drive system of claim 1, said track comprising a plurality of ball bearings confined along a circular path opposing the perimeter surface of said spool.

8. The spool drive system of claim 1, said track comprising a low friction material or coating to provide a low-friction, sliding interface between said guide wire and features of said track upon rotation of said spool.

9. The spool drive system of claim 1, said motor being rotatably coupled to a shaft of said spool that extends through an aperture formed in the partition wall.

10. The spool drive system of claim 9, further comprising a battery within said enclosure for supplying electrical energy to said motor.

11. The spool drive system of claim 10, further comprising a controller within said enclosure and operatively connected to said motor, said controller being configured to operate said motor in order to actuate said guide wire by rotating said spool.

12. The spool drive system of claim 11, said controller being configured to selectively operate said motor according to a particular program and/or in response to sensed parameters that are communicated to said controller.

13. The spool drive system of claim 1, further comprising a battery sealed within said hand held assembly for supplying electrical energy to said motor, wherein said hand held assembly is configured to be disposable.

14. The spool drive system of claim 13, said hand held assembly being sterile.

15. The spool drive system of claim 1, further comprising a controller within said hand held assembly and operatively connected to said motor, said controller being configured to operate said motor in order to actuate said guide wire.

16. The spool drive system of claim 15, said controller being configured to selectively operate said motor according to a particular program and/or in response to sensed parameters that are communicated to said controller.

17. The spool drive system of claim 15, said controller being operatively connected to and forming a part of a control system that includes one or more sensors configured to detect one or more parameters and to send a signal to the controller indicating the detected one or more parameters.

18. The spool drive system of claim 17, said one or more sensors being configured to detect one or more of the following conditions of or within the medical tube: an orientation of the medical tube; a position of a clearance member within the medical tube; a pressure level, pH level, glucose level, protein level, or redox state of material within the medical tube; a blockage within the medical tube; a kink in the medical tube; an amount of fibrin clot degradation byproducts, endotoxins, bacterial infection byproducts, reactive oxygen species, or hematocrit in the medical tube.

19. The spool drive system of claim 17, said one or more sensors being configured to detect one or more of the following conditions of a patient who is being treated with the medical tube: temperature, heart rate and rhythm, arrhythmia, respiratory rate, inflammation level, pain level, or oxygen saturation level; orientation of the patient; activity level of the patient; coughing of the patient; a number of steps taken per day by the patient; a type of activity being performed by the patient; location of the patient; or length of time the patient has been in a particular location.

20. The spool drive system of claim 1, further comprising a Y-coupling having a first tube portion configured to be fluidly coupled to the medical tube, a second tube portion configured to be fluidly coupled to a suction source, and a third tube portion coupled to or comprising said inlet, wherein advancement and withdrawal of said guide wire extending from said inlet correspondingly advances and withdraws said guide wire through said first tube portion.

21. The spool drive system of claim 20, said Y-coupling comprising a cylindrical bushing in said third tube portion through which the guide wire will pass as it is advanced and withdrawn in order to wipe material from said guide wire so that said material does not enter the enclosure.

22. The spool drive system of claim 21, said cylindrical bushing comprising a porous material that can absorb fluid.

23. The spool drive system of claim 21, said third tube portion comprising a small-diameter, said bushing being located proximal to said small-diameter portion in said third tube portion, a wiper being disposed proximal to said bushing in said third tube portion, and a lubricator being disposed proximal to said wiper in said third tube portion, wherein said guide wire passes through each of said small-diameter portion, said bushing, said wiper, and said lubricator within said third tube portion on being advanced and withdrawn therethrough.

24. The spool drive system of claim 21, said Y-coupling further comprising bristles effective to abrade and remove material from the guide wire as it translates through the third tube portion.

25. The spool drive system of claim 1, further comprising a Y-coupling having a first tube portion configured to be fluidly coupled to the medical tube, a second tube portion configured to be fluidly coupled to a suction source, and a third tube portion coupled to or comprising said inlet, wherein advancement and withdrawal of said guide wire extending from said inlet correspondingly advances and withdraws said guide wire through said first tube portion.

26. A method comprising connecting the spool drive system of claim 1 to the medical tube to provide fluid communication between said tube and the inlet of the housing assembly, and operating the spool to advance or withdraw said guide wire through said inlet and through said medical tube.

* * * * *